(12) United States Patent
Jensen

(10) Patent No.: US 12,091,459 B2
(45) Date of Patent: *Sep. 17, 2024

(54) BISPECIFIC CHIMERIC ANTIGEN RECEPTORS, ENCODING POLYNUCLEOTIDES AND USE OF RECEPTORS THEREOF TO TREAT CANCER

(71) Applicant: Seattle Children's Hospital, Seattle, WA (US)

(72) Inventor: Michael Jensen, Bainbridge, WA (US)

(73) Assignee: Seattle Children's Hospital, Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/162,447

(22) Filed: Jan. 31, 2023

(65) Prior Publication Data

US 2023/0227551 A1    Jul. 20, 2023

Related U.S. Application Data

(60) Continuation of application No. 17/037,381, filed on Sep. 29, 2020, now Pat. No. 11,639,387, which is a continuation of application No. 16/240,652, filed on Jan. 4, 2019, now Pat. No. 10,829,556, which is a division of application No. 15/233,140, filed on Aug. 10, 2016, now Pat. No. 10,189,903, which is a continuation of application No. 14/376,610, filed as application No. PCT/US2013/025953 on Feb. 13, 2013, now Pat. No. 9,447,194.

(60) Provisional application No. 61/598,216, filed on Feb. 13, 2012.

(51) Int. Cl.
| | |
|---|---|
| C07K 16/28 | (2006.01) |
| A61K 35/17 | (2015.01) |
| A61K 38/00 | (2006.01) |
| A61K 38/17 | (2006.01) |
| A61K 47/68 | (2017.01) |
| C07K 14/705 | (2006.01) |
| C07K 14/71 | (2006.01) |
| C07K 14/725 | (2006.01) |
| C07K 16/46 | (2006.01) |
| C12N 5/0783 | (2010.01) |
| C12N 7/00 | (2006.01) |
| A61K 39/00 | (2006.01) |

(52) U.S. Cl.
CPC .......... *C07K 16/2803* (2013.01); *A61K 35/17* (2013.01); *A61K 38/179* (2013.01); *A61K 47/6849* (2017.08); *C07K 14/7051* (2013.01); *C07K 14/70517* (2013.01); *C07K 14/70521* (2013.01); *C07K 14/70578* (2013.01); *C07K 14/71* (2013.01); *C07K 16/2887* (2013.01); *C07K 16/2896* (2013.01); *C07K 16/468* (2013.01); *C12N 5/0636* (2013.01); *C12N 7/00* (2013.01); *A61K 38/00* (2013.01); *A61K 2039/505* (2013.01); *C07K 2317/24* (2013.01); *C07K 2317/31* (2013.01); *C07K 2317/56* (2013.01); *C07K 2317/622* (2013.01); *C07K 2319/03* (2013.01); *C07K 2319/74* (2013.01); *C12N 2510/00* (2013.01); *C12N 2740/15021* (2013.01); *C12N 2740/15043* (2013.01); *Y02A 50/30* (2018.01)

(58) Field of Classification Search
CPC ............ C07K 16/2803; C07K 2317/31; C07K 2317/56; C07K 2317/622; A61K 35/17
See application file for complete search history.

(56) References Cited

U.S. PATENT DOCUMENTS

| | | | |
|---|---|---|---|
| 5,741,899 A | 4/1998 | Capon et al. | |
| 6,103,521 A | 8/2000 | Capon et al. | |
| 9,447,194 B2 | 9/2016 | Jensen et al. | |
| 10,189,903 B2 | 1/2019 | Jensen | |
| 10,829,556 B2 | 11/2020 | Jensen | |
| 11,639,387 B2 | 5/2023 | Jensen | |
| 2003/0077249 A1 | 4/2003 | Bebbington et al. | |
| 2005/0113564 A1 | 5/2005 | Campana et al. | |
| 2010/0135974 A1 | 6/2010 | Eshhar et al. | |
| 2010/0189690 A1 | 7/2010 | Buchholz et al. | |
| 2010/0323420 A1 | 12/2010 | Crabtree et al. | |
| 2011/0044986 A1 | 2/2011 | Biere-Citron et al. | |

(Continued)

FOREIGN PATENT DOCUMENTS

| | | |
|---|---|---|
| AU | 2013221672 A1 | 8/2014 |
| AU | 2017264982 A1 | 7/2017 |

(Continued)

OTHER PUBLICATIONS

Communication pursuant to Rule 114(2) EPC for EP 19173955.6, dated Mar. 22, 2021, 5 pages.
Wilton et al., sdAb-DB: The Single Domain Antibody Database, ACS Synthetic Biology, 2018, vol. 7, pp. 2480-2484.
Ario de Marco, Biotechnological applications of recombinant single-domain antibody fragments, Microbial Cell Factories, 2011, vol. 10(44), pp. 1-14.

(Continued)

*Primary Examiner* — Robert S Landsman
(74) *Attorney, Agent, or Firm* — NIXON PEABODY LLP; Suwei Zhu; Linda B. Huber

(57) ABSTRACT

The invention is directed to a bispecific chimeric antigen receptor, comprising: (a) at least two antigen-specific targeting regions; (b) an extracellular spacer domain; (c) a transmembrane domain; (d) at least one co-stimulatory domain; and (e) an intracellular signaling domain, wherein each antigen-specific targeting region comprises an antigen-specific single chain Fv (scFv) fragment, and binds a different antigen, and wherein the bispecific chimeric antigen receptor is co-expressed with a therapeutic control. The invention also provides methods and uses of the bispecific chimeric antigen receptors.

30 Claims, 22 Drawing Sheets

Specification includes a Sequence Listing.

(56) References Cited

U.S. PATENT DOCUMENTS

| | | |
|---|---|---|
| 2011/0135657 A1 | 6/2011 | Hu et al. |
| 2011/0223129 A1 | 9/2011 | Jensen |
| 2013/0280220 A1 | 10/2013 | Ahmed et al. |
| 2015/0038684 A1 | 2/2015 | Jensen |
| 2017/0107285 A1 | 4/2017 | Jensen |
| 2019/0119382 A1 | 4/2019 | Jensen |
| 2021/0309740 A1 | 10/2021 | Jensen |

FOREIGN PATENT DOCUMENTS

| | | |
|---|---|---|
| AU | 2017264982 | 5/2020 |
| CA | 2861491 A1 | 8/2013 |
| EP | 2814846 A1 | 12/2014 |
| EP | 3594245 A1 | 1/2020 |
| HK | 1205144 A1 | 12/2015 |
| JP | 2010502232 A | 1/2010 |
| JP | 2010530737 A | 9/2010 |
| JP | 2011523400 A | 8/2011 |
| JP | 2015513394 A1 | 5/2015 |
| JP | 201955330 A | 6/2019 |
| JP | 6850528 B2 | 3/2021 |
| JP | 2021-121222 A | 8/2021 |
| WO | 2009134776 A2 | 11/2009 |
| WO | 2011041093 A1 | 4/2011 |
| WO | 2011056894 A2 | 5/2011 |
| WO | 2013123061 A1 | 8/2013 |

OTHER PUBLICATIONS

Cartellieri et al., Chimeric Antigen Receptor-Engineered T cells for Immunotherapy of Cancer, Journal of Biomedicine and Biotechnology, 2010, vol. 21(4), 13 pages.

Casucci et al., Suicide Gene Therapy to Increase the Safety of Chimeric Antigen Receptor-Redirected T Lymphocytes, Journal of Cancer, 2011, vol. 2, pp. 378-382.

Choi et al., Bispecific Antibodies Engage T Cells for Antitumor Immunotherapy, Expert Opinion on Biological Therapy, 2011, vol. 11(7), pp. 843-853.

Curran et al., Chimeric Antigen Receptor for T Cell Immunotherapy: Current Understanding and Future Directions, The Journal of Gene Medicine, 2010, vol. 14, pp. 405-415.

Grada et al., Targeting the Tumor Heterogeneity in Glioblastoma: A Chimeric Antigen Receptor Molecule Mediates Bispecific Activation and Targeting of T Lymphocytes, Neuro-Oncology, 2011, vol. 13, Supplemental 3, p. iii.115.

Grada et al., A Chimeric Antigen Receptor Molecule Mediates Bispecific Activation and Targeting of T Lymphocytes, Molecular Therapy, 2011, vol. 19, Supplement 2. p. S11.

Jena et al., Redirecting T-cell Specificity by Introducing a Tumor-Specific Chimeric Antigen Receptor, Blood, 2010, vol. 116(7), pp. 1035-1044.

Jensen et al., Antitransgene Rejection Responses Contribute to Attenuated Persistence of Adoptivily Transferred CD20/CD19-Specific Chimeric Antigen Receptor Redirected T Cells in Humans, Biol Blood Marrow Transplant, 2010, vol. 16(9), pp. 1245-1256.

Urbanska et al., Targeted Cancer Immunotherapy Via Combination of Designer Bispecific Antibody and Novel Gene-Engineered T Cells., Journal of Translational Medicine, 2014, vol. 12(1), pp. 347, 12 pages.

Wang et al., A Transgene-Encoded Cell Surface Polypeptide for Selection, In Vivo Tracking, and Ablation of Engineered Cells, Blood, 2011, vol. 118(5), pp. 1255-1263.

International Search Report and Written Opinion for PCT/US2013/25953 dated May 21, 2013, 16 pages.

International Preliminary Report on Patentability for PCT/US2013/25953 dated Aug. 19, 2014, 13 pages.

Extended Search Report for European Patent Application No. 13748596.7 dated Oct. 2, 2015, 10 pages.

Patel et al., T-Cell Killing of Heterogenous Tumor or Viral Targets with Bispecific Chimeric Immune Receptors, Cancer Gene Therapy, 2000, vol. 7(8), pp. 1127-1134.

Extended Search Report for European Patent Application No. 19173955.6 dated Dec. 17, 2019, 13 pages.

Grada et al., TanCAR: A Novel Bispecific Chimeric Antigen Receptor for Cancer Immunotherapy, Molecular-Therapy-Nucleic Acids, 2013, vol. 2, pp. 1-11.

Hudecek et al., Naïve CD4+ T Cells Modified to Express a ROR1-Specific CAR Mediate Anti-Tumor Activity and Provide Superior Help to CD8+ ROR1-CAR T Cells, Blood, 2011, vol. 118(21), Abstract No. 643.

Park et al., Adoptive Immunotherapy for B-Cell Malignancies with Autologous Chimeric Antigen Receptor Modified Tumor Targeted T-Cells, Discov Med, 2010, vol. 9(47), pp. 277-288.

Lum et al., Targeting T Cells with Bispecific Antibodies for Cancer Therapy, Bio Drugs, 2011, vol. 25(6), pp. 365-379.

Otz et al., A Bispecific Single-Chain Antibody that Mediates Target Cell-Restricted, Supra-AgonisticCD28 Stimulation and Killing of Lymphoma Cells, Leukemia, 2009, vol. 23, pp. 71-77.

Notice of Allowance for U.S. Appl. No. 16/240,652 dated Jul. 1, 2020, 9 pages.

Notice of Allowance for U.S. Appl. No. 15/233,140 dated Sep. 4, 2018, 9 pages.

Larson et al., CD19/CD20 Bispecific Chimeric Antigen Receptor (CAR) in Naïve/Memory T Cells for the Treatment of Relapsed or Refractory Non-Hodgkin Lymphoma, Cancer Discov., 2023, vol. 13(3), pp. 580-597.

ClinicalTrials.gov, A Feasibility and Safety Study of Dual Specificity CD19 and CD22 Car-T Cell Immunotherapy for CD19+ CD22+ Leukemia, Nov. 6, 2017, ClinicalTrials.gov Identifier: NCT03330691.

Kontermann, Dual targeting strategies with bisepcific antibodies, Landes Bioscience, 2012, vol. 4(2), pp. 182-197.

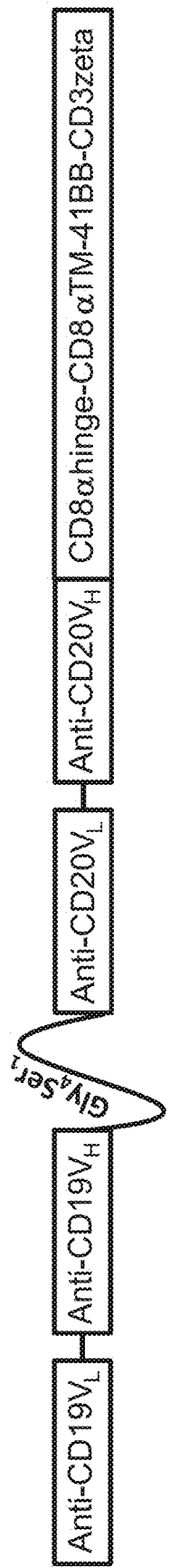

FIG. 3

GMCSFRs.s CD19scFv-Gly4Ser1linker-CD20scFv-IgG4Hinge-CD28tm-41BB-CD3zeta-T2A-EGFRt_epHIV7 atgctgctgctggtgaccagcctgctgctgtgcgagctgccccacccgcctttctgctgatccccatgacccagaccacctccagcctgagcgccagc
ctgggcgaccgggtgaccatcagctgccgggccagccaggacatcagcaagtacctgaactggtatcagcagaagcccgacggcaccgtcaagctg
ctgatctaccacaccagccggctgcacagcggcgtgcccagccggtttagcggcagcggctccggcaccgactacagcctgaccatctccaacctgga
acaggaagatatcgccacctacttttgccagcagggcaacacactgccctacacctttggcggcggaacaaagctggaaatcaccggcagcacctcc
ggcagcggcaagcctggcagcggcgagggcagcaccaaggcgaggtgaagctgcaggaaagcggccctggcctggtggccccagccagagcct
gagcgtgacctgcaccgtgagcggcgtgagcctgcccgactacggcgtgagctggatccggcagccccccaggaagggcctggaatggctgggcgt
gatctggggcagcgagaccacctactacaacagcgccctgaagagccggctgaccatcatcaaggacaacagcaagagccaggtgttcctgaagat
gaacagcctgcagaccgacgacaccgccatctactactgcgccaagcactactactacggcggcagctacgccatggactactggggccagggcacc
agcgtgaccgtgagcagcggaggtggtggatccgaggtgcagctgcagcagtcggggctgagctggtgaagcctggggcctcagtgaagatgtcct
gcaaggcttctggctacacatttaccagttacaatatgcactgggtaaagcagacacctggacagggcctggaatggattggagctatttatccagga
aatggtgatacttcctacaatcagaagttcaaaggcaaggccacattgactgcagacaaatcctccagcacagcctacatgcagctcagcagcctga
catctgaggactctgcggactattactgtgcaagatctaattattacggtagtagctactggttcttcgatgtctggggcgcagggaccacggtcaccgt
ctcctcaggcagtactagcggtggtggctccggggggcggttccggtggggcggcagcagcgacattgtgctgacccaatctccagctatcctgtctgc
atctccaggggagaaggtcacaatgacttgcagggccagctcaagtgtaaattacatggactggtaccagaagaagccaggatcctcccccaaaccc
tggatttatgccacatccaacctggcttctggagtccctgctcgcttcagtggcagtgggtctgggacctcttactctctcacaatcagcagagtggagg
ctgaagatgctgccacttattactgccagcagtggagttttaatccacccacgttcggaggggggaccaagctggaaataaaagagagcaagtacgg
accgccctgccccccttgccctatgttctgggtgctggtggtggtcggaggcgtgctggcctgctacagcctgctggtcaccgtggccttcatcatctttg
ggtgaaacggggcagaaagaaactcctgtatatattcaaacaaccatttatgagaccagtacaaactactcaagaggaagatggctgtagctgccga
tttccagaagaagaagaaggaggatgtgaactgcgggtgaagttcagcagaagcgccgacgcccctgcctaccagcagggccagaatcagctgtac
aacgagctgaacctgggcagaagggaagagtacgacgtcctggataagcggagaggccgggaccctgagatgggcggcaagcctcggcggaaga
accccaggaaggcctgtataacgaactgcagaaagacaagatggccgaggcctacagcgagatcggcatgaaggcgagcggaggcgggcaa
gggccacgacggcctgtatcagggcctgtccaccgccaccaaggatacctacgacgccctgcacatgcaggccctgccccccaaggctcgagggcggc
ggagagggcagaggaagtcttctaacatgcggtgacgtggaggagaatcccggccctaggatgcttctcctggtgacaagccttctgctctgtgagtt
accacacccagcattcctcctgatcccacgcaaagtgtgtaacggaataggtattggtgaatttaaagactcactctccataaatgctacgaatattaa
acacttcaaaaactgcacctccatcagtggcgatctccacatcctgccggtggcatttaggggtgactccttcacacatactcctcctctggatccacag
gaactggatattctgaaaaccgtaaaggaaatcacaggggttttgctgattcaggcttggcctgaaaacaggacggacctccatgcctttgagaacct
agaaatcatacgcggcaggaccaagcaacatggtcagttttctcttgcagtcgtcagcctgaacataacatccttgggattacgctccctcaaggagat
aagtgatggagatgtgataatttcaggaaacaaaaatttgtgctatgcaaatacaataaactggaaaaaactgtttgggacctccggtcagaaaacc
aaaattataagcaacagaggtgaaaacagctgcaaggccacaggccaggtctgccatgccttgtgctcccccgagggctgctggggcccggagccc
agggactgcgtctcttgccggaatgtcagccgaggcagggaatgcgtggacaagtgcaaccttctggagggtgagccaagggagtttgtggagaact
ctgagtgcatacagtgccacccagagtgcctgcctcaggccatgaacatcacctgcacaggacggggaccagacaactgtatccagtgtgcccacta
cattgacggcccccactgcgtcaagacctgcccggcaggagtcatgggagaaaacaaccctggtctggaagtacgcagacgccgccatgtgtgc
cacctgtgccatccaaactgcacctacggatgcactgggccaggtcttgaaggctgtccaacgaatgggcctaagatcccgtccatcgccactgggat
ggtgggggcctcctcttgctgctggtggtggccctggggatcggcctcttcatgtga

FIG. 4A

GMCSFRs.s CD19scFv-Gly4Ser1linker-CD20scFv-IgG4Hinge-CD28tm-41BB-CD3zeta-T2A-EGFRt_epHIV7

```
DNA: ATGCTGCTGCTGGTGACCAGCCTGCTGCTGTGCGAGCTGCCCCACCCCGCC
 AA:  M   L   L   L   V   T   S   L   L   L   C   E   L   P   H   P   A
DNA: TTTCTGCTGATCCCCATGACCCAGACCACCTCCAGCCTGAGCGCCAGCCTG
 AA:  F   L   L   I   P   M   T   Q   T   T   S   S   L   S   A   S   L
DNA: GGCGACCGGGTGACCATCAGCTGCCGGGCCAGCCAGGACATCAGCAAGTAC
 AA:  G   D   R   V   T   I   S   C   R   A   S   Q   D   I   S   K   Y
DNA: CTGAACTGGTATCAGCAGAAGCCCGACGGCACCGTCAAGCTGCTGATCTAC
 AA:  L   N   W   Y   Q   Q   K   P   D   G   T   V   K   L   L   I   Y
DNA: CACACCAGCCGGCTGCACAGCGGCGTGCCCAGCCGGTTTAGCGGCAGCGGC
 AA:  H   T   S   R   L   H   S   G   V   P   S   R   F   S   G   S   G
DNA: TCCGGCACCGACTACAGCCTGACCATCTCCAACCTGGAACAGGAAGATATC
 AA:  S   G   T   D   Y   S   L   T   I   S   N   L   E   Q   E   D   I
DNA: GCCACCTACTTTTGCCAGCAGGGCAACACACTGCCCTACACCTTTGGCGGC
 AA:  A   T   Y   F   C   Q   Q   G   N   T   L   P   Y   T   F   G   G
DNA: GGAACAAAGCTGGAAATCACCGGCAGCACCTCCGGCAGCGGCAAGCCTGGC
 AA:  G   T   K   L   E   I   T   G   S   T   S   G   S   G   K   P   G
DNA: AGCGGCGAGGGCAGCACCAAGGGCGAGGTGAAGCTGCAGGAAAGCGGCCCT
 AA:  S   G   E   G   S   T   K   G   E   V   K   L   Q   E   S   G   P
DNA: GGCCTGGTGGCCCCAGCCAGAGCCTGAGCGTGACCTGCACCGTGAGCGGC
 AA:  G   L   V   A   P   S   Q   S   L   S   V   T   C   T   V   S   G
DNA: GTGAGCCTGCCCGACTACGGCGTGAGCTGGATCCGGCAGCCCCCCAGGAAG
 AA:  V   S   L   P   D   Y   G   V   S   W   I   R   Q   P   P   R   K
DNA: GGCCTGGAATGGCTGGGCGTGATCTGGGGCAGCGAGACCACCTACTACAAC
 AA:  G   L   E   W   L   G   V   I   W   G   S   E   T   T   Y   Y   N
DNA: AGCGCCCTGAAGAGCCGGCTGACCATCATCAAGGACAACAGCAAGAGCCAG
 AA:  S   A   L   K   S   R   L   T   I   I   K   D   N   S   K   S   Q
DNA: GTGTTCCTGAAGATGAACAGCCTGCAGACCGACGACACCGCCATCTACTAC
 AA:  V   F   L   K   M   N   S   L   Q   T   D   D   T   A   I   Y   Y
DNA: TGCGCCAAGCACTACTACTACGGCGGCAGCTACGCCATGGACTACTGGGGC
 AA:  C   A   K   H   Y   Y   Y   G   G   S   Y   A   M   D   Y   W   G
DNA: CAGGGCACCAGCGTGACCGTGAGCAGCGGAGGTGGTGGATCCGAGGTGCAG
 AA:  Q   G   T   S   V   T   V   S   S   G   G   G   S   E   V   Q
DNA: CTGCAGCAGTCTGGGGCTGAGCTGGTGAAGCCTGGGGCCTCAGTGAAGATG
 AA:  L   Q   Q   S   G   A   E   L   V   K   P   G   A   S   V   K   M
DNA: TCCTGCAAGGCTTCTGGCTACACATTTACCAGTTACAATATGCACTGGGTA
 AA:  S   C   K   A   S   G   Y   T   F   T   S   Y   N   M   H   W   V
DNA: AAGCAGACACCTGGACAGGGCCTGGAATGGATTGGAGCTATTTATCCAGGA
 AA:  K   Q   T   P   G   Q   G   L   E   W   I   G   A   I   Y   P   G
DNA: AATGGTGATACTTCCTACAATCAGAAGTTCAAAGGCAAGGCCACATTGACT
 AA:  N   G   D   T   S   Y   N   Q   K   F   K   G   K   A   T   L   T
DNA: GCAGACAAATCCTCCAGCACAGCCTACATGCAGCTCAGCAGCCTGACATCT
 AA:  A   D   K   S   S   S   T   A   Y   M   Q   L   S   S   L   T   S
DNA: GAGGACTCTGCGGACTATTACTGTGCAAGATCTAATTATTACGGTAGTAGC
 AA:  E   D   S   A   D   Y   Y   C   A   R   S   N   Y   Y   G   S   S
DNA: TACTGGTTCTTCGATGTCTGGGGCGCAGGGACCACGGTCACCGTCTCCTCA
 AA:  Y   W   F   F   D   V   W   G   A   G   T   T   V   T   V   S   S
DNA: GGCAGTACTAGCGGTGGTGGCTCCGGGGGCGGTTCCGGTGGGGCGGCAGC
 AA:  G   S   T   S   G   G   G   S   G   G   G   S   G   G   G   S
DNA: AGCGACATTGTGCTGACCCAATCTCCAGCTATCCTGTCTGCATCTCCAGGG
 AA:  S   D   I   V   L   T   Q   S   P   A   I   L   S   A   S   P   G
DNA: GAGAAGGTCACAATGACTTGCAGGGCCAGCTCAAGTGTAAATTACATGGAC
 AA:  E   K   V   T   M   T   C   R   A   S   S   S   V   N   Y   M   D
```

FIG. 4B

```
DNA: TGGTACCAGAAGAAGCCAGGATCCTCCCCCAAACCCTGGATTTATGCCACA
AA:  W  Y  Q  K  K  P  G  S  S  P  K  P  W  I  Y  A  T
DNA: TCCAACCTGGCTTCTGGAGTCCCTGCTCGCTTCAGTGGCAGTGGGTCTGGG
AA:  S  N  L  A  S  G  V  P  A  R  F  S  G  S  G  S  G
DNA: ACCTCTTACTCTCTCACAATCAGCAGAGTGGAGGCTGAAGATGCTGCCACT
AA:  T  S  Y  S  L  T  I  S  R  V  E  A  E  D  A  A  T
DNA: TATTACTGCCAGCAGTGGAGTTTTAATCCACCCACGTTCGGAGGGGGGACC
AA:  Y  Y  C  Q  Q  W  S  F  N  P  P  T  F  G  G  G  T
DNA: AAGCTGGAAATAAAAGAGAGCAAGTACGGACCGCCCTGCCCCCCTTGCCCT
AA:  K  L  E  I  K  E  S  K  Y  G  P  P  C  P  P  C  P
DNA: ATGTTCTGGGTGCTGGTGGTGGTCGGAGGCGTGCTGGCCTGCTACAGCCTG
AA:  M  F  W  V  L  V  V  V  G  G  V  L  A  C  Y  S  L
DNA: CTGGTCACCGTGGCCTTCATCATCTTTTGGGTGAAACGGGGCAGAAAGAAA
AA:  L  V  T  V  A  F  I  I  F  W  V  K  R  G  R  K  K
DNA: CTCCTGTATATATTCAAACAACCATTTATGAGACCAGTACAAACTACTCAA
AA:  L  L  Y  I  F  K  Q  P  F  M  R  P  V  Q  T  T  Q
DNA: GAGGAAGATGGCTGTAGCTGCCGATTTCCAGAAGAAGAAGAAGGAGGATGT
AA:  E  E  D  G  C  S  C  R  F  P  E  E  E  E  G  G  C
DNA: GAACTGCGGGTGAAGTTCAGCAGAAGCGCCGACGCCCCTGCCTACCAGCAG
AA:  E  L  R  V  K  F  S  R  S  A  D  A  P  A  Y  Q  Q
DNA: GGCCAGAATCAGCTGTACAACGAGCTGAACCTGGGCAGAAGGGAAGAGTAC
AA:  G  Q  N  Q  L  Y  N  E  L  N  L  G  R  R  E  E  Y
DNA: GACGTCCTGGATAAGCGGAGAGGCCGGGACCCTGAGATGGGCGGCAAGCCT
AA:  D  V  L  D  K  R  R  G  R  D  P  E  M  G  G  K  P
DNA: CGGCGGAAGAACCCCCAGGAAGGCCTGTATAACGAACTGCAGAAAGACAAG
AA:  R  R  K  N  P  Q  E  G  L  Y  N  E  L  Q  K  D  K
DNA: ATGGCCGAGGCCTACAGCGAGATCGGCATGAAGGGCGAGCGGAGGCGGGGC
AA:  M  A  E  A  Y  S  E  I  G  M  K  G  E  R  R  R  G
DNA: AAGGGCCACGACGGCCTGTATCAGGGCCTGTCCACCGCCACCAAGGATACC
AA:  K  G  H  D  G  L  Y  Q  G  L  S  T  A  T  K  D  T
DNA: TACGACGCCCTGCACATGCAGGCCCTGCCCCCAAGGCTCGAGGGCGGCGGA
AA:  Y  D  A  L  H  M  Q  A  L  P  P  R  L  E  G  G  G
DNA: GAGGGCAGAGGAAGTCTTCTAACATGCGGTGACGTGGAGGAGAATCCCGGC
AA:  E  G  R  G  S  L  L  T  C  G  D  V  E  E  N  P  G
DNA: CCTAGGATGCTTCTCCTGGTGACAAGCCTTCTGCTCTGTGAGTTACCACAC
AA:  P  R  M  L  L  L  V  T  S  L  L  L  C  E  L  P  H
DNA: CCAGCATTCCTCCTGATCCCACGCAAAGTGTGTAACGGAATAGGTATTGGT
AA:  P  A  F  L  L  I  P  R  K  V  C  N  G  I  G  I  G
DNA: GAATTTAAAGACTCACTCTCCATAAATGCTACGAATATTAAACACTTCAAA
AA:  E  F  K  D  S  L  S  I  N  A  T  N  I  K  H  F  K
DNA: AACTGCACCTCCATCAGTGGCGATCTCCACATCCTGCCGGTGGCATTTAGG
AA:  N  C  T  S  I  S  G  D  L  H  I  L  P  V  A  F  R
DNA: GGTGACTCCTTCACACATACTCCTCCTCTGGATCCACAGGAACTGGATATT
AA:  G  D  S  F  T  H  T  P  P  L  D  P  Q  E  L  D  I
DNA: CTGAAAACCGTAAAGGAAATCACAGGGTTTTTGCTGATTCAGGCTTGGCCT
AA:  L  K  T  V  K  E  I  T  G  F  L  L  I  Q  A  W  P
DNA: GAAAACAGGACGGACCTCCATGCCTTTGAGAACCTAGAAATCATACGCGGC
AA:  E  N  R  T  D  L  H  A  F  E  N  L  E  I  I  R  G
DNA: AGGACCAAGCAACATGGTCAGTTTTCTCTTGCAGTCGTCAGCCTGAACATA
AA:  R  T  K  Q  H  G  Q  F  S  L  A  V  V  S  L  N  I
DNA: ACATCCTTGGGATTACGCTCCCTCAAGGAGATAAGTGATGGAGATGTGATA
AA:  T  S  L  G  L  R  S  L  K  E  I  S  D  G  D  V  I
DNA: ATTTCAGGAAACAAAAATTTGTGCTATGCAAATACAATAAACTGGAAAAAA
AA:  I  S  G  N  K  N  L  C  Y  A  N  T  I  N  W  K  K
DNA: CTGTTTGGGACCTCCGGTCAGAAAACCAAAATTATAAGCAACAGAGGTGAA
AA:  L  F  G  T  S  G  Q  K  T  K  I  I  S  N  R  G  E
```

FIG. 4C

```
DNA: AACAGCTGCAAGGCCACAGGCCAGGTCTGCCATGCCTTGTGCTCCCCGAG
AA:   N  S  C  K  A  T  G  Q  V  C  H  A  L  C  S  P  E
DNA: GGCTGCTGGGGCCCGGAGCCCAGGGACTGCGTCTCTTGCCGGAATGTCAGC
AA:   G  C  W  G  P  E  P  R  D  C  V  S  C  R  N  V  S
DNA: CGAGGCAGGGAATGCGTGGACAAGTGCAACCTTCTGGAGGGTGAGCCAAGG
AA:   R  G  R  E  C  V  D  K  C  N  L  L  E  G  E  P  R
DNA: GAGTTTGTGGAGAACTCTGAGTGCATACAGTGCCACCCAGAGTGCCTGCCT
AA:   E  F  V  E  N  S  E  C  I  Q  C  H  P  E  C  L  P
DNA: CAGGCCATGAACATCACCTGCACAGGACGGGGACCAGACAACTGTATCCAG
AA:   Q  A  M  N  I  T  C  T  G  R  G  P  D  N  C  I  Q
DNA: TGTGCCCACTACATTGACGGCCCCCACTGCGTCAAGACCTGCCCGGCAGGA
AA:   C  A  H  Y  I  D  G  P  H  C  V  K  T  C  P  A  G
DNA: GTCATGGGAGAAAACAACACCCTGGTCTGGAAGTACGCAGACGCCGGCCAT
AA:   V  M  G  E  N  N  T  L  V  W  K  Y  A  D  A  G  H
DNA: GTGTGCCACCTGTGCCATCCAAACTGCACCTACGGATGCACTGGGCCAGGT
AA:   V  C  H  L  C  H  P  N  C  T  Y  G  C  T  G  P  G
DNA: CTTGAAGGCTGTCCAACGAATGGGCCTAAGATCCCGTCCATCGCCACTGGG
AA:   L  E  G  C  P  T  N  G  P  K  I  P  S  I  A  T  G
DNA: ATGGTGGGGGCCCTCCTCTTGCTGCTGGTGGTGGCCCTGGGGATCGGCCTC
AA:   M  V  G  A  L  L  L  L  L  V  V  A  L  G  I  G  L
DNA: TTCATGTGA
AA:   F  M  *
```

FIG. 7

IgG4hinge-CD28tm-41BB-CD3Zeta gagagcaagtacggaccgccctgccccccttgccctatgttctgggtgctggtggtggtcggaggcgtgctggcctgctacagc
ctgctggtcaccgtggccttcatcatcttttgggtgaaacggggcagaaagaaactcctgtatatattcaaacaaccatttatgaga
ccagtacaaactactcaagaggaagatggctgtagctgccgatttccagaagaagaagaaggaggatgtgaactgcgggtgaa
gttcagcagaagcgccgacgcccctgcctaccagcagggccagaatcagctgtacaacgagctgaacctgggcagaaggga
agagtacgacgtcctggataagcggagaggccgggaccctgagatgggcggcaagcctcggcggaagaaccccaggaa
ggcctgtataacgaactgcagaaagacaagatggccgaggcctacagcgagatcggcatgaagggcgagcggaggcgggg
caagggccacgacggcctgtatcagggcctgtccaccgccaccaaggatacctacgacgccctgcacatgcaggccctgccc
ccaagg

```
DNA:  GAGAGCAAGTACGGACCGCCCTGCCCCCCTTGCCCTATGTTCTGGGTGCTG
AA:    E   S   K   Y   G   P   P   C   P   P   C   P   M   F   W   V   L

DNA:  GTGGTGGTCGGAGGCGTGCTGGCCTGCTACAGCCTGCTGGTCACCGTGGCC
AA:    V   V   V   G   G   V   L   A   C   Y   S   L   L   V   T   V   A

DNA:  TTCATCATCTTTTGGGTGAAACGGGGCAGAAAGAAACTCCTGTATATATTC
AA:    F   I   I   F   W   V   K   R   G   R   K   K   L   L   Y   I   F

DNA:  AAACAACCATTTATGAGACCAGTACAAACTACTCAAGAGGAAGATGGCTGT
AA:    K   Q   P   F   M   R   P   V   Q   T   T   Q   E   E   D   G   C

DNA:  AGCTGCCGATTTCCAGAAGAAGAAGAAGGAGGATGTGAACTGCGGGTGAAG
AA:    S   C   R   F   P   E   E   E   E   G   G   C   E   L   R   V   K

DNA:  TTCAGCAGAAGCGCCGACGCCCCTGCCTACCAGCAGGGCCAGAATCAGCTG
AA:    F   S   R   S   A   D   A   P   A   Y   Q   Q   G   Q   N   Q   L

DNA:  TACAACGAGCTGAACCTGGGCAGAAGGGAAGAGTACGACGTCCTGGATAAG
AA:    Y   N   E   L   N   L   G   R   R   E   E   Y   D   V   L   D   K

DNA:  CGGAGAGGCCGGGACCCTGAGATGGGCGGCAAGCCTCGGCGGAAGAACCCC
AA:    R   R   G   R   D   P   E   M   G   G   K   P   R   R   K   N   P

DNA:  CAGGAAGGCCTGTATAACGAACTGCAGAAAGACAAGATGGCCGAGGCCTAC
AA:    Q   E   G   L   Y   N   E   L   Q   K   D   K   M   A   E   A   Y

DNA:  AGCGAGATCGGCATGAAGGGCGAGCGGAGGCGGGGCAAGGGCCACGACGGC
AA:    S   E   I   G   M   K   G   E   R   R   R   G   K   G   H   D   G

DNA:  CTGTATCAGGGCCTGTCCACCGCCACCAAGGATACCTACGACGCCCTGCAC
AA:    L   Y   Q   G   L   S   T   A   T   K   D   T   Y   D   A   L   H

DNA:  ATGCAGGCCCTGCCCCCAAGG
AA:    M   Q   A   L   P   P   R
```

FIG. 8

GMCSFRss-CD19scFv-Gly4ser linker-CD20scFv-huIgG4hinge/CH2/CH3-CD28tm/CD28cyto-41BB-CD3Zeta atgctgctgctggtgaccagcctgctgctgtgcgagctgccccaccccgcctttctgctgatccccgacatccagatgacccaga
ccacctccagcctgagcgccagcctgggcgaccgggtgaccatcagctgccgggccagccaggacatcagcaagtacctga
actggtatcagcagaagcccgacggcaccgtcaagctgctgatctaccacaccagccggctgcacagcggcgtgcccagcc
ggtttagcggcagcggctccggcaccgactacagcctgaccatctccaacctggaacaggaagatatcgccacctacttttgcc
agcagggcaacacactgcccctacacctttggcggcggaacaaagctggaaatcaccggcagcacctccggcagcggcaagc
ctggcagcggcgagggcagcaccaagggcgaggtgaagctgcaggaaagcggccctggcctggtggcccccagccagag
cctgagcgtgacctgcaccgtgagcggcgtgagcctgcccgactacggcgtgagctggatccggcagccccccaggaaggg
cctggaatggctgggcgtgatctgggcagcgagaccacctactacaacagcgccctgaagagccggctgaccatcatcaag
gacaacagcaagagccaggtgttcctgaagatgaacagcctgcagaccgacgacaccgccatctactactgcgccaagcact
actactacggcggcagctacgccatggactactggggccagggcaccagcgtgaccgtgagcagcggaggtggtggatccg
aggtgcagctgcagcagtctggggctgagctggtgaagcctgggcctcagtgaagatgtcctgcaaggcttctggctacacat
ttaccagttacaatatgcactgggtaaagcagacacctggacagggcctggaatggattggagctatttatccaggaaatggtga
tacttcctacaatcagaagttcaaaggcaaggccacattgactgcagacaaatcctccagcacagcctacatgcagctcagcag
cctgacatctgaggactctgcggactattactgtgcaagatctaattattacggtagtagctactggttcttcgatgtctggggcgca
gggaccacggtcaccgtctcctcaggcagtactagcggtggtggctccggggggcggttccggtgggggcggcagcagcgac
attgtgctgacccaatctccagctatcctgtctgcatctccaggggagaaggtcacaatgacttgcagggccagctcaagtgtaa
attacatggactggtaccagaagaagccaggatcctcccccaaaccctggatttatgccacatccaacctggcttctggagtccct
gctcgcttcagtggcagtgggtctgggacctcttactctctcacaatcagcagagtggaggctgaagatgctgccacttattactg
ccagcagtggagttttaatccacccacgttcggaggggggaccaagctggaaataaaagagagcaagtacggaccgccctgc
cccccttgccctgcccccgagttcctgggcggacccagcgtgttcctgttcccccccaagcccaaggacaccctgatgatcagc
cggacccccgaggtgacctgcgtggtggtggacgtgagccaggaagatcccgaggtccagttcaattggtacgtggacggcg
tggaagtgcacaacgccaagaccaagcccagagaggaacagttcaacagcacctacggggtggtgtctgtgctgaccgtgct
gcaccaggactggctgaacggcaaagaatacaagtgcaaggtgtccaacaagggcctgcccagcagcatcgaaagaccat
cagcaaggccaagggccagcctcgcgagccccaggtgtacaccctgcctccctcccaggaagagatgaccaagaaccaggt
gtccctgacctgcctggtgaagggcttctaccccagcgacatcgccgtggagtgggagagcaacggccagcctgagaacaac
tacaagaccaccccctcccgtgctggacagcgacggcagcttcttcctgtacagccggctgaccgtggacaagagccggtggc
aggaaggcaacgtctttagctgcagcgtgatgcacgaggccctgcacaaccactacacccagaagagcctgagcctgtccctg
ggcaagatgttctgggtgctggtggtggtgggcgggtgctggcctgctacagcctgctggtgacagtggccttcatcatctttttg
ggtgcggagcaagcggagcagaggcggccacagcgactacatgaacatgaccccagacggcctggcccaccccggaag
cactaccagcccatacgccccacccagggactttgccgcctacagaagcaaacggggcagaaagaaactcctgtatatattcaa
acaaccatttatgagaccagtacaaactactcaagaggaagatggctgtagctgccgatttccagaagaagaagaaggaggat
gtgaactgcgggtgaagttcagcagaagcgccgacgcccctgcctaccagcagggccagaatcagctgtacaacgagctgaa
cctgggcagaagggaagagtacgacgtcctggataagcggagaggccgggaccctgagatgggcggcaagcctcggcgg
aagaaccccaggaaggcctgtataacgaactgcagaaagacaagatggccgaggcctacagcgagatcggcatgaaggg
cgagcggaggcggggcaaggccacgacggcctgtatcagggcctgtccaccgccaccaaggatacctacgacgccctgc
acatgcaggccctgccccaagg

FIG. 9A

GMCSFRss-CD19scFv-Gly4ser linker-CD20scFv-huIgG4hinge/CH2/CH3-CD28tm/CD28cyto-41BB-CD3Zeta

```
DNA: ATGCTGCTGCTGGTGACCAGCCTGCTGCTGTGCGAGCTGCCCCACCCCGCC
AA:  M   L   L   L   V   T   S   L   L   L   C   E   L   P   H   P   A

DNA: TTTCTGCTGATCCCCGACATCCAGATGACCCAGACCACCTCCAGCCTGAGC
AA:  F   L   L   I   P   D   I   Q   M   T   Q   T   T   S   S   L   S

DNA: GCCAGCCTGGGCGACCGGGTGACCATCAGCTGCCGGGCCAGCCAGGACATC
AA:  A   S   L   G   D   R   V   T   I   S   C   R   A   S   Q   D   I

DNA: AGCAAGTACCTGAACTGGTATCAGCAGAAGCCCGACGGCACCGTCAAGCTG
AA:  S   K   Y   L   N   W   Y   Q   Q   K   P   D   G   T   V   K   L

DNA: CTGATCTACCACACCAGCCGGCTGCACAGCGGCGTGCCCAGCCGGTTTAGC
AA:  L   I   Y   H   T   S   R   L   H   S   G   V   P   S   R   F   S

DNA: GGCAGCGGCTCCGGCACCGACTACAGCCTGACCATCTCCAACCTGGAACAG
AA:  G   S   G   S   G   T   D   Y   S   L   T   I   S   N   L   E   Q

DNA: GAAGATATCGCCACCTACTTTTGCCAGCAGGGCAACACACTGCCCTACACC
AA:  E   D   I   A   T   Y   F   C   Q   Q   G   N   T   L   P   Y   T

DNA: TTTGGCGGCGGAACAAAGCTGGAAATCACCGGCAGCACCTCCGGCAGCGGC
AA:  F   G   G   G   T   K   L   E   I   T   G   S   T   S   G   S   G

DNA: AAGCCTGGCAGCGGCGAGGGCAGCACCAAGGGCGAGGTGAAGCTGCAGGAA
AA:  K   P   G   S   G   E   G   S   T   K   G   E   V   K   L   Q   E

DNA: AGCGGCCCTGGCCTGGTGGCCCCAGCCAGAGCCTGAGCGTGACCTGCACC
AA:  S   G   P   G   L   V   A   P   S   Q   S   L   S   V   T   C   T

DNA: GTGAGCGGCGTGAGCCTGCCCGACTACGGCGTGAGCTGGATCCGGCAGCCC
AA:  V   S   G   V   S   L   P   D   Y   G   V   S   W   I   R   Q   P

DNA: CCCAGGAAGGGCCTGGAATGGCTGGGCGTGATCTGGGGCAGCGAGACCACC
AA:  P   R   K   G   L   E   W   L   G   V   I   W   G   S   E   T   T

DNA: TACTACAACAGCGCCCTGAAGAGCCGGCTGACCATCATCAAGGACAACAGC
AA:  Y   Y   N   S   A   L   K   S   R   L   T   I   I   K   D   N   S

DNA: AAGAGCCAGGTGTTCCTGAAGATGAACAGCCTGCAGACCGACGACACCGCC
AA:  K   S   Q   V   F   L   K   M   N   S   L   Q   T   D   D   T   A

DNA: ATCTACTACTGCGCCAAGCACTACTACTACGGCGGCAGCTACGCCATGGAC
AA:  I   Y   Y   C   A   K   H   Y   Y   Y   G   G   S   Y   A   M   D

DNA: TACTGGGGCCAGGGCACCAGCGTGACCGTGAGCAGCGGAGGTGGTGGATCC
AA:  Y   W   G   Q   G   T   S   V   T   V   S   S   G   G   G   S

DNA: GAGGTGCAGCTGCAGCAGTCTGGGGCTGAGCTGGTGAAGCCTGGGGCCTCA
AA:  E   V   Q   L   Q   Q   S   G   A   E   L   V   K   P   G   A   S

DNA: GTGAAGATGTCCTGCAAGGCTTCTGGCTACACATTTACCAGTTACAATATG
AA:  V   K   M   S   C   K   A   S   G   Y   T   F   T   S   Y   N   M
```

FIG. 9B

```
DNA: CACTGGGTAAAGCAGACACCTGGACAGGGCCTGGAATGGATTGGAGCTATT
AA:   H  W  V  K  Q  T  P  G  Q  G  L  E  W  I  G  A  I

DNA: TATCCAGGAAATGGTGATACTTCCTACAATCAGAAGTTCAAAGGCAAGGCC
AA:   Y  P  G  N  G  D  T  S  Y  N  Q  K  F  K  G  K  A

DNA: ACATTGACTGCAGACAAATCCTCCAGCACAGCCTACATGCAGCTCAGCAGC
AA:   T  L  T  A  D  K  S  S  S  T  A  Y  M  Q  L  S  S

DNA: CTGACATCTGAGGACTCTGCGGACTATTACTGTGCAAGATCTAATTATTAC
AA:   L  T  S  E  D  S  A  D  Y  Y  C  A  R  S  N  Y  Y

DNA: GGTAGTAGCTACTGGTTCTTCGATGTCTGGGGCGCAGGGACCACGGTCACC
AA:   G  S  S  Y  W  F  F  D  V  W  G  A  G  T  T  V  T

DNA: GTCTCCTCAGGCAGTACTAGCGGTGGTGGCTCCGGGGGCGGTTCCGGTGGG
AA:   V  S  S  G  S  T  S  G  G  G  S  G  G  G  S  G  G

DNA: GGCGGCAGCAGCGACATTGTGCTGACCCAATCTCCAGCTATCCTGTCTGCA
AA:   G  G  S  S  D  I  V  L  T  Q  S  P  A  I  L  S  A

DNA: TCTCCAGGGGAGAAGGTCACAATGACTTGCAGGGCCAGCTCAAGTGTAAAT
AA:   S  P  G  E  K  V  T  M  T  C  R  A  S  S  S  V  N

DNA: TACATGGACTGGTACCAGAAGAAGCCAGGATCCTCCCCCAAACCCTGGATT
AA:   Y  M  D  W  Y  Q  K  K  P  G  S  S  P  K  P  W  I

DNA: TATGCCACATCCAACCTGGCTTCTGGAGTCCCTGCTCGCTTCAGTGGCAGT
AA:   Y  A  T  S  N  L  A  S  G  V  P  A  R  F  S  G  S

DNA: GGGTCTGGGACCTCTTACTCTCTCACAATCAGCAGAGTGGAGGCTGAAGAT
AA:   G  S  G  T  S  Y  S  L  T  I  S  R  V  E  A  E  D

DNA: GCTGCCACTTATTACTGCCAGCAGTGGAGTTTTAATCCACCCACGTTCGGA
AA:   A  A  T  Y  Y  C  Q  Q  W  S  F  N  P  P  T  F  G

DNA: GGGGGGACCAAGCTGGAAATAAAAGAGAGCAAGTACGGACCGCCCTGCCCC
AA:   G  G  T  K  L  E  I  K  E  S  K  Y  G  P  P  C  P

DNA: CCTTGCCCTGCCCCCGAGTTCCTGGGCGGACCCAGCGTGTTCCTGTTCCCC
AA:   P  C  P  A  P  E  F  L  G  G  P  S  V  F  L  F  P

DNA: CCCAAGCCCAAGGACACCCTGATGATCAGCCGGACCCCCGAGGTGACCTGC
AA:   P  K  P  K  D  T  L  M  I  S  R  T  P  E  V  T  C

DNA: GTGGTGGTGGACGTGAGCCAGGAAGATCCCGAGGTCCAGTTCAATTGGTAC
AA:   V  V  V  D  V  S  Q  E  D  P  E  V  Q  F  N  W  Y

DNA: GTGGACGGCGTGGAAGTGCACAACGCCAAGACCAAGCCCAGAGAGGAACAG
AA:   V  D  G  V  E  V  H  N  A  K  T  K  P  R  E  E  Q

DNA: TTCAACAGCACCTACCGGGTGGTGTCTGTGCTGACCGTGCTGCACCAGGAC
AA:   F  N  S  T  Y  R  V  V  S  V  L  T  V  L  H  Q  D

DNA: TGGCTGAACGGCAAAGAATACAAGTGCAAGGTGTCCAACAAGGGCCTGCCC
AA:   W  L  N  G  K  E  Y  K  C  K  V  S  N  K  G  L  P
```

FIG. 9C

```
DNA: AGCAGCATCGAAAAGACCATCAGCAAGGCCAAGGGCCAGCCTCGCGAGCCC
AA:   S  S  I  E  K  T  I  S  K  A  K  G  Q  P  R  E  P

DNA: CAGGTGTACACCCTGCCTCCCTCCCAGGAAGAGATGACCAAGAACCAGGTG
AA:   Q  V  Y  T  L  P  P  S  Q  E  E  M  T  K  N  Q  V

DNA: TCCCTGACCTGCCTGGTGAAGGGCTTCTACCCCAGCGACATCGCCGTGGAG
AA:   S  L  T  C  L  V  K  G  F  Y  P  S  D  I  A  V  E

DNA: TGGGAGAGCAACGGCCAGCCTGAGAACAACTACAAGACCACCCCTCCCGTG
AA:   W  E  S  N  G  Q  P  E  N  N  Y  K  T  T  P  P  V

DNA: CTGGACAGCGACGGCAGCTTCTTCCTGTACAGCCGGCTGACCGTGGACAAG
AA:   L  D  S  D  G  S  F  F  L  Y  S  R  L  T  V  D  K

DNA: AGCCGGTGGCAGGAAGGCAACGTCTTTAGCTGCAGCGTGATGCACGAGGCC
AA:   S  R  W  Q  E  G  N  V  F  S  C  S  V  M  H  E  A

DNA: CTGCACAACCACTACACCCAGAAGAGCCTGAGCCTGTCCCTGGGCAAGATG
AA:   L  H  N  H  Y  T  Q  K  S  L  S  L  S  L  G  K  M

DNA: TTCTGGGTGCTGGTGGTGGTGGGCGGGGTGCTGGCCTGCTACAGCCTGCTG
AA:   F  W  V  L  V  V  V  G  G  V  L  A  C  Y  S  L  L

DNA: GTGACAGTGGCCTTCATCATCTTTTGGGTGCGGAGCAAGCGGAGCAGAGGC
AA:   V  T  V  A  F  I  I  F  W  V  R  S  K  R  S  R  G

DNA: GGCCACAGCGACTACATGAACATGACCCCCAGACGGCCTGGCCCCACCCGG
AA:   G  H  S  D  Y  M  N  M  T  P  R  R  P  G  P  T  R

DNA: AAGCACTACCAGCCCTACGCCCCACCCAGGGACTTTGCCGCCTACAGAAGC
AA:   K  H  Y  Q  P  Y  A  P  P  R  D  F  A  A  Y  R  S

DNA: AAACGGGGCAGAAAGAAACTCCTGTATATATTCAAACAACCATTTATGAGA
AA:   K  R  G  R  K  K  L  L  Y  I  F  K  Q  P  F  M  R

DNA: CCAGTACAAACTACTCAAGAGGAAGATGGCTGTAGCTGCCGATTTCCAGAA
AA:   P  V  Q  T  T  Q  E  E  D  G  C  S  C  R  F  P  E

DNA: GAAGAAGAAGGAGGATGTGAACTGCGGGTGAAGTTCAGCAGAAGCGCCGAC
AA:   E  E  E  G  G  C  E  L  R  V  K  F  S  R  S  A  D

DNA: GCCCCTGCCTACCAGCAGGGCCAGAATCAGCTGTACAACGAGCTGAACCTG
AA:   A  P  A  Y  Q  Q  G  Q  N  Q  L  Y  N  E  L  N  L

DNA: GGCAGAAGGGAAGAGTACGACGTCCTGGATAAGCGGAGAGGCCGGGACCCT
AA:   G  R  R  E  E  Y  D  V  L  D  K  R  R  G  R  D  P

DNA: GAGATGGGCGGCAAGCCTCGGCGGAAGAACCCCCAGGAAGGCCTGTATAAC
AA:   E  M  G  G  K  P  R  R  K  N  P  Q  E  G  L  Y  N

DNA: GAACTGCAGAAAGACAAGATGGCCGAGGCCTACAGCGAGATCGGCATGAAG
AA:   E  L  Q  K  D  K  M  A  E  A  Y  S  E  I  G  M  K

DNA: GGCGAGCGGAGGCGGGGCAAGGGCCACGACGGCCTGTATCAGGGCCTGTCC
AA:   G  E  R  R  R  G  K  G  H  D  G  L  Y  Q  G  L  S
```

FIG. 9D

```
DNA: ACCGCCACCAAGGATACCTACGACGCCCTGCACATGCAGGCCCTGCCCCCA
AA:   T  A  T  K  D  T  Y  D  A  L  H  M  Q  A  L  P  P

DNA: AGG
AA:   R
```

FIG. 10

GMCSFRss-CD19scFv-Gly4ser linker-CD20scFv-CD8alphaHinge-CD8alphaTM-41BB-CD3Zeta-T2A-EGFRt atgctgctgctggtgaccagcctgctgctgtgcgagctgccccaccccgcctttctgctgatccccgacatccagatgacccaga
ccacctccagcctgagcgccagcctgggcgaccgggtgaccatcagctgccgggccagccaggacatcagcaagtacctga
actggtatcagcagaagcccgacggcaccgtcaagctgctgatctaccacaccagccggctgcacagcggcgtgcccagcc
ggtttagcggcagcggctccggcaccgactacagcctgaccatctccaacctggaacaggaagatatcgccacctacttttgcc
agcagggcaacacactgcccctacacctttggcggcggaacaaagctggaaatcaccggcagcacctccggcagcggcaagc
ctggcagcggcgagggcagcaccaagggcgaggtgaagctgcaggaaagcggccctggcctggtggcccccagccagag
cctgagcgtgacctgcaccgtgagcggcgtgagcctgcccgactacggcgtgagctggatccggcagccccccaggaaggg
cctggaatggctgggcgtgatctgggcagcgagaccacctactacaacagcgccctgaagagccggctgaccatcatcaag
gacaacagcaagagccaggtgttcctgaagatgaacagcctgcagaccgacgacaccgccatctactactgcgccaagcact
actactacggcggcagctacgccatggactactggggccagggcaccagcgtgaccgtgagcagcggaggtggtggatccg
aggtgcagctgcagcagtctggggctgagctggtgaagcctggggcctcagtgaagatgtcctgcaaggcttctggctacacat
ttaccagttacaatatgcactgggtaaagcagacacctggacagggcctggaatggattggagctatttatccaggaaatggtga
tacttcctacaatcagaagttcaaaggcaaggccacattgactgcagacaaatcctccagcacagcctacatgcagctcagcag
cctgacatctgaggactctgcggactattactgtgcaagatctaattattacggtagtagctactggttcttcgatgtctggggcgca
gggaccacggtcaccgtctcctcaggcagtactagcggtggtggctccggggcggttccggtgggggcggcagcagcgac
attgtgctgacccaatctccagctatcctgtctgcatctccaggggagaaggtcacaatgacttgcagggccagctcaagtgtaa
attacatggactggtaccagaagaagccaggatcctcccccaaaccctggatttatgccacatccaacctggcttctggagtccct
gctcgcttcagtggcagtgggtctgggacctcttactctctcacaatcagcagagtggaggctgaagatgctgccacttattactg
ccagcagtggagttttaatccacccacgttcggaggggggaccaagctggaaataaaagagagcaagtacggaccgccctgc
cccccttgccctaagcctaccaccaccccctgccctagacctccaacacccgccccaacaatcgccagccagcctctgtctctg
aggcccgaggcttgtagaccagctgctggcggagccgtgcacaccagaggactggatttcgcctgcgacatctacatctgggc
ccctctggccggcacatgtggcgtgctgctgctgagcctcgtgatcaccaagcgggggcagaaagaaactgctgtacatctttaa
gcagcccttcatgcggcccgtgcagaccacccaggaagaggacggctgctcctgcagattccccgaggaagaagaaggcgg
ctgcgagctgagagtgaagttcagcagatccgccgacgcccctgcctaccagcagggacagaaccagctgtacaacgagctg
aacctgggcagacgggaagagtacgacgtgctggacaagcggagaggccgggaccctgagatgggcggaaagcccagaa
gaaagaaccccaggaaggcctgtataacgaactgcagaaagacaagatggccgaggcctacagcgagatcggaatgaag
ggcgagcggagaagaggcaaggccacgatggcctgtaccagggcctgagcaccgccaccaaggacacctatgacgccct
gcacatgcaggccctgcctccaagactcgagggcggcggagagggcagaggaagtcttctaacatgcggtgacgtggagga
gaatcccggccctaggatgcttctcctggtgacaagccttctgctctgtgagttaccacacccagcattcctcctgatcccacgca
aagtgtgtaacggaataggtattggtgaatttaaagactcactctccataaatgctacgaatattaaacacttcaaaaactgcacctc
catcagtggcgatctccacatcctgccggtggcatttagggggtgactccttcacacatactcctcctctggatccacaggaactgg
atattctgaaaaccgtaaaggaaatcacagggttttgctgattcaggcttggcctgaaaacaggacggacctccatgcctttgag
aacctagaaatcatacgcggcaggaccaagcaacatggtcagttttctcttgcagtcgtcagcctgaacataacatcttgggatt
acgctccctcaaggagataagtgatggagatgtgataatttcaggaaacaaaaatttgtgctatgcaaatacaataaactggaaaa
aactgtttgggacctccggtcagaaaaccaaaattataagcaacagaggtgaaaacagctgcaaggccacaggccaggtctgc
catgccttgtgctccccgagggctgctggggcccggagcccagggactgcgtctcttgccggaatgtcagccgaggcaggg
aatgcgtggacaagtgcaaccttctggagggtgagccaagggagtttgtggagaactctgagtgcatacagtgccacccagag
tgcctgcctcaggccatgaacatcacctgcacaggacgggaccagacaactgtatccagtgtgcccactacattgacggccc
ccactgcgtcaagacctgcccggcaggagtcatgggagaaaacaacaccctggtctggaagtacgcagacgccggccatgtg
tgccacctgtgccatccaaactgcacctacggatgcactgggccaggtcttgaaggctgtccaacgaatgggcctaagatccg
tccatcgccactgggatggtgggggccctcctcttgctgctggtggtggccctggggatcggcctcttcatgtga

FIG. 11A

GMCSFRss-CD19scFv-Gly4ser linker-CD20scFv-CD8alphaHinge-CD8alphaTM-41BB-CD3Zeta-T2A-EGFRt

```
DNA: ATGCTGCTGCTGGTGACCAGCCTGCTGCTGTGCGAGCTGCCCCACCCCGCC
AA:   M   L   L   L   V   T   S   L   L   L   C   E   L   P   H   P   A

DNA: TTTCTGCTGATCCCCGACATCCAGATGACCCAGACCACCTCCAGCCTGAGC
AA:   F   L   L   I   P   D   I   Q   M   T   Q   T   T   S   S   L   S

DNA: GCCAGCCTGGGCGACCGGGTGACCATCAGCTGCCGGGCCAGCCAGGACATC
AA:   A   S   L   G   D   R   V   T   I   S   C   R   A   S   Q   D   I

DNA: AGCAAGTACCTGAACTGGTATCAGCAGAAGCCCGACGGCACCGTCAAGCTG
AA:   S   K   Y   L   N   W   Y   Q   Q   K   P   D   G   T   V   K   L

DNA: CTGATCTACCACACCAGCCGGCTGCACAGCGGCGTGCCCAGCCGGTTTAGC
AA:   L   I   Y   H   T   S   R   L   H   S   G   V   P   S   R   F   S

DNA: GGCAGCGGCTCCGGCACCGACTACAGCCTGACCATCTCCAACCTGGAACAG
AA:   G   S   G   S   G   T   D   Y   S   L   T   I   S   N   L   E   Q

DNA: GAAGATATCGCCACCTACTTTTGCCAGCAGGGCAACACACTGCCCTACACC
AA:   E   D   I   A   T   Y   F   C   Q   Q   G   N   T   L   P   Y   T

DNA: TTTGGCGGCGGAACAAAGCTGGAAATCACCGGCAGCACCTCCGGCAGCGGC
AA:   F   G   G   G   T   K   L   E   I   T   G   S   T   S   G   S   G

DNA: AAGCCTGGCAGCGGCGAGGGCAGCACCAAGGGCGAGGTGAAGCTGCAGGAA
AA:   K   P   G   S   G   E   G   S   T   K   G   E   V   K   L   Q   E

DNA: AGCGGCCCTGGCCTGGTGGCCCCCAGCCAGAGCCTGAGCGTGACCTGCACC
AA:   S   G   P   G   L   V   A   P   S   Q   S   L   S   V   T   C   T

DNA: GTGAGCGGCGTGAGCCTGCCCGACTACGGCGTGAGCTGGATCCGGCAGCCC
AA:   V   S   G   V   S   L   P   D   Y   G   V   S   W   I   R   Q   P

DNA: CCCAGGAAGGGCCTGGAATGGCTGGGCGTGATCTGGGGCAGCGAGACCACC
AA:   P   R   K   G   L   E   W   L   G   V   I   W   G   S   E   T   T

DNA: TACTACAACAGCGCCCTGAAGAGCCGGCTGACCATCATCAAGGACAACAGC
AA:   Y   Y   N   S   A   L   K   S   R   L   T   I   I   K   D   N   S

DNA: AAGAGCCAGGTGTTCCTGAAGATGAACAGCCTGCAGACCGACGACACCGCC
AA:   K   S   Q   V   F   L   K   M   N   S   L   Q   T   D   D   T   A

DNA: ATCTACTACTGCGCCAAGCACTACTACTACGGCGGCAGCTACGCCATGGAC
AA:   I   Y   Y   C   A   K   H   Y   Y   Y   G   G   S   Y   A   M   D

DNA: TACTGGGGCCAGGGCACCAGCGTGACCGTGAGCAGCGGAGGTGGTGGATCC
AA:   Y   W   G   Q   G   T   S   V   T   V   S   S   G   G   G   G   S

DNA: GAGGTGCAGCTGCAGCAGTCTGGGGCTGAGCTGGTGAAGCCTGGGGCCTCA
AA:   E   V   Q   L   Q   Q   S   G   A   E   L   V   K   P   G   A   S

DNA: GTGAAGATGTCCTGCAAGGCTTCTGGCTACACATTTACCAGTTACAATATG
AA:   V   K   M   S   C   K   A   S   G   Y   T   F   T   S   Y   N   M
```

FIG. 11B

```
DNA: CACTGGGTAAAGCAGACACCTGGACAGGGCCTGGAATGGATTGGAGCTATT
AA:  H  W  V  K  Q  T  P  G  Q  G  L  E  W  I  G  A  I

DNA: TATCCAGGAAATGGTGATACTTCCTACAATCAGAAGTTCAAAGGCAAGGCC
AA:  Y  P  G  N  G  D  T  S  Y  N  Q  K  F  K  G  K  A

DNA: ACATTGACTGCAGACAAATCCTCCAGCACAGCCTACATGCAGCTCAGCAGC
AA:  T  L  T  A  D  K  S  S  S  T  A  Y  M  Q  L  S  S

DNA: CTGACATCTGAGGACTCTGCGGACTATTACTGTGCAAGATCTAATTATTAC
AA:  L  T  S  E  D  S  A  D  Y  Y  C  A  R  S  N  Y  Y

DNA: GGTAGTAGCTACTGGTTCTTCGATGTCTGGGGCGCAGGGACCACGGTCACC
AA:  G  S  S  Y  W  F  F  D  V  W  G  A  G  T  T  V  T

DNA: GTCTCCTCAGGCAGTACTAGCGGTGGTGGCTCCGGGGGCGGTTCCGGTGGG
AA:  V  S  S  G  S  T  S  G  G  G  S  G  G  G  S  G  G

DNA: GGCGGCAGCAGCGACATTGTGCTGACCCAATCTCCAGCTATCCTGTCTGCA
AA:  G  G  S  S  D  I  V  L  T  Q  S  P  A  I  L  S  A

DNA: TCTCCAGGGGAGAAGGTCACAATGACTTGCAGGGCCAGCTCAAGTGTAAAT
AA:  S  P  G  E  K  V  T  M  T  C  R  A  S  S  S  V  N

DNA: TACATGGACTGGTACCAGAAGAAGCCAGGATCCTCCCCCAAACCCTGGATT
AA:  Y  M  D  W  Y  Q  K  K  P  G  S  S  P  K  P  W  I

DNA: TATGCCACATCCAACCTGGCTTCTGGAGTCCCTGCTCGCTTCAGTGGCAGT
AA:  Y  A  T  S  N  L  A  S  G  V  P  A  R  F  S  G  S

DNA: GGGTCTGGGACCTCTTACTCTCTCACAATCAGCAGAGTGGAGGCTGAAGAT
AA:  G  S  G  T  S  Y  S  L  T  I  S  R  V  E  A  E  D

DNA: GCTGCCACTTATTACTGCCAGCAGTGGAGTTTTAATCCACCCACGTTCGGA
AA:  A  A  T  Y  Y  C  Q  Q  W  S  F  N  P  P  T  F  G

DNA: GGGGGGACCAAGCTGGAAATAAAAGAGAGCAAGTACGGACCGCCCTGCCCC
AA:  G  G  T  K  L  E  I  K  E  S  K  Y  G  P  P  C  P

DNA: CCTTGCCCTAAGCCTACCACCACCCCTGCCCCTAGACCTCCAACACCCGCC
AA:  P  C  P  K  P  T  T  T  P  A  P  R  P  P  T  P  A

DNA: CCAACAATCGCCAGCCAGCCTCTGTCTCTGAGGCCCGAGGCTTGTAGACCA
AA:  P  T  I  A  S  Q  P  L  S  L  R  P  E  A  C  R  P

DNA: GCTGCTGGCGGAGCCGTGCACACCAGAGGACTGGATTTCGCCTGCGACATC
AA:  A  A  G  G  A  V  H  T  R  G  L  D  F  A  C  D  I

DNA: TACATCTGGGCCCCTCTGGCCGGCACATGTGGCGTGCTGCTGCTGAGCCTC
AA:  Y  I  W  A  P  L  A  G  T  C  G  V  L  L  L  S  L

DNA: GTGATCACCAAGCGGGGCAGAAAGAAACTGCTGTACATCTTTAAGCAGCCC
AA:  V  I  T  K  R  G  R  K  K  L  L  Y  I  F  K  Q  P

DNA: TTCATGCGGCCCGTGCAGACCACCCAGGAAGAGGACGGCTGCTCCTGCAGA
AA:  F  M  R  P  V  Q  T  T  Q  E  E  D  G  C  S  C  R
```

FIG. 11C

```
DNA: TTCCCCGAGGAAGAAGAAGGCGGCTGCGAGCTGAGAGTGAAGTTCAGCAGA
AA:  F  P  E  E  E  E  G  G  C  E  L  R  V  K  F  S  R

DNA: TCCGCCGACGCCCTGCCTACCAGCAGGGACAGAACCAGCTGTACAACGAG
AA:  S  A  D  A  P  A  Y  Q  Q  G  Q  N  Q  L  Y  N  E

DNA: CTGAACCTGGGCAGACGGGAAGAGTACGACGTGCTGGACAAGCGGAGAGGC
AA:  L  N  L  G  R  R  E  E  Y  D  V  L  D  K  R  R  G

DNA: CGGGACCCTGAGATGGGCGGAAAGCCCAGAAGAAAGAACCCCCAGGAAGGC
AA:  R  D  P  E  M  G  G  K  P  R  R  K  N  P  Q  E  G

DNA: CTGTATAACGAACTGCAGAAGACAAGATGGCCGAGGCCTACAGCGAGATC
AA:  L  Y  N  E  L  Q  K  D  K  M  A  E  A  Y  S  E  I

DNA: GGAATGAAGGGCGAGCGGAGAAGAGGCAAGGGCCACGATGGCCTGTACCAG
AA:  G  M  K  G  E  R  R  R  G  K  G  H  D  G  L  Y  Q

DNA: GGCCTGAGCACCGCCACCAAGGACACCTATGACGCCCTGCACATGCAGGCC
AA:  G  L  S  T  A  T  K  D  T  Y  D  A  L  H  M  Q  A

DNA: CTGCCTCCAAGACTCGAGGGCGGCGGAGAGGGCAGAGGAAGTCTTCTAACA
AA:  L  P  P  R  L  E  G  G  G  E  G  R  G  S  L  L  T

DNA: TGCGGTGACGTGGAGGAGAATCCCGGCCCTAGGATGCTTCTCCTGGTGACA
AA:  C  G  D  V  E  E  N  P  G  P  R  M  L  L  V  T

DNA: AGCCTTCTGCTCTGTGAGTTACCACACCCAGCATTCCTCCTGATCCCACGC
AA:  S  L  L  L  C  E  L  P  H  P  A  F  L  L  I  P  R

DNA: AAAGTGTGTAACGGAATAGGTATTGGTGAATTTAAAGACTCACTCTCCATA
AA:  K  V  C  N  G  I  G  I  G  E  F  K  D  S  L  S  I

DNA: AATGCTACGAATATTAAACACTTCAAAAACTGCACCTCCATCAGTGGCGAT
AA:  N  A  T  N  I  K  H  F  K  N  C  T  S  I  S  G  D

DNA: CTCCACATCCTGCCGGTGGCATTTAGGGGTGACTCCTTCACACATACTCCT
AA:  L  H  I  L  P  V  A  F  R  G  D  S  F  T  H  T  P

DNA: CCTCTGGATCCACAGGAACTGGATATTCTGAAAACCGTAAAGGAAATCACA
AA:  P  L  D  P  Q  E  L  D  I  L  K  T  V  K  E  I  T

DNA: GGGTTTTGCTGATTCAGGCTTGGCCTGAAAACAGGACGGACCTCCATGCC
AA:  G  F  L  L  I  Q  A  W  P  E  N  R  T  D  L  H  A

DNA: TTTGAGAACCTAGAAATCATACGCGGCAGGACCAAGCAACATGGTCAGTTT
AA:  F  E  N  L  E  I  I  R  G  R  T  K  Q  H  G  Q  F

DNA: TCTCTTGCAGTCGTCAGCCTGAACATAACATCCTTGGGATTACGCTCCCTC
AA:  S  L  A  V  V  S  L  N  I  T  S  L  G  L  R  S  L

DNA: AAGGAGATAAGTGATGGAGATGTGATAATTTCAGGAAACAAAAATTTGTGC
AA:  K  E  I  S  D  G  D  V  I  I  S  G  N  K  N  L  C

DNA: TATGCAAATACAATAAACTGGAAAAAACTGTTTGGGACCTCCGGTCAGAAA
AA:  Y  A  N  T  I  N  W  K  K  L  F  G  T  S  G  Q  K
```

FIG. 11D

```
DNA: ACCAAAATTATAAGCAACAGAGGTGAAAACAGCTGCAAGGCCACAGGCCAG
 AA: T  K  I  I  S  N  R  G  E  N  S  C  K  A  T  G  Q

DNA: GTCTGCCATGCCTTGTGCTCCCCGAGGGCTGCTGGGGCCCGGAGCCCAGG
 AA: V  C  H  A  L  C  S  P  E  G  C  W  G  P  E  P  R

DNA: GACTGCGTCTCTTGCCGGAATGTCAGCCGAGGCAGGGAATGCGTGGACAAG
 AA: D  C  V  S  C  R  N  V  S  R  G  R  E  C  V  D  K

DNA: TGCAACCTTCTGGAGGGTGAGCCAAGGGAGTTTGTGGAGAACTCTGAGTGC
 AA: C  N  L  L  E  G  E  P  R  E  F  V  E  N  S  E  C

DNA: ATACAGTGCCACCCAGAGTGCCTGCCTCAGGCCATGAACATCACCTGCACA
 AA: I  Q  C  H  P  E  C  L  P  Q  A  M  N  I  T  C  T

DNA: GGACGGGGACCAGACAACTGTATCCAGTGTGCCCACTACATTGACGGCCCC
 AA: G  R  G  P  D  N  C  I  Q  C  A  H  Y  I  D  G  P

DNA: CACTGCGTCAAGACCTGCCCGGCAGGAGTCATGGGAGAAAACAACACCCTG
 AA: H  C  V  K  T  C  P  A  G  V  M  G  E  N  N  T  L

DNA: GTCTGGAAGTACGCAGACGCCGGCCATGTGTGCCACCTGTGCCATCCAAAC
 AA: V  W  K  Y  A  D  A  G  H  V  C  H  L  C  H  P  N

DNA: TGCACCTACGGATGCACTGGGCCAGGTCTTGAAGGCTGTCCAACGAATGGG
 AA: C  T  Y  G  C  T  G  P  G  L  E  G  C  P  T  N  G

DNA: CCTAAGATCCCGTCCATCGCCACTGGGATGGTGGGGGCCCTCCTCTTGCTG
 AA: P  K  I  P  S  I  A  T  G  M  V  G  A  L  L  L  L

DNA: CTGGTGGTGGCCCTGGGGATCGGCCTCTTCATGTGA
 AA: L  V  V  A  L  G  I  G  L  F  M  *
```

FIG. 12

T2A-EGFRt ctcgagggcggcggagagggcagaggaagtcttctaacatgcggtgacgtggaggagaatcccggccctaggatgcttctcc
tggtgacaagccttctgctctgtgagttaccacacccagcattcctcctgatcccacgcaaagtgtgtaacggaataggtattggtg
aatttaaagactcactctccataaatgctacgaatattaaacacttcaaaaactgcacctccatcagtggcgatctccacatcctgcc
ggtggcatttagggggtgactccttcacacatactcctcctctggatccacaggaactggatattctgaaaaccgtaaaggaaatca
cagggttttgctgattcaggcttggcctgaaaacaggacggacctccatgcctttgagaacctagaaatcatacgcggcaggac
caagcaacatggtcagttttctcttgcagtcgtcagcctgaacataacatccttgggattacgctccctcaaggagataagtgatgg
agatgtgataatttcaggaaacaaaaatttgtgctatgcaaatacaataaactggaaaaaactgtttgggacctccggtcagaaaa
ccaaaattataagcaacagaggtgaaaacagctgcaaggccacaggccaggtctgccatgccttgtgctcccccgagggctgc
tggggccccggagcccagggactgcgtctcttgccggaatgtcagccgaggcagggaatgcgtggacaagtgcaaccttctgg
agggtgagccaagggagtttgtggagaactctgagtgcatacagtgccacccagagtgcctgcctcaggccatgaacatcacc
tgcacaggacggggaccagacaactgtatccagtgtgcccactacattgacggcccccactgcgtcaagacctgcccggcag
gagtcatgggagaaaacaacaccctggtctggaagtacgcagacgccggccatgtgtgccaccgtgccatccaaactgcacc
tacggatgcactgggccaggtcttgaaggctgtccaacgaatgggcctaagatcccgtccatcgccactgggatggtgggggc
cctcctcttgctgctggtggtggccctggggatcggcctcttcatgtga

FIG. 13A

T2A-EGFRt

```
DNA: CTCGAGGGCGGCGGAGAGGGCAGAGGAAGTCTTCTAACATGCGGTGACGTG
AA:   L   E   G   G   G   E   G   R   G   S   L   L   T   C   G   D   V

DNA: GAGGAGAATCCCGGCCCTAGGATGCTTCTCCTGGTGACAAGCCTTCTGCTC
AA:   E   E   N   P   G   P   R   M   L   L   L   V   T   S   L   L   L

DNA: TGTGAGTTACCACACCCAGCATTCCTCCTGATCCCACGCAAAGTGTGTAAC
AA:   C   E   L   P   H   P   A   F   L   L   I   P   R   K   V   C   N

DNA: GGAATAGGTATTGGTGAATTTAAAGACTCACTCTCCATAAATGCTACGAAT
AA:   G   I   G   I   G   E   F   K   D   S   L   S   I   N   A   T   N

DNA: ATTAAACACTTCAAAAACTGCACCTCCATCAGTGGCGATCTCCACATCCTG
AA:   I   K   H   F   K   N   C   T   S   I   S   G   D   L   H   I   L

DNA: CCGGTGGCATTTAGGGGTGACTCCTTCACACATACTCCTCCTCTGGATCCA
AA:   P   V   A   F   R   G   D   S   F   T   H   T   P   P   L   D   P

DNA: CAGGAACTGGATATTCTGAAAACCGTAAAGGAAATCACAGGGTTTTTGCTG
AA:   Q   E   L   D   I   L   K   T   V   K   E   I   T   G   F   L   L

DNA: ATTCAGGCTTGGCCTGAAAACAGGACGGACCTCCATGCCTTTGAGAACCTA
AA:   I   Q   A   W   P   E   N   R   T   D   L   H   A   F   E   N   L

DNA: GAAATCATACGCGGCAGGACCAAGCAACATGGTCAGTTTTCTCTTGCAGTC
AA:   E   I   I   R   G   R   T   K   Q   H   G   Q   F   S   L   A   V

DNA: GTCAGCCTGAACATAACATCCTTGGGATTACGCTCCCTCAAGGAGATAAGT
AA:   V   S   L   N   I   T   S   L   G   L   R   S   L   K   E   I   S

DNA: GATGGAGATGTGATAATTTCAGGAAACAAAAATTTGTGCTATGCAAATACA
AA:   D   G   D   V   I   I   S   G   N   K   N   L   C   Y   A   N   T

DNA: ATAAACTGGAAAAAACTGTTTGGGACCTCCGGTCAGAAAACCAAAATTATA
AA:   I   N   W   K   K   L   F   G   T   S   G   Q   K   T   K   I   I

DNA: AGCAACAGAGGTGAAAACAGCTGCAAGGCCACAGGCCAGGTCTGCCATGCC
AA:   S   N   R   G   E   N   S   C   K   A   T   G   Q   V   C   H   A

DNA: TTGTGCTCCCCCGAGGGCTGCTGGGGCCCGGAGCCCAGGGACTGCGTCTCT
AA:   L   C   S   P   E   G   C   W   G   P   E   P   R   D   C   V   S

DNA: TGCCGGAATGTCAGCCGAGGCAGGGAATGCGTGGACAAGTGCAACCTTCTG
AA:   C   R   N   V   S   R   G   R   E   C   V   D   K   C   N   L   L

DNA: GAGGGTGAGCCAAGGGAGTTTGTGGAGAACTCTGAGTGCATACAGTGCCAC
AA:   E   G   E   P   R   E   F   V   E   N   S   E   C   I   Q   C   H

DNA: CCAGAGTGCCTGCCTCAGGCCATGAACATCACCTGCACAGGACGGGGACCA
AA:   P   E   C   L   P   Q   A   M   N   I   T   C   T   G   R   G   P

DNA: GACAACTGTATCCAGTGTGCCCACTACATTGACGGCCCCCACTGCGTCAAG
AA:   D   N   C   I   Q   C   A   H   Y   I   D   G   P   H   C   V   K
```

FIG. 13B

```
DNA: ACCTGCCCGGCAGGAGTCATGGGAGAAAACAACACCCTGGTCTGGAAGTAC
AA:  T  C  P  A  G  V  M  G  E  N  N  T  L  V  W  K  Y

DNA: GCAGACGCCGGCCATGTGTGCCACCTGTGCCATCCAAACTGCACCTACGGA
AA:  A  D  A  G  H  V  C  H  L  C  H  P  N  C  T  Y  G

DNA: TGCACTGGGCCAGGTCTTGAAGGCTGTCCAACGAATGGGCCTAAGATCCCG
AA:  C  T  G  P  G  L  E  G  C  P  T  N  G  P  K  I  P

DNA: TCCATCGCCACTGGGATGGTGGGGGCCCTCCTCTTGCTGCTGGTGGTGGCC
AA:  S  I  A  T  G  M  V  G  A  L  L  L  L  V  V  A

DNA: CTGGGGATCGGCCTCTTCATGTGA
AA:  L  G  I  G  L  F  M  *
```

BISPECIFIC CHIMERIC ANTIGEN RECEPTORS, ENCODING POLYNUCLEOTIDES AND USE OF RECEPTORS THEREOF TO TREAT CANCER

CROSS-REFERENCE TO RELATED APPLICATIONS

This application is a continuation of U.S. patent application Ser. No. 17/037,381, filed Sep. 29, 2020, now U.S. Pat. No. 11,639,387, which is a continuation of U.S. patent application Ser. No. 16/240,652, filed Jan. 4, 2019, now U.S. Pat. No. 10,829,556, which is a division of U.S. patent application Ser. No. 15/233,140, filed Aug. 10, 2016, now U.S. Pat. No. 10,189,903, which claims the benefit of priority under 35 U.S.C. § 120 as a continuation of U.S. patent application Ser. No. 14/376,610, filed Aug. 4, 2014, now U.S. Pat. No. 9,447,194, which is the National Phase of International Application No. PCT/US13/25953, filed Feb. 13, 2013, which designated the U.S. and that International Application was published under PCT Article 21(2) in English, which claims priority under 35 U.S.C. § 119(e) to U.S. provisional patent application No. 61/598,216, filed Feb. 13, 2012, the contents of each of which are herein incorporated by reference in their entirety.

REFERENCE TO SEQUENCE LISTING

The Sequence Listing submitted Jan. 24, 2024, as an electronic file named "067505_000001USC3_SequenceListing_2", having a size in bytes of 47,745 bytes and created on Jan. 11, 2024, is hereby incorporated by reference, which includes no new matter and replaces the sequence listing submitted on Jan. 31, 2023.

FIELD OF INVENTION

The invention relates to chimeric antigen receptors and to genetically engineered cells using the same.

BACKGROUND OF THE INVENTION

Current immunotherapies are designed to target single antigens on cancer cells. However, for example, cancer cells are unstable and some cells may no longer possess the target antigen. These cells, referred to as antigen loss escape variants, escape destruction by the therapy and may continue to grow and spread unchecked. Therefore there is a need in the art for therapies which prevent or minimize therapeutic failures in cancer and other diseases.

SUMMARY OF THE INVENTION

In an embodiment, the invention provides a bispecific chimeric antigen receptor, comprising (a) at least two antigen-specific targeting regions, (b) an extracellular spacer domain, (c) a transmembrane domain, (d) at least one co-stimulatory domain and (e) an intracellular signaling domain, wherein each antigen-specific targeting region comprises an antigen-specific single chain Fv (scFv) fragment, and binds a different antigen, and wherein the bispecific chimeric antigen receptor is co-expressed with a therapeutic control.

In an embodiment, the invention further provides a combination of a bispecific chimeric antigen receptor and a therapeutic control, wherein the bispecific chimeric antigen receptor comprises (a) at least two antigen-specific targeting regions, (b) an extracellular spacer domain, (c) a transmembrane domain, (d) at least one co-stimulatory domain and (e) an intracellular signaling domain, wherein each antigen-specific targeting region comprises an antigen-specific single chain Fv (scFv) fragment, and binds a different antigen.

In an embodiment, the invention further provides a bispecific chimeric antigen receptor, comprising (a) at least two antigen-specific targeting regions, (b) an extracellular spacer domain, (c) a transmembrane domain, (d) at least one co-stimulatory domain and (e) an intracellular signaling domain, wherein each antigen-specific targeting region comprises an antigen-specific single chain Fv (scFv) fragment, and binds a different antigen, and wherein the bispecific chimeric antigen receptor is co-expressed with truncated epidermal growth factor receptor (EGFRt).

In an embodiment, the invention further provides a bispecific chimeric antigen receptor, comprising (a) at least two antigen-specific targeting regions, (b) a CD8α hinge extracellular spacer domain, (c) a CD8α transmembrane domain, (d) a 4-1BB co-stimulatory domain and (vi) a CD3 zeta intracellular signaling domain, wherein each antigen-specific targeting region comprises an antigen-specific single chain Fv (scFv) fragment, and binds a different antigen, wherein the bispecific chimeric antigen receptor is co-expressed with EGFRt and wherein the bispecific chimeric antigen receptor and EGFRt are linked via a T2A linker.

In an embodiment, also provided are pharmaceutical compositions comprising the above-described bispecific chimeric antigen receptors, a combination of the bispecific chimeric antigen receptors and therapeutic controls, polypeptides encoding the bispecific chimeric antigen receptors, vectors, viruses and genetically engineered cells comprising the bispecific chimeric antigen receptors, vectors, viruses and genetically engineered cells comprising a combination of the bispecific chimeric antigen receptors and therapeutic controls, or combinations thereof, and a pharmaceutically acceptable carrier.

BRIEF DESCRIPTION OF FIGURES

Exemplary embodiments are illustrated in the referenced figures. It is intended that the embodiments and figures disclosed herein are to be considered illustrative rather than restrictive.

FIG. 2A depicts the components of an anti-CD19×CD20 CAR, and FIG. 2B depicts a complete cDNA packaged into an epHIV-7 lentivirus vector transfer plasmid, in accordance with an embodiment of the present invention.

FIG. 3 depicts, in accordance with an embodiment of the present invention, the nucleic acid sequence of a bispecific CAR CD19scFv-Gly4Ser1linker-CD20scFv-IgG4Hinge-CD28tm-41BB-CD3zeta-T2A-EGFRt_epHIV7 (SEQ ID NO: 1).

FIGS. 4A, 4B and 4C together depict, in accordance with an embodiment of the present invention, the nucleic acid sequence and the amino acid sequence of a bispecific CAR CD19scFv-Gly4Ser1linker-CD20scFv-IgG4Hinge- CD28tm-41BB-CD3zeta-T2A-EGFRt_epHIV7 (SEQ ID NO: 2, which includes the nucleic acid sequence from SEQ ID NO:1 and the amino acid sequence from SEQ ID NO: 3).

FIG. 6A Schematic diagrams of wild type versus chimeric cytokine receptors. The IL-7Rα constitutive cytokine receptor (CγCR7) consists of the human IL-7 cytokine tethered to the full length human IL-7Rα chain via a $(G_4S)_2$ (SEQ ID NO:16) linker. The IL-2Rβ constitutive cytokine receptor (CγCR2) is identical to CγCR7 except that the IL-7Rα intracellular signaling domain is replaced with the human IL-2/IL-15Rβ cytoplasmic domain. FIG. 6B Diagram of the expression construct CγCR-T2A-CD19t.

FIG. 7 depicts, in accordance with an embodiment of the present invention, the nucleic acid and amino acid sequences (SEQ ID NO: 4 and SEQ ID NO: 5) of an embodiment of the invention, namely a backbone CAR comprising the hinge region of IgG4, the transmembrane domain of CD28, the costimulatory domain of 4-1BB and the cytoplasmic domain of CD3zeta.

FIG. 8 depicts, in accordance with an embodiment of the present invention, the nucleic acid sequence of an embodiment of the invention, namely GMCSFRss-CD19scFv-Gly4Serlinker-CD20scFv-huIgGHinge/CH2/CH3-CD28tm/CD28cyto-41BB-CD3zeta (SEQ ID NO: 7). GMCSFRss is the signal sequence from GMCSFR.

FIGS. 9A, 9B, 9C and 9D together depict, in accordance with an embodiment of the present invention, the nucleic acid sequence and the amino acid sequence of an embodiment of the invention, namely GMCSFRss-CD19scFv-Gly4Serlinker-CD20scFv-huIgGHinge/CH2/CH3-CD28tm/CD28cyto-41BB-CD3zeta (SEQ ID NO: 8, which includes the nucleic acid sequence from SEQ ID NO: 7 and the amino acid sequence from SEQ ID NO: 9). GMCSFRss is the signal sequence from GMCSFR.

FIG. 10 depicts, in accordance with an embodiment of the present invention, the nucleic acid sequence of an embodiment of the invention, namely the GMCSFRss-CD19scFv-Gly4Serlinker-CD20scFv-CD8αHinge-CD8αtm-41BB-CD3zeta-T2A-EGFRt (SEQ ID NO: 10). GMCSFRss is the signal sequence from GMCSFR.

FIGS. 11A, 11B, 11C and 11D together depict, in accordance with an embodiment of the present invention, the nucleic acid sequence and the amino acid sequence of an embodiment of the invention, namely GMCSFRss-CD19scFv-Gly4Serlinker-CD20scFv-CD8αHinge-CD8αtm-41BB-CD3zeta-T2A-EGFRt (SEQ ID NO: 11, which includes the nucleic acid sequence from SEQ ID NO: 10 and the amino acid sequence from SEQ ID NO: 12). GMCSFRss is the signal sequence from GMCSFR.

FIG. 12 depicts, in accordance with an embodiment of the present invention, the nucleic acid sequence of an embodiment of an invention namely T2A-EGFRt (SEQ ID NO: 13).

FIGS. 13A and 13B together depict, in accordance with an embodiment of the present invention, the nucleic acid sequence and the amino acid sequence of an embodiment of the invention, namely T2A-EGFRt (SEQ ID NO: 14, which includes the nucleic acid sequence from SEQ ID NO: 13 and the amino acid sequence from SEQ ID NO: 15).

DETAILED DESCRIPTION OF THE INVENTION

Figure 1:
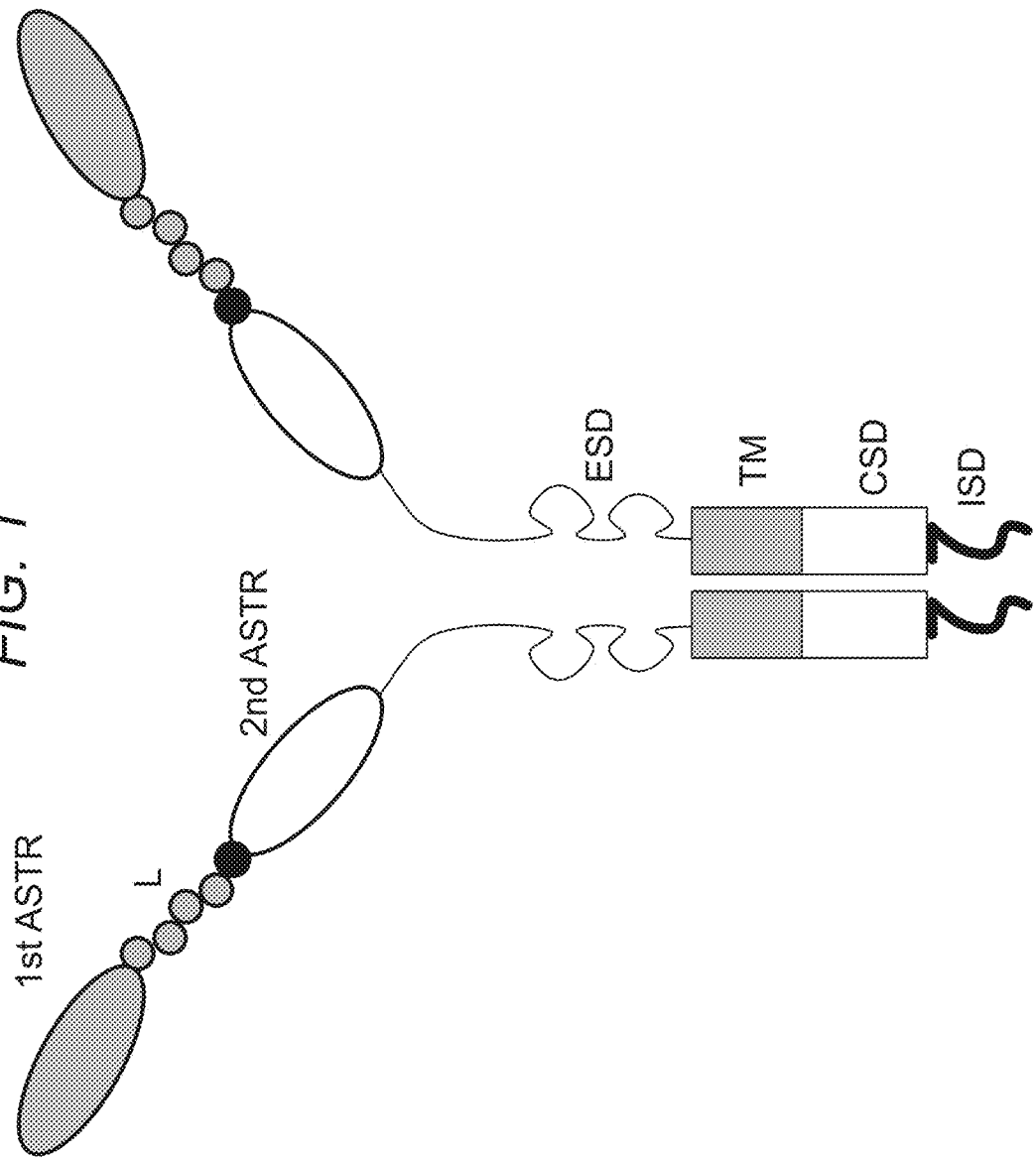
FIG. 1 depicts a schematic representation of a chimeric antigen receptor of the invention, in accordance with an embodiment of the present invention. ASTR is an antigen-specific targeting region, L is a linker, ESD is an extracellular spacer domain, TM is a transmembrane domain, CSD is a co-stimulatory domain, and ISD is an intracellular signaling domain, FIGS. 2A and 2B.

All references cited herein are incorporated by reference in their entirety as though fully set forth. Unless defined otherwise, technical and scientific terms used herein have the same meaning as commonly understood by one of ordinary skill in the art to which this invention belongs. Singleton et al., *Dictionary of Microbiology and Molecular Biology* 3rd ed., J. Wiley & Sons (New York, NY 2001); March, *Advanced Organic Chemistry Reactions, Mechanisms and Structure* 5th ed., J. Wiley & Sons (New York, NY 2001); and Sambrook and Russel, *Molecular Cloning: A Laboratory Manual* 3rd ed., Cold Spring Harbor Laboratory Press (Cold Spring Harbor, NY 2001), provide one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described. For purposes of the present invention, the following terms are defined below.

The invention described herein provides chimeric antigen receptors. Chimeric antigen receptors are engineered receptors which graft an immune specificity onto a genetically engineered cell. By housing specificities to multiple antigens in a single chimeric antigen receptor (CAR), various benefits may be achieved, including, among others, a significant reduction in effort as compared to making multiple T-cell products per patient.

Definitions

Components of the Chimeric Antigen Receptors

"Antigen-specific targeting region" (ASTR) as used herein refers to the region of the CAR which targets specific antigens. The CARs of the invention comprise at least two targeting regions which target at least two different antigens. In an embodiment, CARs comprise three or more targeting regions which target at least three or more different antigens. The targeting regions on the CAR are extracellular. In some embodiments, the antigen-specific targeting regions comprise an antibody or a functional equivalent thereof or a fragment thereof or a derivative thereof and each of the targeting regions target a different antigen. The targeting regions may comprise full length heavy chain, Fab fragments, single chain Fv (scFv) fragments, divalent single chain antibodies or diabodies, each of which are specific to the target antigen. There are, however, numerous alternatives, such as linked cytokines (which leads to recognition of cells bearing the cytokine receptor), affibodies, ligand binding domains from naturally occurring receptors, soluble protein/peptide ligand for a receptor (for example on a tumor cell), peptides, and vaccines to prompt an immune response, which may each be used in various embodiments of the invention. In fact, almost any molecule that binds a given antigen with high affinity can be used as an antigen-specific targeting region, as will be appreciated by those of skill in the art.

"Chimeric antigen receptor" or "CAR" or "CARs" as used herein refers to engineered receptors, which graft an antigen specificity onto cells (for example T cells such as naïve T cells, central memory T cells, effector memory T cells or combination thereof). CARs are also known as artificial T-cell receptors, chimeric T-cell receptors or chimeric immunoreceptors. The CARs of the invention comprise at least two antigen-specific targeting regions, an extracellular domain, a transmembrane domain, one or more co-stimulatory domains, and an intracellular signaling domain. The two or more antigen-specific targeting regions target at least two different antigens and may be arranged in tandem and separated by linker sequences. In an embodiment, the extracellular spacer domain is optional. In another embodiment, the CAR is a bispecific CAR. A bispecific CAR is specific to two different antigens.

"Co-stimulatory domain" (CSD) as used herein refers to the portion of the CAR which enhances the proliferation, survival and/or development of memory cells. The CARs of the invention may comprise one or more co-stimulatory domains. Each co-stimulatory domain comprises the costimulatory domain of any one or more of, for example, members of the TNFR superfamily, CD28, CD137 (4-1BB), CD134 (OX40), Dap10, CD27, CD2, CD5, ICAM-1, LFA-1(CD11a/CD18), Lck, TNFR-I, TNFR-II, Fas, CD30, CD40 or combinations thereof. Other co-stimulatory domains (e.g., from other proteins) will be apparent to those of skill in the art and may be used in connection with alternate embodiments of the invention.

"Extracellular spacer domain" (ESD) as used herein refers to the hydrophilic region which is between the antigen-specific targeting region and the transmembrane domain. In some embodiments, the CARs of the invention comprise an extracellular spacer domain. In other embodiments, the CARs of the invention do not comprise an extracellular spacer domain. The extracellular spacer domains include but are not limited to Fc fragments of antibodies or fragments or derivatives thereof, hinge regions of antibodies or fragments or derivatives thereof, CH2 regions of antibodies, CH3 regions of antibodies, artificial spacer sequences or combinations thereof. Examples of extracellular spacer domains include but are not limited to CD8α hinge, and artificial spacers made of polypeptides which may be as small as, for example, Gly3 or CH1 and CH3 domains of IgGs (such as human IgG4). In some embodiments, the extracellular spacer domain is any one or more of (i) a hinge, CH2 and CH3 regions of IgG4, (ii) a hinge region of IgG4, (iii) a hinge and CH2 of IgG4, (iv) a hinge region of CD8α, (v) a hinge, CH2 and CH3 regions of IgG1, (vi) a hinge region of IgG1 or (vi) a hinge and CH2 region of IgG1. Other extracellular spacer domains will be apparent to those of skill in the art and may be used in connection with alternate embodiments of the invention.

"Intracellular signaling domain" (ISD) or "cytoplasmic domain" as used herein refer to the portion of the CAR which transduces the effector function signal and directs the cell to perform its specialized function. Examples of domains that transduce the effector function signal include but are not limited to the ζ chain of the T-cell receptor complex or any of its homologs (e.g., η chain, FcεR1γ and β chains, MB1 (Igα) chain, B29 (Igβ) chain, etc.), human CD3 zeta chain, CD3 polypeptides (Δ, δ and ε), syk family tyrosine kinases (Syk, ZAP 70, etc.), src family tyrosine kinases (Lck, Fyn, Lyn, etc.) and other molecules involved in T-cell transduction, such as CD2, CD5 and CD28. Other intracellular signaling domains will be apparent to those of skill in the art and may be used in connection with alternate embodiments of the invention.

"Linker" (L) or "linker domain" or "linker region" as used herein refer to an oligo- or polypeptide region from about 1 to 100 amino acids in length, which links together any of the domains/regions of the CAR of the invention. Linkers may be composed of flexible residues like glycine and serine so that the adjacent protein domains are free to move relative to one another. Longer linkers may be used when it is desirable to ensure that two adjacent domains do not sterically interfere with one another. Linkers may be cleavable or non-cleavable. Examples of cleavable linkers include 2A linkers (for example T2A), 2A-like linkers or functional equivalents thereof and combinations thereof. In some embodiments, the linkers include the picornaviral 2A-like linker, CHYSEL sequences of porcine teschovirus (P2A), $Thosea$ $asigna$ virus (T2A) or combinations, variants and functional equivalents thereof. In other embodiments, the linker sequences may comprise Asp-Val/Ile-Glu-X-Asn-Pro-Gly$^{(2A)}$-Pro$^{(2B)}$ (SEQ ID NO:17) motif, which results in cleavage between the 2A glycine and the 2B proline. Other linkers will be apparent to those of skill in the art and may be used in connection with alternate embodiments of the invention.

"Transmembrane domain" (TMD) as used herein refers to the region of the CAR which crosses the plasma membrane. The transmembrane domain of the CAR of the invention is the transmembrane region of a transmembrane protein (for example Type I transmembrane proteins), an artificial hydrophobic sequence or a combination thereof. Other transmembrane domains will be apparent to those of skill in the art and may be used in connection with alternate embodiments of the invention.

Others

"Antigen loss escape variants" as used herein refer to cells which exhibit reduced or loss of expression of the target antigen, which antigens are targeted by the CARs of the invention.

"B-cell associated diseases" as used herein include B-cell immunodeficiencies, autoimmune diseases and/or excessive/uncontrolled cell proliferation associated with B-cells (including lymphomas and/or leukemias). Examples of such diseases, wherein bispecific CARs of the invention may be used for therapeutic approaches include but are not limited to systemic lupus erythematosus (SLE), diabetes, rheumatoid arthritis (RA), reactive arthritis, multiple sclerosis (MS), pemphigus vulgaris, celiac disease, Crohn's disease, inflammatory bowel disease, ulcerative colitis, autoimmune thyroid disease, X-linked agammaglobulinaemis, pre-B acute lymphoblastic leukemia, systemic lupus erythematosus, common variable immunodeficiency, chronic lymphocytic leukemia, diseases associated with selective IgA deficiency and/or IgG subclass deficiency, B lineage lymphomas (Hodgkin's lymphoma and/or non-Hodgkin's lymphoma), immunodeficiency with thymoma, transient hypogammaglobulinaemia and/or hyper IgM syndrome, as well as virally-mediated B-cell diseases such as EBV mediated lymphoproliferative disease, and chronic infections in which B-cells participate in the pathophysiology.

"Beneficial results" may include, but are in no way limited to, lessening or alleviating the severity of the disease condition, preventing the disease condition from worsening, curing the disease condition, preventing the disease condition from developing, lowering the chances of a patient developing the disease condition and prolonging a patient's life or life expectancy.

"Cancer" and "cancerous" refer to or describe the physiological condition in mammals that is typically characterized by unregulated cell growth. Examples of cancer include, but are not limited to B-cell lymphomas (Hodgkin's lymphomas and/or non-Hodgkins lymphomas), brain tumor, breast cancer, colon cancer, lung cancer, hepatocellular cancer, gastric cancer, pancreatic cancer, cervical cancer, ovarian cancer, liver cancer, bladder cancer, cancer of the urinary tract, thyroid cancer, renal cancer, carcinoma, melanoma, head and neck cancer, brain cancer, and prostate cancer, including but not limited to androgen-dependent prostate cancer and androgen-independent prostate cancer.

"Co-express" as used herein refers to simultaneous expression of two or more genes. Genes may be nucleic acids encoding, for example, a single protein or a chimeric protein as a single polypeptide chain. For example, the CARs of the invention may be co-expressed with a therapeutic control (for example truncated epidermal growth factor (EGFRt)), wherein the CAR is encoded by a first polynucleotide chain and the therapeutic control is encoded by a second polynucleotide chain. In an embodiment, the first and second polynucleotide chains are linked by a nucleic acid sequence that encodes a cleavable linker. The polynucleotides encoding the CAR and the therapeutic control system may be linked by IRES sequences. Alternately, the CAR and the therapeutic control are encoded by two different polynucleotides that are not linked via a linker but are instead encoded by, for example, two different vectors. Further, the CARs of the invention may be co-expressed with a therapeutic control and CCR, a therapeutic control and DHFR (for example mutant DHFR) or a therapeutic control and CCR and DHFR (for example mutant DHFR). The CAR, therapeutic control and CCR may be co-expressed and encoded by first, second and third polynucleotide sequences, respectively, wherein the first, second and third polynucleotide sequences are linked via IRES sequences or sequences encoding cleavable linkers. Alternately, these sequences are not linked via linkers but instead are encoded via, for example, separate vectors. The CAR, therapeutic control and DHFR (for example mutant DHFR) may be co-expressed and encoded by first, second and fourth polynucleotide sequences, respectively, wherein the first, second and fourth polynucleotide sequences are linked via IRES sequences or via sequences encoding cleavable linkers. Alternately, these sequences are not linked via linkers but instead encoded via, for example, separate vectors. The CAR, therapeutic control, CCR and DHFR (for example mutant DHFR) may be co-expressed and encoded by first, second, third and fourth polynucleotide sequences, respectively, wherein the first, second, third and fourth polynucleotide sequences are linked via IRES sequences or sequences encoding cleavable linkers. Alternately, these sequences are not linked via linkers but instead are encoded via, for example, separate vectors. If the aforementioned sequences are encoded by separate vectors, these vectors may be simultaneously or sequentially transfected.

"Conditions", "disease conditions," "diseases" and "disease state" as used herein include physiological states in which diseased cells may be targeted with the CARs of the invention, expressing, for example, antibodies against specific antigens on the diseased cells. Examples of antigens which may be targeted include but are not limited to antigens expressed on B-cells (such as CD19 and CD20), antigens expressed on carcinomas, sarcomas, lymphomas, leukemia, germ cell tumors, blastomas, antigens expressed on various immune cells, and antigens expressed on cells associated with various hematologic diseases, autoimmune diseases, and/or inflammatory diseases.

"Disease targeted by genetically modified cells" as used herein encompasses the targeting of any cell involved in any manner in any disease by the genetically modified cells of the invention, irrespective of whether the genetically modified cells target diseased cells or healthy cells to effectuate a therapeutically beneficial result. The genetically modified cells include but are not limited to genetically modified T-cells, NK cells, hematopoietic stem cells, pluripotent embryonic stem cells or embryonic stem cells. The genetically modified cells express the CARs of the invention, which CARs may target any of the antigens expressed on the surface of target cells. Examples of antigens which may be targeted include but are not limited to antigens expressed on B-cells; antigens expressed on carcinomas, sarcomas, lymphomas, leukemia, germ cell tumors, and blastomas; antigens expressed on various immune cells; and antigens expressed on cells associated with various hematologic diseases, autoimmune diseases, and/or inflammatory diseases. Other antigens that may be targeted will be apparent to those of skill in the art and may be targeted by the CARs of the invention in connection with alternate embodiments thereof.

"Effector function" refers to the specialized function of a differentiated cell. Effector function of a T-cell, for example, may be cytolytic activity or helper activity including the secretion of cytokines.

"Genetically modified cells", "redirected cells", "genetically engineered cells" or "modified cells" as used herein refer to cells that express the CAR of the invention.

"Immune cell" as used herein refers to the cells of the mammalian immune system including but not limited to antigen presenting cells, B-cells, basophils, cytotoxic T-cells, dendritic cells, eosinophils, granulocytes, helper T-cells, leukocytes, lymphocytes, macrophages, mast cells, memory cells, monocytes, natural killer cells, neutrophils, phagocytes, plasma cells and T-cells.

"Immune response" as used herein refers to immunities including but not limited to innate immunity, humoral immunity, cellular immunity, immunity, inflammatory response, acquired (adaptive) immunity, autoimmunity and/or overactive immunity.

"Mammal" as used herein refers to any member of the class Mammalia, including, without limitation, humans and nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus, adult and newborn subjects, as well as fetuses, whether male or female, are intended to be included within the scope of this term.

"Polynucleotide" as used herein includes but is not limited to DNA, RNA, cDNA (complementary DNA), mRNA (messenger RNA), rRNA (ribosomal RNA), shRNA (small hairpin RNA), snRNA (small nuclear RNA), snoRNA (short nucleolar RNA), miRNA (microRNA), genomic DNA, synthetic DNA, synthetic RNA, and/or tRNA.

"Naked DNA" as used herein refers to DNA encoding a CAR cloned in a suitable expression vector in proper orientation for expression. Viral vectors which may be used include but are not limited SIN lentiviral vectors, retroviral vectors, foamy virus vectors, adeno-associated virus (AAV) vectors, hybrid vectors and/or plasmid transposons (for example sleeping beauty transposon system) or integrase based vector systems. Other vectors that may be used in connection with alternate embodiments of the invention will be apparent to those of skill in the art.

"Single chain variable fragment", "single-chain antibody variable fragments" or "scFv" antibodies as used herein refer to forms of antibodies comprising the variable regions of only the heavy and light chains, connected by a linker peptide.

"Target cell" as used herein refers to cells which are involved in a disease and can be targeted by the genetically modified cells of the invention (including but not limited to genetically modified T-cells, NK cells, hematopoietic stem cells, pluripotent stem cells, and embryonic stem cells). Other target cells will be apparent to those of skill in the art and may be used in connection with alternate embodiments of the invention.

The terms "T-cell" and "T-lymphocyte" are interchangeable and used synonymously herein. Examples include but are not limited to naïve T cells, central memory T cells, effector memory T cells or combinations thereof.

"Therapeutic agents" as used herein refers to agents that are used to, for example, treat, inhibit, prevent, mitigate the effects of, reduce the severity of, reduce the likelihood of developing, slow the progression of and/or cure, a disease. Diseases targeted by the therapeutic agents include but are not limited to carcinomas, sarcomas, lymphomas, leukemia, germ cell tumors, blastomas, antigens expressed on various immune cells, and antigens expressed on cells associated with various hematologic diseases, autoimmune diseases, and/or inflammatory diseases.

"Therapeutic controls" as used herein refers to agents that regulate cell proliferation, facilitate cell selection (for example selecting cells which express the chimeric antigen receptors of the invention), facilitate cell tracking or a combination thereof. In one embodiment, regulating cell proliferation comprises up-regulating cell proliferation to promote cell propagation. In another embodiment, regulating cell proliferation comprises down-regulating cell proliferation so as to reduce or inhibit cell propagation. In some embodiments, the agents that serve as therapeutic controls may promote enrichment of cells which express the bispecific chimeric antigen receptors which may result in a therapeutic advantage.

"Transduction" as used herein refers to the introduction of a foreign nucleic acid into a cell using a viral vector.

"Transfection" as used herein refers to the introduction of a foreign nucleic acid into a cell using recombinant DNA technology. The term "transformation" means the introduction of a "foreign" (i.e. extrinsic or extracellular) gene, DNA or RNA sequence to a host cell, so that the host cell will express the introduced gene or sequence to produce a desired substance, such as a protein or enzyme coded by the introduced gene or sequence. The introduced gene or sequence may also be called a "cloned" or "foreign" gene or sequence, may include regulatory or control sequences, such as start, stop, promoter, signal, secretion, or other sequences used by a cell's genetic machinery. The gene or sequence may include nonfunctional sequences or sequences with no known function. A host cell that receives and expresses introduced DNA or RNA has been "transformed" and is a "transformant" or a "clone." The DNA or RNA introduced to a host cell can come from any source, including cells of the same genus or species as the host cell, or cells of a different genus or species "Treatment" and "treating," as used herein refer to both therapeutic treatment and prophylactic or preventative measures, wherein the object is to prevent or slow down (lessen) the targeted pathologic condition, prevent the pathologic condition, pursue or obtain beneficial results, or lower the chances of the individual developing the condition even if the treatment is ultimately unsuccessful. Those in need of treatment include those already with the condition as well as those prone to have the condition or those in whom the condition is to be prevented.

"Tumor," as used herein refers to all neoplastic cell growth and proliferation, whether malignant or benign, and all pre-cancerous and cancerous cells and tissues.

"Vector", "cloning vector" and "expression vector" as used herein refer to the vehicle by which a polynucleotide sequence (e.g. a foreign gene) can be introduced into a host cell, so as to transform the host and promote expression (e.g. transcription and translation) of the introduced sequence. Vectors include plasmids, phages, viruses, etc.

DESCRIPTION OF THE INVENTION

Chimeric Antigen Receptors

While not wishing to be limited by any one premise, it is believed that the chimeric antigen receptors (for example bispecific CARs) of the instant invention may overcome conventional therapeutic failures due to, for example, outgrowth of antigen loss escape variants that can arise in the course of various therapies when a single antigen is targeted. Accordingly, the invention is directed to, among other things, nucleic acid sequences and amino acid sequences encoding CARs, vectors comprising CARs, viruses comprising CARs, genetically modified cells comprising the CARs (redirected cells) and methods of making and using them. In some embodiments, the CARs are bispecific CARs. In other embodiments, the CARs target and bind three or more different antigens.

In general embodiments, the present invention relates to CARs (for example bispecific CARs), nucleic acid sequences encoding the CARs (for example bispecific CARs), the vectors comprising the nucleic acids encoding the CARs (for example bispecific CARs), viruses comprising the nucleic acid sequences encoding the CARs (for example bispecific CARs), host cells (such as genetically modified cells) expressing the CARs (for example bispecific CARs), combinations of CARs (for example bispecific CARs) and therapeutic controls and methods of making and using the CARs (for example bispecific CARs) as therapeutic agents.

The CARs of the invention target at least two different antigens. The CARs (such as bispecific CARs) are co-expressed with a therapeutic control; for instance, truncated epidermal growth factor receptor (EGFRt), chimeric cytokine receptors (CCR) and/or dihydroxyfolate receptor (DHFR) (e.g., mutant DHFR). The polynucleotides encoding the CAR and the therapeutic control(s) may be linked via IRES sequences or via polynucleotide sequences encoding cleavable linkers. The CARs of the invention are constructed so that they may be expressed in cells, which in turn proliferate in response to the presence of at least one molecule that interacts with at least one antigen-specific targeting region, for instance, an antigen.

In some embodiments, therapeutic controls for use with the CARs of the invention comprise any one or more of truncated epidermal growth factor receptor (EGFRt), thymidine kinase, cytosine deaminase, nitroreductase, xanthine-guanine phosphoribosyl transferase, human caspase 8, human caspase 9, purine nucleoside phosphorylase, linamarase/linamarin/glucose oxidase, deoxyribonucleoside kinase, horseradish peroxidase (HRP)/indole-3-acetic (IAA), Gamma-glutamylcysteine synthetase, CD20/alphaCD20, CD34/thymidine kinase chimera, dox-dependent caspase-2, mutant thymidine kinase (HSV-TKSR39) or AP1903/Fas system. In an embodiment, the CARs of the invention are linked to EGFRt via a cleavable linker or IRES sequences. In another embodiment, a bispecific CAR is linked to EGFRt via a cleavable linker or IRES sequences.

The CARs described herein may be synthesized as single polypeptide chains and may comprise at least two antigen-specific targeting regions, an extracellular spacer domain, a transmembrane domain, one or more co-stimulatory domains and an intracellular signaling domain. In this embodiment, the antigen-specific targeting regions are at the N-terminus, arranged in tandem and are separated by a linker peptide. The antigen-specific targeting region is linked to an extracellular spacer domain which is linked to the transmembrane domain. The transmembrane domain is linked to the co-stimulatory domain. The co-stimulatory domain is linked to the intracellular signaling domain which is at the C-terminus. If more than one co-stimulatory domain is used, the multiple co-stimulatory domains may be arranged in tandem with the transmembrane domain at its N-terminus and the intracellular signaling domain at its C-terminus. Polynucleotides encoding these polypeptides may further comprise an N-terminal signal sequence which directs the CAR to the cell surface as a type I transmembrane protein. The antigen-specific targeting region may be extracellular-facing and the intracellular signaling domain may be cytoplasmic.

FIG. 1 shows a schematic of a chimeric antigen receptor of the invention.

In an embodiment, an extracellular spacer domain in the CAR is optional. In such a CAR, the antigen-specific targeting regions are at the N-terminus, arranged in tandem, and separated by a linker peptide. The antigen-specific targeting region may be linked to the transmembrane domain. The transmembrane domain may be linked to the co-stimulatory domain. The co-stimulatory domain may be linked to the intracellular signaling domain, which is at the C-terminus. If more than one co-stimulatory domain is used, the multiple co-stimulatory domains may be arranged in tandem with the transmembrane domain at its N-terminus and the intracellular signaling domain at its C-terminus. Polynucleotides encoding these polypeptides may further comprise an N-terminal signal sequence which directs the CAR to the cell surface as a type I transmembrane protein. The antigen-specific targeting region may be extracellular-facing and the intracellular signaling domain may be cytoplasmic.

Antigen-Specific Targeting Regions of Chimeric Antigen Receptors

The CARs of the invention may target several (such as two or more, three or more) different antigens. In an embodiment, the CAR is a bispecific CAR and targets two different antigens. As described above, the antigen-specific targeting regions of the CAR may be arranged in tandem and may be separated by linker peptides. The antigens targeted by the CAR may be antigens on single diseased cell (such as a cancerous B-cell) or antigens that are expressed on separate cells that each contribute to the disease. The antigens targeted by the CAR are antigens which are either directly or indirectly involved in the disease.

In a bispecific CAR, at least two different antigen-specific antibodies or fragments thereof or derivatives thereof may be cloned into the antigen-specific targeting region. The antibodies may be specific for any, but at least two, distinct antigens of choice. The antibody specific to the antigen may be the Fab fragment of the antibody or the single chain variable fragment (scFv) of the antibody.

For example, FIGS. 2A and 2B show an embodiment of the invention depicting a CAR specific to CD19 and CD20. Using methods well known to one skilled in the art, scFvs specific to multiple, but at least two different antigens, may be cloned upstream (i.e., to N-terminus) of the IgG4-CD28-zeta domains so long as the target-antigens are expressed on cells that are targetable by the genetically modified cells described below. Such techniques are explained fully in the literature. (Sambrook et al, "Molecular Cloning: A Laboratory Manual" (1989), Current Protocols in Molecular Biology. Volumes I-III [Ausubel, R. M., ed. (1994)], Cell Biology: A Laboratory Handbook. Volumes I-III [J. E. Celis, ed. (1994))], Current Protocols in Immunology. Volumes I-III [Coligan, J. E., ed. (1994)], Oligonucleotide Synthesis. (M. J. Gait ed. 1984), Nucleic Acid Hybridization [B. D. Hames & S. J. Higgins eds. (1985)], Transcription And Translation [B. D. Hames & S. J. Higgins, eds. (1984)], Animal Cell Culture [R. I. Freshney, ed. (1986)], Immobilized Cells And Enzymes [IRL Press, (1986)], Practical Guide To Molecular Cloning B. Perbal (1984), Current Prptocols in Immunology (J. E. Coligan, A. M. Kruisbeek, D. H. Margulies, E. M. Shevach and W. Strober, eds., 1991), Annual Review of Immunology as well as monographs in journals such as Advances in Immunology).

In one embodiment, each antigen-specific targeting region comprises the full-length IgG heavy chain (specific for the target antigen) having the $V_H$, CH1, hinge, and the CH2 and CH3 (Fc) Ig domains, if the $V_H$ domain alone is sufficient to confer antigen-specificity ("single-domain antibodies"). The full length IgG heavy chain may be linked to the co-stimulatory domain and the intracellular signaling domain via the appropriate transmembrane domain. If both, the $V_H$ and the $V_L$ domains, are necessary to generate a fully active antigen-specific targeting region, the $V_H$-containing CAR and the full-length lambda light chain (IgL) are both introduced into the cells to generate an active antigen-specific targeting region. In an embodiment, an extracellular spacer domain may be linked between the antigen-specific binding domain and the transmembrane domain. The cells include but are not limited to T-lymphocytes (T-cells), natural killer cells, hematopoietic stem cells and/or pluripotent embryonic/induced stem cells capable of giving rise to therapeutically relevant progeny.

In another embodiment, each antigen-specific targeting region of the CAR comprises at least two single chain antibody variable fragments (scFv), each specific for a different target antigen. scFvs, in which the C-terminus of one variable domain ($V_H$ or $V_L$) is tethered to the N-terminus of the other ($V_L$ or $V_H$, respectively) via a polypeptide linker, have been developed without significantly disrupting antigen binding or specificity of the binding. (Chaudhary et al., A recombinant single-chain immunotoxin composed of anti-Tac variable regions and a truncated diphtheria toxin. 1990 Proc. Natl. Acad. Sci., 87:9491; Bedzyk et al. Immunological and structural characterization of a high affinity anti-fluorescein single-chain antibody. 1990 J. Biol. Chem., 265: 18615). The linker connects the N-terminus of the $V_H$ with the C-terminus of $V_L$ or the C-terminus of $V_H$ with the N-terminus of $V_L$. These scFvs lack the constant regions (Fc) present in the heavy and light chains of the native antibody. The scFvs, specific for at least two different antigens, are arranged in tandem and linked to the co-stimulatory domain and the intracellular signaling domain via a transmembrane domain. In an embodiment, an extracellular spacer domain may be linked between the antigen-specific binding region and the transmembrane domain.

In another aspect, each scFv fragment may be fused to all or a portion of the constant domains of the heavy chain. The resulting antigen-specific targeting region, specific for at least two different antigens, is joined to the co-stimulatory domain and the intracellular signaling domain via a transmembrane domain. In an embodiment, an extracellular spacer domain may be linked between the antigen-specific binding domain and the transmembrane domain.

In a further embodiment, each antigen-specific targeting region of the CAR comprises a divalent (or bivalent) single-chain variable fragment (di-scFvs, bi-scFvs). In CARs comprising di-scFVs, two scFvs specific for each antigen are linked together by producing a single peptide chain with two $V_H$ and two $V_L$ regions, yielding tandem scFvs. (Xiong, Cheng-Yi; Natarajan, A; Shi, X B; Denardo, G L; Denardo, S J (2006). "Development of tumor targeting anti-MUC-1 multimer: effects of di-scFv unpaired cysteine location on PEGylation and tumor binding". *Protein Engineering Design and Selection* 19 (8): 359-367; Kufer, Peter; Lutterbüse, Ralf; Baeuerle, Patrick A. (2004). "A revival of bispecific antibodies". *Trends in Biotechnology* 22 (5): 238-244). CARs comprising at least two antigen-specific targeting regions would express two scFvs specific for each of the two antigens. The resulting antigen-specific targeting region, specific for at least two different antigens, is joined to the co-stimulatory domain and the intracellular signaling domain via a transmembrane domain. In an embodiment, an extracellular spacer domain may be linked between the antigen-specific binding domain and the transmembrane domain.

In an additional embodiment, each antigen-specific targeting region of the CAR comprises a diabody. In a diabody, the scFvs are created with linker peptides that are too short for the two variable regions to fold together, driving the scFvs to dimerize. Still shorter linkers (one or two amino acids) lead to the formation of trimers, the so-called triabodies or tribodies. Tetrabodies may also be used.

To create the CARs of the present invention, two or more individual antigen-specific targeting regions are connected to each other, either covalently or noncovalently, on a single protein molecule. An oligo- or polypeptide linker, an Fc hinge or membrane hinge region may be used to connect these domains to each other. The CARs of the present invention may comprise two or more of the different antigen-specific targeting regions connected together in different combinations. For example, two or more antigen-specific targeting regions containing immunoglobulin sequences (e.g. scFvs and/or single-domain antibodies) may be linked to each other.

Targets of Antigen-Specific Targeting Regions of Chimeric Antigen Receptors

In some embodiments, the antigen-specific targeting region of the CAR (for example bispecific CAR) targets antigens specific for cancer, inflammatory disease, neuronal-disorders, diabetes, cardiovascular disease, infectious diseases or a combination thereof. Examples of antigens which may be targeted by the CARs (for example bispecific CARs) of the invention include but are not limited to antigens expressed on B-cells, antigens expressed on carcinomas, sarcomas, lymphomas, leukemia, germ cell tumors, blastomas, antigens expressed on various immune cells, and antigens expressed on cells associated with various hematologic diseases, autoimmune diseases, and/or inflammatory diseases. The CARs of the invention, which are specific for at least two different target antigens, may be capable of redirecting the effector function of the expressing-cells to either of both of the target antigens. This feature of the construct may overcome the issue of antigen loss escape variants when targeting, for example, genetically unstable B-cell lineage malignancies using single antigen-specificity.

Antigens specific for cancer which may be targeted by the CARs (for example bispecific CARs) of the invention include but are not limited to any one or more of 4-1BB, 5T4, adenocarcinoma antigen, alpha-fetoprotein, BAFF, B-lymphoma cell, C242 antigen, CA-125, carbonic anhydrase 9 (CA-IX), C-MET, CCR4, CD152, CD19, CD20, CD200, CD22, CD221, CD23 (IgE receptor), CD28, CD30 (TNFRSF8), CD33, CD4, CD40, CD44 v6, CD51, CD52, CD56, CD74, CD80, CEA, CNTO888, CTLA-4, DR5, EGFR, EpCAM, CD3, FAP, fibronectin extra domain-B, folate receptor 1, GD2, GD3 ganglioside, glycoprotein 75, GPNMB, HER2/neu, HGF, human scatter factor receptor kinase, IGF-1 receptor, IGF-I, IgG1, L1-CAM, IL-13, IL-6, insulin-like growth factor I receptor, integrin α5β1, integrin αvβ3, MORAb-009, MS4A1, MUC1, mucin CanAg, N-glycolylneuraminic acid, NPC-1C, PDGF-R α, PDL192, phosphatidylserine, prostatic carcinoma cells, RANKL, RON, ROR1, SCH 900105, SDC1, SLAMF7, TAG-72, tenascin C, TGF beta 2, TGF-β, TRAIL-R1, TRAIL-R2, tumor antigen CTAA16.88, VEGF-A, VEGFR-1, VEGFR2 or vimentin. Other antigens specific for cancer will be apparent to those of skill in the art and may be used in connection with alternate embodiments of the invention. Examples of CARs which target the above antigens include but are not limited to bispecific CARs, bispecific CARs co-expressed with EGFRt, bispecific CARs co-expressed with EGFRt and CCR, bispecific CARs co-expressed with EGFRt and DHFR (for example mutant DHFR) or bispecific CARs co-expressed with EGFRt and CDR and DHFR (for example mutant DHFR).

In some embodiments, the bispecific chimeric antigen receptors target and bind at least two different antigens. Examples of pairings of at least two antigens bound by the bispecific CARs of the invention include but are not limited to CD19 and CD20, CD19 and CD22, CD20 and L1-CAM, L1-CAM and GD2, EGFR and L1-CAM, EGFR and C-MET, EGFR and HER2, C-MET and HER2 and EGFR and ROR1. Other pairings of antigens specific for cancer will be apparent to those of skill in the art and may be used in connection with alternate embodiments of the invention. In yet other embodiments, the bispecific chimeric antigen receptor targets CD19 and CD20. Examples of CARs which target the above antigens include but are not limited to bispecific CARs, bispecific CARs co-expressed with EGFRt, bispecific CARs co-expressed with EGFRt and CCR, bispecific CARs co-expressed with EGFRt and DHFR (for example mutant DHFR) or bispecific CARs co-expressed with EGFRt and CDR and DHFR (for example mutant DHFR).

Antigens specific for inflammatory diseases which may be targeted by the CARs of the invention include but are not limited to any one or more of AOC3 (VAP-1), CAM-3001, CCL11 (eotaxin-1), CD125, CD147 (basigin), CD154 (CD40L), CD2, CD20, CD23 (IgE receptor), CD25 (α chain of IL-2 receptor), CD3, CD4, CD5, IFN-α, IFN-γ, IgE, IgE Fc region, IL-1, IL-12, IL-23, IL-13, IL-17, IL-17A, IL-22, IL-4, IL-5, IL-5, IL-6, IL-6 receptor, integrin α4, integrin α4β7, *Lama glama*, LFA-1 (CD11a), MEDI-528, myostatin, OX-40, rhuMAb β7, scleroscin, SOST, TGF beta 1, TNF-α or VEGF-A. Other antigens specific for inflammatory diseases will be apparent to those of skill in the art and may be used in connection with alternate embodiments of the invention. Examples of CARs which target the above antigens include but are not limited to bispecific CARs, bispecific CARs co-expressed with EGFRt, bispecific CARs co-expressed with EGFRt and CCR, bispecific CARs co-expressed with EGFRt and DHFR (for example mutant DHFR) or bispecific CARs co-expressed with EGFRt and CDR and DHFR (for example mutant DHFR).

Antigens specific for neuronal disorders which may be targeted by the CARs of the invention include but are not limited to any one or more of beta amyloid or MABT5102A. Other antigens specific for neuronal disorders will be apparent to those of skill in the art and may be used in connection with alternate embodiments of the invention. Examples of CARs which target the above antigens include but are not limited to bispecific CARs, bispecific CARs co-expressed with EGFRt, bispecific CARs co-expressed with EGFRt and CCR, bispecific CARs co-expressed with EGFRt and DHFR (for example mutant DHFR) or bispecific CARs co-expressed with EGFRt and CDR and DHFR (for example mutant DHFR).

Antigens specific for diabetes which may be targeted by the CARs of the invention include but are not limited to any one or more of L-1β or CD3. Other antigens specific for diabetes or other metabolic disorders will be apparent to those of skill in the art and may be used in connection with alternate embodiments of the invention. Examples of CARs which target the above antigens include but are not limited to bispecific CARs, bispecific CARs co-expressed with EGFRt, bispecific CARs co-expressed with EGFRt and CCR, bispecific CARs co-expressed with EGFRt and DHFR (for example mutant DHFR) or bispecific CARs co-expressed with EGFRt and CDR and DHFR (for example mutant DHFR).

Antigens specific for cardiovascular diseases which may be targeted by the CARs of the invention include but are not limited to any one or more of C5, cardiac myosin, CD41 (integrin alpha-IIb), fibrin II, beta chain, ITGB2 (CD18) and sphingosine-1-phosphate. Other antigens specific for cardiovascular diseases will be apparent to those of skill in the art and may be used in connection with alternate embodiments of the invention. Examples of CARs which target the above antigens include but are not limited to bispecific CARs, bispecific CARs co-expressed with EGFRt, bispecific CARs co-expressed with EGFRt and CCR, bispecific CARs co-expressed with EGFRt and DHFR (for example mutant DHFR) or bispecific CARs co-expressed with EGFRt and CDR and DHFR (for example mutant DHFR).

Antigens specific for infectious diseases which may be targeted by the CARs of the invention include but are not limited to any one or more of anthrax toxin, CCR5, CD4, clumping factor A, cytomegalovirus, cytomegalovirus glycoprotein B, endotoxin, *Escherichia coli*, hepatitis B surface antigen, hepatitis B virus, HIV-1, Hsp90, Influenza A hemagglutinin, lipoteichoic acid, *Pseudomonas aeruginosa*, rabies virus glycoprotein, respiratory syncytial virus and TNF-α. Other antigens specific for infectious diseases will be apparent to those of skill in the art and may be used in connection with alternate embodiments of the invention. Examples of CARs which target the above antigens include but are not limited to bispecific CARs, bispecific CARs co-expressed with EGFRt, bispecific CARs co-expressed with EGFRt and CCR, bispecific CARs co-expressed with EGFRt and DHFR (for example mutant DHFR) or bispecific CARs co-expressed with EGFRt and CDR and DHFR (for example mutant DHFR).

Further examples of target antigens include but are not limited to surface proteins found on cancer cells in a specific or amplified fashion (e.g. the IL-14 receptor, CD19, CD20 and CD40 for B-cell lymphoma, the Lewis Y and CEA antigens for a variety of carcinomas, the Tag72 antigen for breast and colorectal cancer, EGF-R for lung cancer, folate binding protein and the HER-2 protein which is often amplified in human breast and ovarian carcinomas), or viral proteins (e.g. gp120 and gp41 envelope proteins of HIV, envelope proteins from the Hepatitis B and C viruses, the glycoprotein B and other envelope glycoproteins of human cytomegalovirus, the envelope proteins from oncoviruses such as Kaposi's sarcoma-associated Herpes virus). Other potential targets of the CARs of the invention include CD4, where the ligand is the HIV gp120 envelope glycoprotein, and other viral receptors, for example ICAM, which is the receptor for the human rhinovirus, and the related receptor molecule for poliovirus.

Additional targets of the CARs of the invention include antigens involved in B-cell associated diseases. Yet further targets of the CARs of the invention will be apparent to those of skill in the art and may be used in connection with alternate embodiments of the invention.

Co-Stimulatory Domains of Chimeric Antigen Receptors

The CARs of the invention may also comprise a co-stimulatory domain. This domain may enhance cell proliferation, cell survival and development of memory cells. The CARs of the invention may comprise one or more co-stimulatory domains. Each co-stimulatory domain comprises the co-stimulatory domain of any one or more of, for example, members of the TNFR super family, CD28, CD137 (4-1BB), CD134 (OX40), Dap10, CD27, CD2, CD5, ICAM-1, LFA-1, Lck, TNFR-1, TNFR-II, Fas, CD30, CD40 or combinations thereof. Co-stimulatory domains from other proteins may also be used with the CARs of the invention.

Additional co-stimulatory domains will be apparent to those of skill in the art and may be used in connection with alternate embodiments of the invention. If a CAR comprises more than one co-stimulatory domain, these domains may be arranged in tandem, optionally separated by a linker.

Extracellular Spacer Domain of Chimeric Antigen Receptor

The CARs of the invention may further comprise an extracellular spacer domain. In some embodiments, this domain facilitates proper protein folding. The extracellular spacer domain comprises a hydrophilic region which is attached to the antigen-specific targeting region and the transmembrane domain. Extracellular spacer domains may include, but are not limited to, Fc fragments of antibodies or fragments or derivatives thereof, hinge regions of antibodies or fragments or derivatives thereof, CH2 regions of antibodies, CH3 regions antibodies, artificial spacer sequences or combinations thereof. Examples of extracellular spacer domains include but are not limited to CD8α hinge, artificial spacers made of polypeptides such as Gly3, or CH1, CH3 domains of IgG's (such as human IgG4). Specifically, the extracellular spacer domain may be (i) a hinge, CH2 and CH3 regions of IgG4, (ii) a hinge region of IgG4, (iii) a hinge and CH2 of IgG4, (iv) a hinge region of CD8α, (v) a hinge, CH2 and CH3 regions of IgG1, (vi) a hinge region of IgG1 or (vi) a hinge and CH2 of IgG1 or a combination thereof. Additional extracellular spacer domains will be apparent to those of skill in the art and may be used in connection with alternate embodiments of the invention.

Transmembrane Domain of Chimeric Antigen Receptors

The CARs of the invention may also comprise a transmembrane domain. The transmembrane domain may comprise the transmembrane sequence from any protein which has a transmembrane domain, including any of the type I, type II or type III transmembrane proteins. The transmembrane domain of the CAR of the invention may also comprise an artificial hydrophobic sequence. The transmembrane domains of the CARs of the invention may be selected so as not to dimerize. Additional transmembrane domains will be apparent to those of skill in the art and may be used in connection with alternate embodiments of the invention.

Intracellular Signaling Domain of Chimeric Antigen Receptors

The CARs of the invention may also comprise an intracellular signaling domain. This domain may be cytoplasmic and may transduce the effector function signal and direct the cell to perform its specialized function. Examples of intracellular signaling domains include, but are not limited to, ζ chain of the T-cell receptor or any of its homologs (e.g., η chain, FcεR1γ and β chains, MB1 (Igα) chain, B29 (Igβ) chain, etc.), CD3 polypeptides (Δ, δ and ε), syk family tyrosine kinases (Syk, ZAP 70, etc.), src family tyrosine kinases (Lck, Fyn, Lyn, etc.) and other molecules involved in T-cell transduction, such as CD2, CD5 and CD28. Specifically, the intracellular signaling domain may be human CD3 zeta chain, FcγRIII, FcεRI, cytoplasmic tails of Fc receptors, immunoreceptor tyrosine-based activation motif (ITAM) bearing cytoplasmic receptors or combinations thereof. Additional intracellular signaling domains will be apparent to those of skill in the art and may be used in connection with alternate embodiments of the invention.

Linkers in Chimeric Antigen Receptors

In some embodiments, two or more components of the CARs of the invention are separated by one or more linkers. For example, in CARs comprising at least two antigen-specific targeting regions, the first targeting region on the CAR may be separated from the second targeting region on the CAR via a linker. Additionally, the CAR may be linked to therapeutic controls via a linker. Linkers are oligo- or polypeptides region from about 1 to 100 amino acids in length, that link together any of the domains/regions of the CAR of the invention. In some embodiments, the linkers may be for example, 5-12 amino acids in length, 5-15 amino acids in length or 5 to 20 amino acids in length. Linkers may be composed of flexible residues like glycine and serine so that the adjacent protein domains are free to move relative to one another. Longer linkers, for example those longer than 100 amino acids, may be used in connection with alternate embodiments of the invention, and may be selected to, for example, ensure that two adjacent domains do not sterically interfere with one another. Examples of linkers which may be used in the instant invention include but are not limited to 2A linkers (for example T2A), 2A-like linkers or functional equivalents thereof.

Therapeutic Controls

Therapeutic controls regulate cell proliferation, facilitate cell selection (for example selecting cells which express the chimeric antigen receptors of the invention) or a combination thereof. In one embodiment, regulating cell proliferation comprises up-regulating cell proliferation to promote cell propagation. In another embodiment, regulating cell proliferation comprises down-regulating cell proliferation so as to reduce or inhibit cell propagation. In some embodiments, the agents that serve as therapeutic controls may promote enrichment of cells which express the bispecific chimeric antigen receptors which may result in a therapeutic advantage. In some embodiments, agents which serve as therapeutic controls may biochemically interact with additional compositions so as to regulate the functioning of the therapeutic controls. For example, EGFRt (a therapeutic control) may biochemically interact with cetuximab so as to regulate the function of EGFRt in selection, tracking, cell ablation or a combination thereof.

Examples of therapeutic controls include but are not limited to any one or more of truncated epidermal growth factor receptor (EGFRt), thymidine kinase, cytosine deaminase, nitroreductase, xanthine-guanine phosphoribosyl transferase, human caspase 8, human caspase 9, purine nucleoside phosphorylase, linamarase/linamarin/glucose oxidase, deoxyribonucleoside kinase, horseradish peroxidase (HRP)/indole-3-acetic (IAA), Gamma-glutamylcysteine synthetase, CD20/alphaCD20, CD34/thymidine kinase chimera, dox-dependent caspase-2, mutant thymidine kinase (HSV-TKSR39), AP1903/Fas system, a chimeric cytokine receptor (CCR), a selection marker, and combinations thereof. In some embodiments, the therapeutic controls are co-expressed with the bispecific chimeric antigen receptor.

Examples of agents which regulate the functioning of the therapeutic controls include but are not limited to any one or more of HERCEPTIN®, methotrexate, cetuximab, thymidine analogs (for example ganciclovir), (E)-5-(2-bromovinyl)-2'-deoxyuridine (BVDU), 5-fluorocytosine (5-FC), 5-(azaridin-1-yl)-2,4-dinitrobenzamide (CB1954), 6-thioguanine, a synthetic dimerizing drug (for example AP1903), fludarabine phosphate, linamarin (lin), nucleoside analogs (for example BVDU, difluorodeoxycytidine (dFdC), 1-β-D-arabinofuranosylthymine (ara-T)), indole-3-acetic (IAA), 1-buthionine-S,R-sulfoximine (BSO), rituximab (RTX), doxycycline, tyrosine kinase inhibitors or combinations thereof. These agents may be administered before, during or after the use of the therapeutic controls.

As described above, the CARs of the invention may be synthesized as single polypeptide chains. If the CAR is a bispecific CAR, the polynucleotide sequence encoding the CAR may be, for example, in the following configuration in the N-terminal to C-terminal direction: N-terminal signal sequence-antigen-specific targeting region 1-linker-antigen-specific targeting region 2-extracellular spacer domain-transmembrane domain-co-stimulatory domain-intracellular signaling domain. In an embodiment, such a CAR may comprise two or more co-stimulatory domains.

Alternatively, the polynucleotide sequence encoding the CAR may be in the following configuration in the N-terminal to C-terminal direction: N-terminal signal sequence-antigen-specific targeting region 1-linker-antigen-specific targeting region 2-transmembrane domain-co-stimulatory domain-intracellular signaling domain. In an embodiment, such a CAR may comprise two or more co-stimulatory domains.

If a CAR comprises more than two antigen-specific targeting regions, the polynucleotide sequence encoding the CAR may be in the following configuration in the N-terminal to C-terminal direction: N-terminal signal sequence-antigen-specific targeting region 1-linker-antigen-specific targeting region 2-linker-(antigen-specific targeting region)$_n$-transmembrane domain-co-stimulatory domain-intracellular signaling domain. Such a CAR may further comprise an extracellular spacer domain. Each antigen-specific targeting region may be separated by a linker. In an embodiment, such a CAR may comprise two or more co-stimulatory domains.

The invention provides a nucleic acid sequence of the backbone of an exemplary CAR of the invention comprising an extracellular spacer domain, a transmembrane domain, a co-stimulatory domain and an intracellular signaling domain. Specifically, an exemplary backbone for a may CAR comprise, in the N-terminus to C-terminus orientation, IgG4hinge-CD28tm-41BB-CD3zeta, wherein the extracellular spacer domain is the IgG4 hinge region, the transmembrane domain is the transmembrane region from CD28, the co-stimulatory domain is from 4-1BB and the intracellular signaling domain is from the CD3 zeta chain (FIG. 7). At least two or more antigen-specific targeting regions may be inserted N-terminal to the IgG4 hinge.

The invention provides nucleic acid sequences of an exemplary embodiment of the invention where the CAR is specific to CD19 and CD20. In one embodiment, the sequence encoding a bispecific anti-CD19×CD20 CAR is set forth in FIG. 3, FIG. 8 or FIG. 10. In another embodiment, the sequence encoding a bispecific anti-CD19×CD20 CAR is set forth in FIG. 4A-4C, FIG. 9A-9D or FIG. 11A-11D. In this exemplary embodiment, the bispecific CAR comprises scFvs specific for CD19 and CD20 with each scFv separated by a linker, joined to an extracellular spacer domain, which is joined to the co-stimulatory and intracellular signaling domains via a transmembrane domain. Although the exemplary CAR depicts a set of scFv sequences, any scFv specific for CD19 and CD20 may be used. In a particular embodiment, the bispecific CAR specific for CD19 and CD20 is CD19scFv-Gly4Serlinker-CD20scFv-IgG4-Hinge-CD28tm-41BB(cyto)-zeta(cyto) and is encoded by the sequences set forth in FIG. 3 and FIG. 4A-4C. This bispecific CAR comprises single chain Fv fragments specific for CD19 and CD20 linked by a Gly4Ser linker, an IgG4 hinge extracellular spacer domain, a CD28 transmembrane domain, a 41BB costimulatory domain and the cytoplasmic domain from CD3 zeta chain.

In another embodiment, the bispecific CAR specific for CD19 and CD20 comprises CD19scFv-Gly4serlinker-CD20scFv-huIgG4-hingeCH2CH3-CD28tm/cyto-41BB-zeta (FIGS. 9A-9D and FIG. 10). This bispecific CAR comprises single chain Fv fragments specific for CD19 and CD20 linked by a Gly4Ser linker, a human IgG4 hinge, CH2 and CH3 extracellular spacer domain, a CD28 transmembrane domain, a 4-1BB costimulatory domain and the cytoplasmic domain from CD3 zeta chain.

In a further embodiment, the bispecific CAR specific for CD19 and CD20 is CD19-Gly4serlinker-CD20scFv-CD8αhinge-CD8αTM-41BBcostim-zetacyto (FIGS. 11A-11D and FIG. 12). This bispecific CAR comprises single chain Fv fragments specific for CD19 and CD20 linked by a Gly4Ser linker, a CD8alpha hinge extracellular spacer domain, a CD8alpha transmembrane domain, a 41BB costimulatory domain and the cytoplasmic domain from CD3 zeta chain.

Truncated Epidermal Growth Factor Receptor (EGFRt)

Human epidermal growth factor receptor (huEGFR) (EGFR; ErbB-1, HER1 in humans) is a receptor tyrosine kinase of the ErbB family of growth factor receptors that is not expressed by cells of the hematopoietic and lymphopoietic systems. Ligand (EGF, TGF-α) binding occurs within N-terminal extracellular domains I and II of EGFR resulting from transition of receptor tyrosine kinase inactive monomers to active homodimers.

Extracellular domain III of EGFR contains the binding sites of antibodies (for example cetuximab (ERBITUX®), an IgG1 chimeric antibody). It is believed that human EGFR may be rendered incapable of binding ligands (EGF, TGF-α) by removal of domains I and II, and devoid of signaling activity by deletion of its cytoplasmic tail, while retaining an intact antibody binding site (for example cetuximab binding site), for example in extracellular domain III, IV or a combination thereof (Wang et al., A transgene-encoded cell surface polypeptide for selection, in vivo tracking, and ablation of engineered cells *Blood* 118(5)1255-1263).

A truncated EGFRt polypeptide described herein has at least three uses for genetic engineering of cell-based therapies: ex vivo cell purification, in vivo cell tracking, and cell ablation. In an embodiment, EGFRt, for use as a therapeutic control with the CARs of the invention, binds any one or more of EGFR-specific siRNA, a small molecule that targets EGFR, an anti-EGFR-antibody or a combination thereof. In another embodiment, EGFRt comprises the sequence set forth in FIG. 12 or FIG. 13A-13B or sequences that are about 70%, about 75%, about 80%, about 85%, about 90% or about 95% homologous to the sequences set forth in FIG. 12 or FIG. 13A-13B.

In an embodiment of the invention, huEGFRt may be co-expressed with the CARs of the invention so as to purify cells expressing the CARs (for example ex vivo cell purification), track cells (for example in vitro or in vivo cell tracking) expressing the CARs or regulate cells (for example in vivo or in vitro or ex vivo) expressing the CARs by triggering cell ablation as required. In one embodiment, the CARs are bispecific CARs.

Chimeric Cytokine Receptor (CCR)

Based on the limitations of using exogenous γc cytokines in adoptive immunotherapy, the invention provides T cells with an intrinsic γc cytokine signaling mechanism. The utility of forced constitutive chimeric cytokine receptors IL-2/IL-15Rβ (CγCR2) and IL-7Rα (CγCR7) receptor signals were compared. As described below, the chimeric cytokine receptors have the ability to improve the survival, persistence, and in vivo engraftment of cytotoxic T cells (CTLs).

Accordingly, in an embodiment of the invention, the CARs of the invention may be co-expressed with CCR. For example, a bispecific CAR may be co-expressed with EGFRt and CCR. Alternately, a bispecific CAR may be co-expressed with CCR. Examples of chimeric cytokine receptor include but are not limited to IL-7 cytokine-linker-IL7Rα, IL-7 cytokine-linker-extracellular domain of IL-7Rα-transmembrane domain of IL-7Rα-cytoplasmic domain of IL-2Rβ, IL-7 cytokine-linker-IL2Rβ.

A CCR comprising IL-7 cytokine-linker-IL7Rα comprises an N-terminal signal sequence joined to the N-terminus of the IL-7 cytokine which is linked via a linker to extracellular, transmembrane and cytoplasmic domains of IL-7Rα (the alpha chain of the IL-7 receptor).

A CCR comprising IL-7 cytokine-linker-extracellular domain of IL-7Rα-transmembrane domain of IL-7Rα-cytoplasmic domain of IL-2Rβ comprises an N-terminal signal sequence joined to the N-terminus of the IL-7 cytokine which is linked via a linker to the extracellular domain and transmembrane domain of IL-7Rα and to the cytoplasmic domain of IL-2Rβ (the beta chain of the IL-2 receptor).

A CCR comprising IL-7 cytokine-linker-IL2Rβ comprises N-terminal signal sequence joined to the N-terminus of the IL-7 cytokine which is linked via a linker to extracellular, transmembrane and cytoplasmic domains of IL-2Rβ.

Dihydroxyfolate Receptor (DHFR)

Genetic modification of T cells to co-express a therapeutic transgene and a drug resistant transgene that confers resistance to lymphotoxic drugs provides the opportunity to select for therapeutic cells both in vivo and ex vivo. A mutated human enzyme transgene, dihydrofolate reductase double mutant (DHFR$^{FS}$; L22F, F31S), which confers resistance of engineered T cells to methotrexate (MTX), allowing selection of cells co-expressing a CD19-specific chimeric antigen receptor (CD19CAR) that specifically targets B-lineage tumor cells.

In an embodiment, the CARs of the invention (for example bispecific CARs) may be co-expressed with DHFR (for example mutant DHFR). In a further embodiment, the bispecific CAR may be co-expressed with EGFRt, CCR and DHFR (including mutant DHFR).

Alternately, the bispecific CAR may be co-expressed with EGFRt and DHFR (including mutant DHFR).

Other selection markers that may be used with the CARs of the invention include but are not limited to methylated-DNA-protein-cysteine methyltransferase (MDMT), inosine monophosphate dehydrogenase II (IMDHP2) or a combination thereof. MDMT makes cells resistant to chemotherapy and therefore may be used if synergy between chemotherapy and T cell therapy is desired.

Vectors encoding the CARs of the invention are also provided herein. Vectors encoding CARs also encode EGFRt. In some embodiments, vectors encoding CARs and EGFRt also encode CCR or DHFR (for example mutant DHFR). In other embodiments, vectors encoding CARs and EGFRt also encode CCD and DHFR (for example mutant DHFR). In some specific embodiments, the vectors may encode a bispecific CAR and EGFRt, a bispecific CAR and EGFRt and CCR, a bispecific CAR and EGFRt and DHFR (for example mutant DHFR) or a bispecific CAR and EGFRt and CCR and DHFR (for example mutant DHFR). Vectors which may be used to express the CARs of the invention include but are not limited to lentivirus vectors, gamma retrovirus vectors, foamy virus vectors, AAV vectors, adeno virus vectors, engineered hybrid viruses, naked DNA (including but not limited to transposon mediated vectors, such as Sleeping Beauty, Piggybak, and Integrases such as Phi31.

Figure 5:
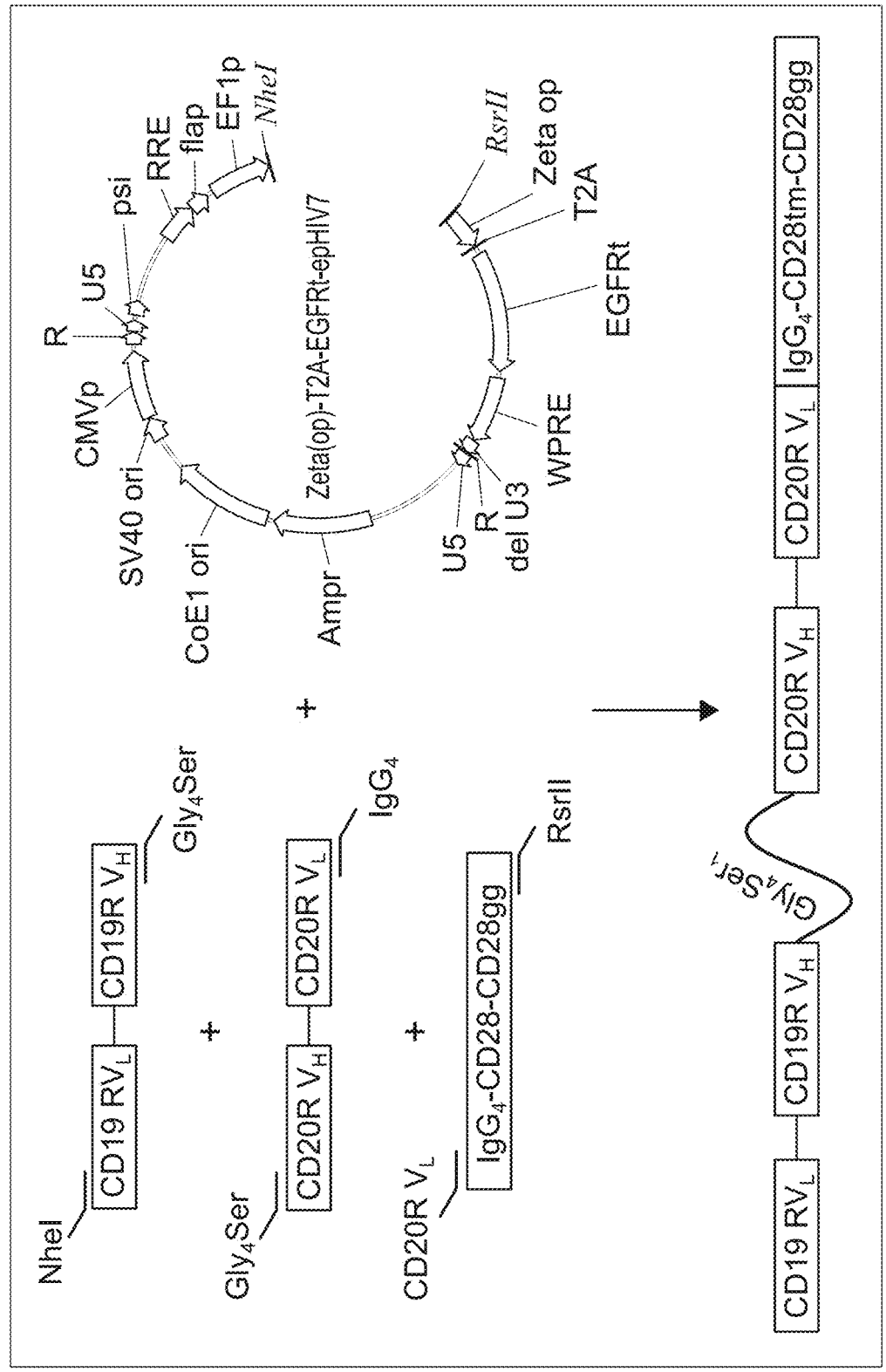
FIG. 5 depicts, in accordance with an embodiment of the present invention, a CD19scFv-Gly4Ser1linker-CD20scFv-IgG4hinge-CD28tm-CD28gg-CD3Zeta transgene construct.
Figure 6A:
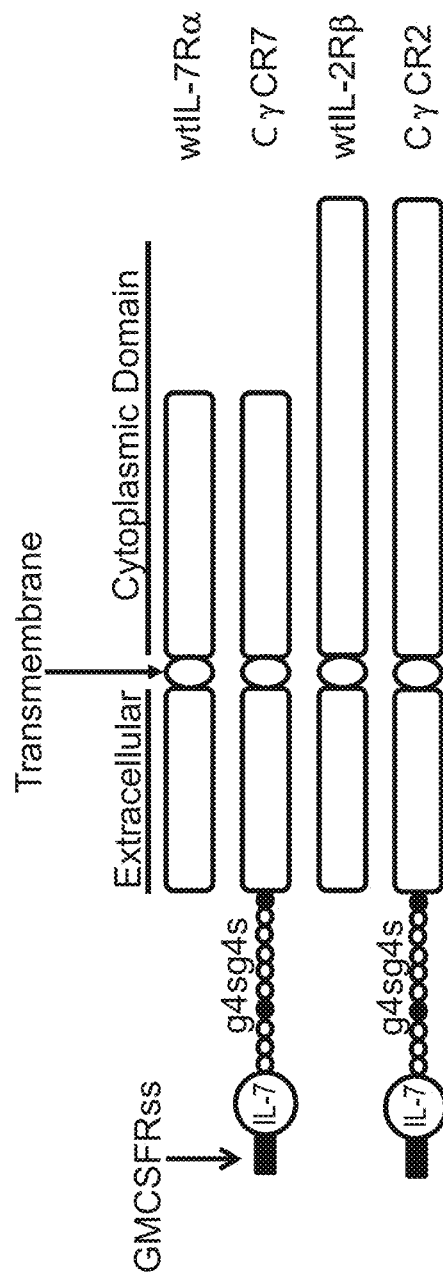
FIGS. 6A and 6B depict, in accordance with an embodiment of the present invention, development of a CγCR platform to support exogenous γc independent growth.
Figure 6B:
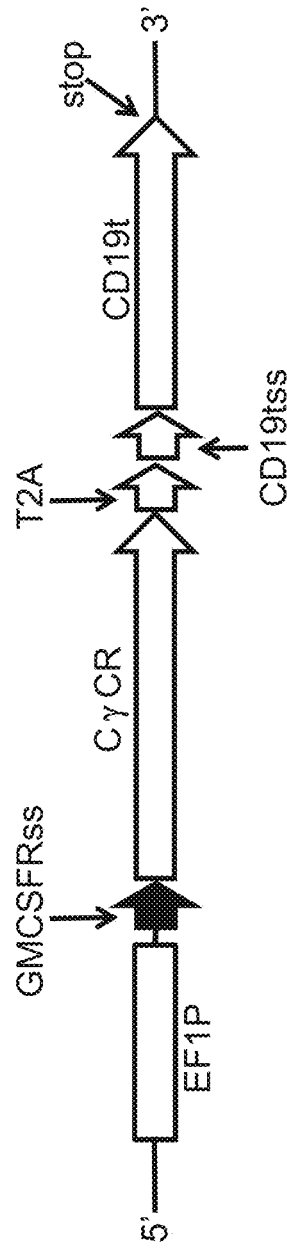

In an exemplary embodiment of the invention, the bispecific CAR specific to CD19 and CD20 disclosed herein is expressed via a lentiviral vector as illustrated in FIG. 5.

Genetically Engineered Cells of the Invention

The invention also provides genetically engineered cells which comprise and stably express the CAR of the invention. The CAR expressed by the genetically engineered cell may comprise at least two antigen-specific targeting regions, an extracellular domain, a transmembrane domain, one or more co-stimulatory domains and an intracellular signaling domain. The polynucleotide sequence encoding the CAR may also comprise an N-terminal signal sequence. In an embodiment, the CAR is a bispecific CAR. Each of the at least two antigen-specific targeting regions, extracellular spacer domain, transmembrane domain, one or more co-stimulatory domains and an intracellular signaling domain are described above. The antigen-specific targeting domains may be capable of specifically binding, in an MHC unrestricted manner, an antigen which is not normally bound by a T-cell receptor in that manner.

In an embodiment, the genetically engineered cells that express the CARs (for example bispecific CARs) of the invention co-express EGFRt. In a further embodiment, the genetically engineered cells that express the CARs (for example bispecific CARs) co-express EGFRt and CCR. In an additional embodiment, the genetically engineered cells that express the CARs (for example bispecific CARs) co-express EGFRt and DHFR (for example mutant DHFR). In another embodiment, the genetically engineered cells that express the CARs (for example bispecific CARs) co-express EGFRt, CCR and DHFR (for example mutant DHFR).

The genetically engineered cells express a CAR having at least two antigen-specific targeting regions which are specific for at least two different target antigens. In one embodiment, the antigen-specific targeting regions comprise target-specific antibodies or functional equivalents or fragments or derivatives thereof. The antigen-specific antibody may be the Fab fragment of the antibody or the single chain variable fragment (scFv) of the antibody.

Genetically engineered cells which may comprise and express the CARs of the invention include, but are not limited to, T-lymphocytes (T-cells), naïve T cells ($T_N$), memory T cells (for example, central memory T cells ($T_{CM}$), effector memory cells ($T_{EM}$)), natural killer cells, hematopoietic stem cells and/or pluripotent embryonic/induced stem cells capable of giving rise to therapeutically relevant progeny. In an embodiment, the genetically engineered cells are autologous cells. By way of example, individual T-cells of the invention may be CD4+/CD8−, CD4−/CD8+, CD4−/CD8− or CD4+/CD8+. The T-cells may be a mixed population of CD4+/CD8− and CD4−/CD8+ cells or a population of a single clone. CD4+ T-cells of the invention may produce IL-2, IFNγ, TNFα and other T-cell effector cytokines when co-cultured in vitro with cells expressing the target antigens (for example CD20+ and/or CD19+ tumor cells). $CD8^+$ T-cells of the invention may lyse antigen-specific target cells when co-cultured in vitro with the target cells. In some embodiments, T cells may be any one or more of $CD45RA^+$ $CD62L^+$ naïve cells, $CD45RO^+$ $CD62L^+$ central memory cells, $CD62L^-$ effector memory cells or a combination thereof (Berger et al., Adoptive transfer of virus-specific and tumor-specific T cell immunity. Curr Opin Immunol 2009 21(2)224-232).

Genetically modified cells may be produced by stably transfecting cells with DNA encoding the CAR of the invention. DNA encoding the CAR of the invention (for example bispecific CAR) may also encode EGFRt, CCR and/or DHFR (for example mutant DHFR). In one embodiment, a first polynucleotide encodes the CAR (for example bispecific CAR) and is linked via IRES sequences or a polynucleotide that encodes a cleavable linker, to a second polynucleotide that encodes EGFRt. In another embodiment, the first polynucleotide encodes the CAR (for example bispecific CAR) and is linked via IRES sequences or a polynucleotide that encodes a cleavable linker, to a second polynucleotide that encodes EGFRt and the first or second polynucleotides are linked to a third polynucleotide that encodes CCR or DHFR (for example mutant DHFR), also via IRES sequences or a polynucleotide that encodes a cleavable linker. In a further embodiment, the first polynucleotide encodes the CAR (for example bispecific CAR) and is linked via IRES sequences or a polynucleotide that encodes a cleavable linker, to a second polynucleotide that encodes EGFRt and the first and second polynucleotides are linked to a third polynucleotide that encodes CCR and a fourth polynucleotide that encodes DHFR (for example mutant DHFR) via IRES sequences or a polynucleotide that encodes a cleavable linker. Viral vectors are commonly used to carry heterologous genes into cells (e.g., T-cells). Examples of viral vectors which may be used to generate genetically modified cells include but are not limited to SIN lentiviral vectors, retroviral vectors, foamy virus vectors, adeno-associated virus (AAV) vectors and/or plasmid transposons (e.g., sleeping beauty transposon system).

Various methods produce stable transfectants which express the CARs of the invention. In one embodiment, a method of stably transfecting and re-directing cells is by electroporation using naked DNA. By using naked DNA, the time required to produce redirected cells may be significantly reduced. Additional methods to genetically engineer cells using naked DNA encoding the CAR of the invention include but are not limited to chemical transformation methods (e.g., using calcium phosphate, dendrimers, liposomes and/or cationic polymers), non-chemical transformation methods (e.g., electroporation, optical transformation, gene electrotransfer and/or hydrodynamic delivery) and/or particle-based methods (e.g., impalefection, using a gene gun and/or magnetofection). The transfected cells demonstrating presence of a single integrated un-rearranged vector and expression of the CAR may be expanded ex vivo. In one embodiment, the cells selected for ex vivo expansion are $CD8^+$ and demonstrates the capacity to specifically recognize and lyse antigen-specific target cells.

Viral transduction methods may also be used to generate redirected cells which express the CAR of the invention. Cell types that may be used to generate genetically modified cells expressing the bispecific CAR of the invention include but are not limited to T-lymphocytes (T-cells), natural killer cells, hematopoietic stem cells and/or pluripotent embryonic/induced stem cells capable of giving rise to therapeutically relevant progeny.

Stimulation of the T-cells by an antigen under proper conditions results in proliferation (expansion) of the cells and/or production of IL-2. The cells comprising the CAR of the invention will expand in number in response to the binding of one or more antigens to the antigen-specific targeting regions of the CAR. The invention also provides a method of making and expanding cells expressing a CAR. The method comprises transfecting or transducing the cells with the vector expressing the CAR and stimulating the cells with cells expressing the target antigens, recombinant target antigens, or an antibody to the receptor to cause the cells to proliferate, so as to make and expand T-cells. In an embodiment, the cells may be any one or more of T-lymphocytes (T-cells), natural killer (NK) cells, hematopoietic stem cells (HSCs) or pluripotent embryonic/induced stem cells capable of giving rise to therapeutically relevant progeny.

In an exemplary embodiment, the genetically engineered cells of the invention express a bispecific CAR which is specific for CD19 and CD20 antigens. In a further embodiment, a genetically engineered T-cell expresses the bispecific CARs CD19scFv-Gly4ser-linker-CD20scFv-hulgG4-hinge-CD28-41BB(cyto)-zeta(cyto) or CD19scFv-Gly4ser-linker-CD20scFv-hulgG4-hingeCH2CH3-CD28tm/cyto-zeta or CD19-Gly4serlinker-CD20scFv-CD8alphahinge-CD8alphaTM-41BBcostim-zetacyto.

In an exemplary embodiment, the invention provides a method of making and expanding T-cells expressing a CD19-specific and CD20-specific CAR. The method comprises using a lentivirus to transduce CD3×CD28 bead-stimulated purified central memory T-cells (such as T-cells from peripheral blood) with the vector expressing the CD19 and CD20 bispecific CAR, growing the T-cells in the presence of rhuIL-2 and/or IL-15 and restimulating the T-cells with CD19$^+$ and CD20$^+$ cells, recombinant CD19 and CD20, or an antibody to the receptor to cause the T-cells to proliferate, so as to make and expand CD19-specific and CD20-specific T-cells.

Therapeutic Methods of the Invention

The CARs of the invention may be used to overcome therapeutic failures arising from antigen loss escape variants, to reduce resistance to existing therapies and/or to treat diseases associated with the antigens targeted by the CARs.

Accordingly, the invention also provides methods for treating a disease associated with the antigen targeted by the CAR of the invention in a subject in need thereof. The method comprises providing a composition comprising the CAR of the invention and administering an effective amount of the composition so as to treat the disease associated with the antigen in the subject.

The invention also provides methods for overcoming therapeutic failures arising from antigen loss escape variants in disease states (e.g., B-cell diseases) in subjects in need thereof. The method comprises providing a composition comprising the CAR of the invention and administering an effective amount of the composition so as to treat the disease associated with the antigen in the subject.

In some embodiments, the composition comprises a polynucleotide encoding the CAR, a protein comprising the CAR or genetically modified cells comprising the CAR. In another embodiment, the genetically modified cells of the composition are T-lymphocytes (T-cells), naïve T cells ($T_N$), memory T cells (for example, central memory T cells ($T_{CM}$), effector memory cells ($T_{EM}$)), natural killer (NK) cells, hematopoietic stem cells (HSCs) or pluripotent embryonic/induced stem cells capable of giving rise to therapeutically relevant progeny, which express the CAR of the invention. The compositions of the invention may be administered alone or in conjunction with existing therapies. If other therapies are used in conjunction, the compositions of the invention may be administered concurrently or sequentially with the other the existing therapies.

Pharmaceutical Compositions

In various embodiments, the present invention provides pharmaceutical compositions comprising a pharmaceutically acceptable excipient and a therapeutically effective amount of the CAR (for example, bispecific CAR) of the invention. The CAR of the invention in the composition may be any one or more of a polynucleotide encoding the CAR, a protein comprising the CAR or genetically modified cells comprising the CAR. The composition may further comprise polynucleotides encoding EGFRt, CCR and/or DHFR (for example mutant DHFR), proteins co-expressed with the CAR including EGFRt, CCR and/or DHFR or genetically modified cells that express the CAR and co-express EGFRt, CCR and/or DHFR. "Pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients may be solid, liquid, semisolid, or, in the case of an aerosol composition, gaseous.

In various embodiments, the pharmaceutical compositions according to the invention may be formulated for delivery via any route of administration. "Route of administration" may refer to any administration pathway known in the art, including but not limited to aerosol, nasal, oral, intravenous, intramuscular, intraperitoneal, inhalation, transmucosal, transdermal, parenteral, implantable pump, continuous infusion, topical application, capsules and/or injections.

The pharmaceutical compositions according to the invention can also contain any pharmaceutically acceptable carrier. "Pharmaceutically acceptable carrier" as used herein refers to a pharmaceutically acceptable material, composition, or vehicle that is involved in carrying or transporting a compound of interest from one tissue, organ, or portion of the body to another tissue, organ, or portion of the body. For example, the carrier may be a liquid or solid filler, diluent, excipient, solvent, or encapsulating material, or a combination thereof. Each component of the carrier must be "pharmaceutically acceptable" in that it must be compatible with the other ingredients of the formulation. It must also be suitable for use in contact with any tissues or organs with which it may come in contact, meaning that it must not carry a risk of toxicity, irritation, allergic response, immunogenicity, or any other complication that excessively outweighs its therapeutic benefits.

The pharmaceutical compositions according to the invention can also be encapsulated, tableted or prepared in an emulsion or syrup for oral administration. Pharmaceutically acceptable solid or liquid carriers may be added to enhance or stabilize the composition, or to facilitate preparation of the composition. Liquid carriers include syrup, peanut oil, olive oil, glycerin, saline, alcohols and water. Solid carriers include starch, lactose, calcium sulfate, dihydrate, terra alba, magnesium stearate or stearic acid, talc, pectin, acacia, agar or gelatin. The carrier may also include a sustained release material such as glyceryl monostearate or glyceryl distearate, alone or with a wax.

The pharmaceutical preparations are made following the conventional techniques of pharmacy involving milling, mixing, granulation, and compressing, when necessary, for tablet forms; or milling, mixing and filling for hard gelatin capsule forms. When a liquid carrier is used, the preparation will be in the form of syrup, elixir, emulsion or an aqueous or non-aqueous suspension. Such a liquid formulation may be administered directly p.o. or filled into a soft gelatin capsule.

The pharmaceutical compositions according to the invention may be delivered in a therapeutically effective amount. The precise therapeutically effective amount is that amount of the composition that will yield the most effective results in terms of efficacy of treatment in a given subject. This amount will vary depending upon a variety of factors, including but not limited to the characteristics of the therapeutic compound (including activity, pharmacokinetics, pharmacodynamics, and bioavailability), the physiological condition of the subject (including age, sex, disease type and stage, general physical condition, responsiveness to a given dosage, and type of medication), the nature of the pharmaceutically acceptable carrier or carriers in the formulation, and the route of administration. One skilled in the clinical and pharmacological arts will be able to determine a therapeutically effective amount through routine experimentation, for instance, by monitoring a subject's response to administration of a compound and adjusting the dosage accordingly. For additional guidance, see *Remington: The Science and Practice of Pharmacy* (Gennaro ed. 20th edition, Williams & Wilkins PA, USA) (2000).

EXAMPLES

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Example 1

FIG. 1 is a schematic representation of the bispecific chimeric antigen receptor of the invention. In an exemplary embodiment of the invention, FIGS. 2A and 2B depict the components of bispecific anti-CD19xanti-CD20 bispecific CAR. FIGS. 2A and 2B also depict a schematic of the complete cDNA packaged into epHIV-7 lentivirus vector transfer plasmid. FIG. 3 and FIG. 4 show the nucleic and amino acid sequences of an exemplary bispecific CAR, namely GMCSFss-CD19scFv-Gly4Ser1linker-CD20scFv-IgG4Hinge-CD28tm-41BBzeta-T2A-EGFRt_epHIV7.

Example 2

FIG. 5 is a schematic showing the vector construct of an exemplary CAR of the invention, namely, the CD19scFv-CD20scFv-IgG4-CD28tm-CD28costim-CD3zeta transgene construct. The CD19scFv-CD20scFv-IgG4-CD28tmCD28costim-CD3zeta transgene was assembled using the one-step isothermal DNA assembly method previously described by Gibson et. al. (Enzymatic assembly of DNA molecules upto several hundred kilobases. *Nature Methods*. 2009; 6:343-345). The $V_L$ and $V_H$ domains of the CD19 scFv construct was sequenced from a CD19CAR-CD28-Zeta transgene previously described. Schmitz N, Dreger P, Glass B, Sureda A. Allogeneic transplantation in lymphoma: current status. *Haematologica*. 2007; 92(11): 1533-1548) through polymerase chain reaction (PCR). The $V_H$ and $V_L$ domains of the CD20 scFv were assembled by spliced-overlap polymerase chain reaction using a CD20R-CD28-Zeta transgene previously described (Michael Jensen et al., CD20 is a molecular target for scFvFc:zeta receptor redirected T-cells: implications for cellular immunotherapy of CD20+ malignancy. *Biology of Blood and Marrow Transplant*. 1998; 4:75-83). The $V_H$ and the $V_L$ domains of CD19 scFv and CD20 scFv were linked with an 18-residue linker peptide as previously described. The IgG4-CD28tm-CD28costim domain was sequenced using the CD19R-CD28-CD3zeta transgene by PCR. The CD3zeta-T2A-EGFRt_epHIV7 lentiviral destination vector was prepared by NheI and RsrII restriction digestion of the CD19R-CD28 portion from a CD19R-CD28-Zeta-T2A-EGFRt_epHIV7 plasmid previously described (Seitaro Terakura et al., Generation of CD19-CAR modified CD8+ T-cells derived from virus-specific central memory T-cells. *Blood*. Oct. 26, 2011). The final CD19scFv-CD20scFv-IgG4-CD28tm-CD28costim-CD3zeta construct was assembled by the one-step isothermal Gibson DNA assembly method using the restriction digested Zeta-epHIV7 destination vector and the CD19scFv, CD20scFv, and IgG4-CD28tm-CD28costim-DNA fragments with primers for each containing a 30 bp overlap at the 5' terminus.

TABLE 1

Regulatory Elements Present in the bispecific CAR epHIV-7 Transfer Plasmid

| Regulatory Element | Function |
| --- | --- |
| U5 | 5' Unique sequence |
| Psi | Packaging signal |
| RRE | Rev-responsive element |
| flap | Contains polypurine track sequence and central termination sequence to facilitate nuclear import of pre-integration complex |
| EF1p Promoter | EF1-alpha Eukaryotic Promoter sequence driving expression of CD19 x CD20 CAR |
| WPRE | Woodchuck hepatitis virus derived regulatory element to enhance viral RNA transportation |
| delU3 | 3' U3 with deletion to generate SIN vector |
| R | Repeat sequence within LTR |
| U5 | 3' U5 sequence in LTR |
| $Amp^R$ | Ampicillin-resistance gene |
| CoEI ori | Replication origin of plasmid |
| SV40 ori | Replication origin of SV40 |
| CMV promoter | CMV promoter to generate viral genome RNA |
| R | Repeat sequence within LTR |

Example 3

HEK 293T-cells were transfected with anti-CD19× CD20CAR-T2A-EGFRt epHIV-7 transfer plasmid or with anti-CD20×CD19CAR-T2A-EGFRt epHIV-7 transfer plasmid. Transfected cells were stained with biotinylated anti-Fc antibodies and streptavidin PE (SA-PE) and then were subjected to flow cytometric analysis for detection of expression of the above two CARs.

Both the anti-CD19×CD20 CAR and the anti-CD20× CD19 CAR were expressed on transfected HEK 293T cells.

The epHIV-7 transfer plasmid co-expressed EGFRt with the above two bispecific CARs. EGFRt co-expression was detected on the same transfected cells using a combination of biotinylated anti-EGFR antibodies/SA-PE staining and flow cytometric analysis.

Example 4

Primary human peripheral blood derived T-cells were activated with OKT3 and then were lentivirally transduced with monospecific anti-CD19 CAR, monospecific anti-CD20 CAR or bispecific anti-CD19×CD20CAR-T2A-EGFRt epHIV7 lentivirus vector. epHIV7 lentivirus vector also encoded EGFRt together with monospecific anti-CD19 CAR, monospecific anti-CD20 CAR or bispecific anti-CD19×CD20. Thus, cells expressing the CARs co-expressed EGFRt. Transfected cells were stained with biotinylated anti-EGFR antibodies and SA-PE and then were subjected to flow cytometric analysis for detection of EGFRt expression and co-expression of monospecific or bispecific CARs. Of the cells transfected with monospecific anti-CD19 CAR, 51% expressed EGFRt; of the cells transfected with monospecific anti-CD20 CAR, 38.5% expressed EGFRt; of the cells transfected with the bispecific anti-CD19×CD20 CAR, 63.8% expressed EGFRt.

T cell receptor (TCR) complex in transfected cells was also detected in the same transfected cells using FITC-conjugated anti-TCRα and anti-TCRβ antibodies staining and flow cytometric analysis.

Example 5

H9 cells were genetically modified to express CD19, or CD20, or both CD19 and CD20. Cells were stained with anti-CD19 and anti-CD20 antibodies and then were subject to flow cytometric analysis to detect the expression of CD19 and CD20. Cytometric analysis confirmed the desired expression profile of $CD19^+CD20^-$, $CD19^-CD20^+$, and $CD19^+CD20^+$ H9 cells, namely, genetically engineered H9 cells expressed CD19, or CD20, or both CD19 and CD20 thereby simulating cancer target cells, which contain antigen-negative antigen loss escape variants. As described later, these cell lines were subsequently used as target cells to stimulate CAR-expressing T-cell lines, which act as effector cells to kill target cells.

Also, endogenous levels of CD19 and CD20 expression in SUP-B15 and DHL-6 cell lines was analyzed using anti-CD19 APC and anti-CD20 PE staining and flow cytometric analysis. SUP-B15 cell line expressed high level of CD19 with low level of CD20 (thus $CD19^+CD20^-$), and DHL-16 cell line expressed high level of CD20 with low level of CD19 (thus $CD19^- CD20^+$).

Example 6

A 4-hour chromium release assay was used to measure the lysis of the target cells by the effector cells. Effector cells are primary human T-cells lentivirally transduced to express monospecific anti-CD19 CAR, monospecific anti-CD20 CAR or bispecific anti-CD19×CD20 CAR. The bispecific anti-CD19×CD20 CAR effector T-cells effectively lysed all $CD19^+CD20^-$, $CD19^-CD20^+$, and $CD19^+CD20^+$ target cells, which include $CD19^+CD20^-$ H9 cells, $CD19^-CD20^+$ H9 cells, $CD19^+CD20^+$ H9 cells and SUP-B15 cells. At effector to target ratios of 1:1, 3:1, 10:1, and 30:1, about 25%, 45%, 50% and 60%, respectively, target cells were lysed.

In contrast, monospecific CAR expressing T-cell lines fail to lyse antigen-negative antigen loss escape variants, which escaped from the monospecific CAR effector cells. The anti-CD19 CAR effector T-cells failed to lyse $CD19^-CD20^+$ targets and the anti-CD20 CAR effector T-cells failed to lyse $CD19^+CD20^-$ targets.

Example 7

Bispecific CAR-expressing CD4 enriched T-cells were activated for cytokine secretion (Interferon gamma (IFN-g, IFN-γ)) upon stimulation by $CD19^+CD20^-$, $CD19^-CD20^+$, and $CD19^+CD20^+$ target cells, which include $CD19^+CD20^-$ H9 cells, $CD19^-CD20^+$ H9 cells, $CD19^+CD20^+$ H9 cells and SUP-B15 cells. IFN-γ content was measured by cytokine bead array of culture supernatants of T-cells and target cells after 24-hours of co-culture. Activated bispecific CAR-expressing CD4 enriched T-cells secreted at least 2500 pg/ml INF-g upon stimulation by every type of target cells. In contrast, monospecific CAR expressing T-cell lines were not activated for cytokine INF-g secretion upon stimulation by antigen-negative antigen loss escape variants, which escaped from the monospecific CAR effector cells. CD19 CAR T-cells failed to secrete IGN-γ upon co-culture with $CD19^-CD20^+$ target cells and CD20 CAR T-cells failed to secrete IGN-γ upon co-culture with $CD19^+CD20^-$ target cells.

| In-vitro Stimulation Assay | |
|---|---|
| Stimulators (3 × 10^5): | |
| TM-LCL | H9 parent |
| OKT3-TM-LCL | H9 CD19R |
| SUP-B15 | H9 CD20R |
| DHL-6 | H9 CD19/20R |
| Responders (1 × 10^6 on $S_1R_2D_{17}$): | |
| CD4 enriched mock | CD8 enriched mock |
| CD4 enriched CD19R | CD8 enriched CD19R |
| CD4 enriched CD20R | CD8 enriched CD20R |
| CD4 enriched CD19/20R | CD8 enriched CD19/20R |

Cells incubated for 24 hrs, and cell free supernatant will be harvested today for BioPlex assay

Example 8

The example below describes a CD19 specific chimeric antigen receptor linked to truncated epidermal growth factor receptor (EGFRt) via a T2A sequence. EGFRt may be linked to and co-expressed with other chimeric antigen receptors, for example, bispecific chimeric antigen receptors.

Applicants demonstrated the utility of such a truncated EGFR (huEGFRt) expressed by transduced T cells for immunomagnetic purification using biotinylated cetuximab, cell tracking by flow cytometry and immunohistochemistry, and in vivo cell ablation after systemic cetuximab administration. In this exemplary embodiment, domain I and II of EGFRt have been deleted while domains III and IV have been retained.

The CD19CAR-T2A-EGFRt-epHIV7 lentiviral construct contains: (1) the chimeric antigen receptor (CAR) sequence consisting of the $V_H$ and $V_L$ gene segments of the CD19-specific FMC63 monoclonal antibody (mAb), an IgG4 hinge-$C_{H2}$-$C_{H3}$, the transmembrane, and cytoplasmic signaling domains of the co-stimulatory molecule CD28, and the cytoplasmic domain of the CD3ζ chain (Kowolik C K. et al., CD28 costimulation provided through a CD19-specific chimeric antigen receptor enhances in vivo persistence and antitumor efficacy of adoptively transferred T cells. *Cancer Res.* 2006, 66(22):10995-11004); (2) the self-cleaving T2A sequence (Szymczak A L. et al., Correction of multi-gene deficiency in vivo using a "self-cleaving" 2A peptide-based retroviral vector. *Nat Biotechnol* 2004; 22(5)589-594); and (3) the truncated EGFR sequence as indicated.

Immunomagnetic Enrichment of huEGFRt+ Human T Cells after Lentiviral Transduction The biotinylated cetuximab was used for either immunomagnetic selection or FACS sorting of huEGFRt+ cells. Applicants used biotinylated cetuximab in conjunction with commercially available antibiotin microbeads for the immunomagnetic selection of human T cells transduced with a self-inactivating lentivirus that directs the co-expression of CD19CAR and huEGFRt.

PBMCs or purified central memory (CD45RO+CD62L+ $T_{CM}$) or effector memory (CD45RO+CD62L+ $T_{EM}$) T-cell subsets were stimulated with anti-CD3/anti-CD28 beads and then transduced by lentiviral vector to generate a panel of primary human T-cell lines, of which 2.6%-40% expressed huEGFRt and CAR. The unselected cells were labeled with biotinylated cetuximab and anti-biotin microbeads; and then were separated to consistently obtain a selected cell population, of which 90% express huEGFRt and CAR.

Unselected T cells and selected fraction were stained with biotinylated-cetuximab and either PE-conjugated streptavidin or PE-conjugated anti-biotin Ab, and then were subject to flow cytometric analysis. Selection of CD19CAR+EGFRt+ cells was performed either 3 days after transduction of OKT3 blasts (enriched from 38% to 98%), or after 1 rapid expansion cycle of transduced effector memory CD62LCD45RO+-derived cells (enriched from 20% to 96%), after 3 rapid expansion cycles of transduced CMVpp65-specific TCM-derived cells (enriched from 12% to 91%), or after 2 rapid expansion cycles of transduced CD8+TCM-derived cells (enriched from 3% to 97%). Selection of CD19CAR+EGFRt+IMPDH2dm+ cells was performed after 1 rapid expansion cycle of transduced TCM-derived cells (enriched from 25 to 92%).

CD19CAR-T2A-EGFRt-IMPDH2dm constructs contained in lentiviral vectors include codon optimized sequence portions of the CD19-specific, CD28 co-stimulatory CAR (CD19CAR), followed by the self-cleavable T2A, and selection markers huEGFRt and IMPDH2dm (a double mutant of the inosine monophosphate dehydrogenase 2 gene that allows for cell survival upon addition of mycophenolate 27), along with the Elongation Factor 1 promoter sequences (EF-1p), the GM-CSF receptor alpha chain signal sequences (GMCSFRss), and the 3 nucleotide stop codon.

Before immunomagnetic selection, a proliferative advantage of huEGFRt− cells over huEGFRt+ cells was observed in cultures of unselected transduced T cells subjected to OKT3-mediated expansion. However, after immunomagnetic selection, the level of huEGFRt expression and the frequency of expressing cells remained stable over 3 consecutive 14-day cycles of OKT3-based expansion[14]. The fold expansion of EGFRt+ cells after immunomagnetic selection was significantly enhanced over that of huEGFRt+ cells in the unselected cultures.

These data demonstrate that huEGFRt can serve as a cell surface marker unique to transduced human T cells and enable subsequent cetuximab-based immunomagnetic purification of stable huEGFRt-expressing cell populations which also express CARs.

Tracking of Adoptively Transferred huEGFRt+ T Cells Using Flow Cytometry and Immunohistochemistry To test the utility of huEGFRt for tracking the engraftment of adoptively transferred T cells, Applicants harvested blood and bone marrow specimens from NOD/Scid IL-2RγC$^{null}$ mice engrafted with CD19CAR+EGFRt+ human T cells.

First, unfixed peripheral blood and bone marrow mononuclear cell samples were subjected to flow cytometric analysis after being stained with biotinylated cetuximab and PE-conjugated streptavidin. Although the level of human CD45+ T-cell engraftment (20%-25%) was similar in animals administered either EGFRt-negative or -positive T cells, double staining for human CD45 and EGFR allowed for the resolution of huEGFRt+ (ie, transgeneexpressing) human T cells from their huEGFRt-negative counterparts.

Second, Applicants sought to determine whether standard paraffin embedded fixed tissue specimens were amenable to detection of huEGFRt+ T-cell infiltrates using EGFR-specific diagnostic kits. Applicants performed immunohistochemical analysis of paraffin-embedded femurs from engrafted mice and detected huEGFRt+ cells in the bone marrow. These data support the utility of huEGFRt to serve as a tracking marker for quantifying the frequency and tissue distribution of adoptively transferred T cells.

Cetuximab Binding to huEGFRt Sensitizes Human T Cells to ADCC

A valuable feature of a cell surface selection/tracking marker would be its capacity to serve as a target for in vivo cell ablation. Applicants evaluated the extent to which Cetuximab bound to huEGFRt on T cells activates ADCC of huEGFRt+ T cells in vitro, and whether Cetuximab administration could attenuate the engraftment of adoptively transferred huEGFRt+ T cells in NOD/scid mice.

$^{51}$Cr-labeled huEGFRt+ T cells as the target cells and human GM-CSF activated fresh PBMCs as effectors were co-cultured. Then, the addition of Cetuximab specifically sensitized huEGFRt+ T cells to ADCC cytolysis by effectors. Lysis of huEGFRt+ T cells was measured by 4-hour chromium release assay and results showed that Cetuximab addition significantly increased lysis from less than 5% to about 50%, 45%, 40% and 15% respectively at effector to target (effector:target) ratios 50:1, 25:1, 5:1 and 1:1.

In contrast, the addition of the CD20-specific mAb RITUXAN® (rituximab) had no effect on triggering ADCC of huEGFRt+ T cells in this assay.

Applicants next derived huEGFRt+ CTLL-2 murine T cells that were additionally modified to secrete autocrine IL-2 and express the firefly luciferase biophotonic reporter, and adoptively transferred these ffLuc+huEGFRt+ CTLL-2 cells via intravenous injection to NOD/scid mice, which subsequently received Cetuximab or RITUXAN® (rituximab). The in vivo engraftment of transferred CTLL-2, as measured by in vivo biophotonic imaging, was significantly inhibited (97%, P<0.05) in mice that received ERBITUX® (cetuximab) (1 mg intraperitoneally daily). The Cetuximab-mediated elimination of the ffLuc+huEGFRt+ CTLL-2 cells occurred between 4 and 6 days. These data support the use of Cetuximab administration as a therapeutic control for patients receiving huEGFRt+ T cells.

Example 9

This example describes T cells with an intrinsic γc cytokine signaling mechanism, and shows that chimeric cytokine receptors (CCR) IL-2/IL-15Rβ (CγCR2) and IL-7Rα (CγCR7) have the ability to improve the survival, persistence, and in vivo engraftment of cytotoxic T cells (CTLs). Truncated CD19 antigen (CD19t) was linked to CγCR via a T2A linker to show the expression of CγCR on the cell surface. The chimeric cytokine receptors described herein may be linked to the chimeric antigen receptors of the invention, such as bispecific CARs described herein.

To develop a cell-intrinsic, ligand-independent γc cytokine platform, Applicants engineered chimeric γc cytokine receptors (CγCR) comprised of the IL-7 cytokine tethered by ten amino acids to the extracellular domain of IL-7Rα. To engineer a CγCR that confers an IL-7R signal, IL-7 cytokine was tethered to the full length IL-7Rα chain (CγCR7). A CγCR that provides an IL-2/IL-15Rβ signal was engineered by tethering the IL-7 cytokine to the extracellular and transmembrane domain of IL-7Rα fused to the cytoplasmic domain of IL-2/IL-15Rβ (CγCR2). These single chain chimeric receptors are expected to require endogenous γc chain for signaling.

Constructs were then generated where the CγCR transgenes were followed by the self-cleavable T2A sequence, and a cytoplasmically truncated CD19 antigen (CD19t). CγCR and CD19t are expressed as a single transcript and cleaved post-translationally at the C-terminus of the T2A self-cleaving peptide to yield two separate type 1 membrane proteins CγCR(T2A) and CD19t. Based on expression of two proteins from a single transcript, the ratio of CγCR (T2A) to CD19t expression is 1:1, therefore, cell surface CD19t is an indication of CγCR cell surface expression. Lentiviral transduction and expression of these constructs could then be measured by surface CD19t expression, such as that seen in both Jurkat and NK-92 cell lines.

A third CγCR was also engineered, having IL-7 cytokine tethered to a truncated IL-7Rα (CγCR7t), which is missing amino acids 1-126 from the extracellular domain of the IL-7Rα. A molecular model of CγCR7t dimerization with the endogenous γc chain is necessary for signal transduction. The lack of amino acids 1-126 of the extracellular domain of IL-7Rα renders the CγCR7t nonfunctional.

Truncated CγCR7 expression does not functionally signal or support cytokine independent cell growth. Flow cytometric detected cell-surface CD19t on lenti-transduced Jurkat (95% CD19t$^+$CγCR7t$^+$) and Teff cell lines (97% CD19t$^+$ CγCR7t$^+$). Western blot analysis of STAT5 phosphorylation within CγCR7t expressing Jurkat cell line did not detect obvious increase of phosphorylated STAT5 as compared to non-transduced control Jurkat cell line. Positive controls OKT3 stimulated PBMC cultured in 50 U/ml IL-2 and 10 ng/ml IL-15 and K562 showed activation of increased phosphorylated STAT5. Accordingly, expansion and viability of CTLs transduced with CγCR7t cultured for 20 days were still dependent on cytokines.

To determine if functional CγCRs such as CγCR2 and CγCR7 could support the growth of CD8$^+$ human primary T cells in the absence of exogenous cytokine, we measured the expansion of CTLs expressing each CγCR. Human primary T cells expressing CγCR7t were unable to expand in the absence of exogenous cytokine. Both CγCR2 and CγCR7 were able to support the survival and proliferation of the CD8$^+$ T cells through maintenance of viability, in a manner similar to that of parental cells cultured in 5 U/ml and 0.5 U/ml IL-2, respectively. The increased total cell expansion measured for CγCR2$^+$ versus CγCR7$^+$ CTL correlates with increased expression (i.e., MFI of 26 for CγCR7 versus 52 for CγCR2) of Ki67, a nuclear antigen protein present in G1, S, G2, and M phase of the cell cycle. Higher Bcl-2, an key antiapoptotic protein induced in response to IL-2 and IL-7 signaling, expression was observed for CγCR7$^+$ versus CγCR2$^+$ CTL, supporting the ability of CγCR7 to maintain the survival of the human primary T cells. Together this data suggests that, although both CγCRs support cytokine-independent T cell viability and expansion, CγCR2 provides a proliferative advantage while CγCR7 maintains survival for effector CD8$^+$ CTLs.

CγCR Expressing CD8$^+$ T Cells Exhibit Cytokine Independent Engraftment In Vivo Studies by our lab and others indicate that human CTL engraftment in NOD/Scid IL-2RγC$^{null}$ mice is dependent on exogenous administration of human IL-15 or IL-2. To test the potential of CγCR expression in CTLs to overcome this dependence, parental effector T cells, CγCR7$^+$ CTLs, and CγCR2$^+$ CTLs were injected into the tail vein of immuno-deficient NOD/Scid IL-2RγC$^{null}$ mice in the absence of exogenous cytokine administration. Total engraftment was compared by harvesting at least four mice per group at day 8, 17, 24, and 48 and analyzing T cell levels in the blood and bone marrow.

In the blood, CγCR2$^+$ CTLs had impressive significant (P<0.007) exogenous cytokine independent engraftment compared to CγCR7$^+$ CTLs and the parental cells. In the bone marrow, both CγCR7$^+$ CTLs (P<0.03) and CγCR2$^+$ CTLs (P<0.0005) had significant exogenous cytokine independent engraftment compared to the parental cells. CγCR2$^+$ CTLs had higher engraftment compared to CγCR7$^+$ CTLs. This indicates that both CγCR7$^+$ CTLs and CγCR2$^+$ CTLs are capable of supporting exogenous cytokine independent engraftment but the total percentage of cells was different. The blood supported higher percent engraftment of CγCR2$^+$ CTLs compared to bone marrow. The bone marrow supported the engraftment of CγCR7$^+$ CTLs over a longer period of time. Importantly, the engraftment was not infinite as the cells were no longer present in the blood and bone marrow at day 48 in either group.

Cell intrinsic γc cytokine signals can replace the need for exogenous cytokine administration for the support of adoptively transferred CTLs. Providing cell intrinsic cytokine receptors can overcome the major limitation of adoptive immunotherapy; the long-term persistence of adoptively transferred CTL. This may eliminate the need for administration of exogenous cytokine, which may reduce toxicities and bystander effects on endogenous cell types.

Example 10

This example shows that CD19 chimeric antigen receptor linked to EGFRt and DHFR can be regulated by methotrexate. Using the methods described herein, the dihydroxyfolate receptor described herein may be linked to the bispecific chimeric antigen receptors of the invention.

Applicants developed a human selectable transgene using a variant of human dihydrofolate reductase (hDHFR) that would enable selection of T cells with the less toxic, pharmaceutically available drug methotrexate (MTX). MTX exerts its anti-proliferative effect through competitive inhibition of DHFR, a key enzyme essential for de novo synthesis of thymidylate nucleotides.

In the instant example, Applicants evaluated the potential of DHFR$^{FS}$ (hDHFR L22F/F31S variant) mediated in vitro selection of primary human T cells that co-express a CD19-specific chimeric antigen receptor (CD19CAR for targeting of CD19-expressing tumors). In this strategy, we hypothesized that exposure of a transduced mixed population of T cells to the lymphotoxic drug MTX should lead to elimination of untransduced T cells and selective expansion of DHFR$^{FS}$/CD19CAR T cells co-expressing T cells, increasing the anti-tumor efficacy of the T cell population as a whole. Here Applicants show that DHFR$^{FS}$-mediated selection of gene modified T cells enforced the CD19CAR therapeutic transgene expression, and allowed for the derivation of CAR$^+$ stable integrants in the presence of clinically attainable concentrations of MTX (e.g., 0.1 μM MTX).

To translate the hDHFR$^{FS}$ selection approach for potential therapeutic utility, Applicants designed a lentiviral vector co-expressing hDHFR$^{FS}$ in conjunction with a CD19-specific chimeric antigen receptor (CD19CAR) and a truncated human EGFR polypeptide as a tracking marker (huEGFRt) each separated by a ribosomal skip T2A sequence.

CTLL2 T cells were first transduced with this CD19CAR-huEGFRt-hDHFR$^{FS}$ lentiviral vector and evaluated for their resistance to MTX. Ten days after lenti-transduction, 7-8% of the cells were positive for CD19CAR and huEGFRt expression.

In the absence of MTX, the non-transduced and transduced CTLL2 cells expanded at an equivalent rate (21- and 27-fold respectively). After incubation with MTX (0-0.1 μM) for 8 days, a 7-fold expansion with 80% survival was observed with transduced cells, while exposure of non-transduced CTLL2 cells to ≥0.05 μM MTX resulted in strong inhibition of non-transduced CTLL2 cell expansion and viability.

Evaluation of huEGFRt expression levels of transduced CTLL2 cells after 8 days in culture with varying concentrations of MTX further revealed significant MTX-mediated enrichment of transgene-expressing huEGFRt$^+$ cells (49%, 93%, 98.5%, 99% at 0.01, 0.025, 0.05 and 0.1 μM MTX respectively).

To further characterize the maximum dose of MTX that could be tolerated by selected CTLL2 cells, transduced CTLL2 cells that had been cultured in 0.1 μM MTX for 8 days were re-plated at a wider range of MTX concentrations (up to 0.75 μM). These transduced and pre-MTX selected cells were able to expand 90-100 fold at MTX concentrations up to 0.25 μM, which is equivalent to non-transduced control CTLL2 expansion in the absence of MTX.

Applicants transduced primary human T cells with the same CD19CAR-huEGFRt-hDHFR$^{FS}$ lentiviral vector. Purified CD62L$^+$CD45RO$^+$ T cells were used as a starting population based on their potential for persistence after adoptive transfer. Ten days after transduction, these T cells were cultured in varying concentrations of MTX and assessed for cell number and viability over time. After 10 days, transduced and non-transduced T cells expanded equally (80-fold) in the absence of MTX. Furthermore, even at 0.1 μM MTX, transduced T cells maintained a viability of 63%, while non-transduced primary human T cells exhibited strong inhibition of both viability and fold-expansion starting at concentrations as low as 0.025 μM MTX.

Flow cytometric evaluation of transduced T cells after 10 days in culture with varying concentrations of MTX revealed significant MTX-mediated enrichment of transgene-expressing cells (e.g., 0.025 M MTX enriched about 54% CD19CAR$^+$ and 79% EGFRt$^+$; 0.05 μM MTX enriched about 76% CD19CAR$^+$ and 89% EGFRt$^+$)

Comparison of CD19CAR and EGFRt expression at day 6 vs. day 10 of culture revealed the steady progression of this MTX/DHFR$^{FS}$-mediated selection over time (Day 0: 18% CD19CAR$^+$, 28% EGFRt$^+$; Day 6: 48% CD19CAR$^+$, 71% EGFRt$^+$; Day 10: 70% CD19CAR$^+$, 88% EGFRt$^+$).

All references cited herein are incorporated by reference in their entirety as though fully set forth. Unless defined otherwise, technical and scientific terms used herein have the same meaning as commonly understood by one of ordinary skill in the art to which this invention belongs. Singleton et al., *Dictionary of Microbiology and Molecular Biology* 3$^{rd}$ ed., J. Wiley & Sons (New York, NY 2001); March, *Advanced Organic Chemistry Reactions, Mechanisms and Structure* 5$^{th}$ ed., J. Wiley & Sons (New York, NY 2001); and Sambrook and Russel, *Molecular Cloning: A Laboratory Manual* 3rd ed., Cold Spring Harbor Laboratory Press (Cold Spring Harbor, NY 2001), provide one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described. For purposes of the present invention, the following terms are defined below.

While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.).

SEQUENCE LISTING

```
Sequence total quantity: 17
SEQ ID NO: 1            moltype = DNA   length = 3273
FEATURE                 Location/Qualifiers
misc_feature            1..3273
                        note =
                         GMCSFRss-CD19scFv-Gly4Ser1linker-CD20scFv-IgG4Hinge-CD28tm-
                         41BB-C D3zeta-T2A-EGFRt_epHIV7
source                  1..3273
                        mol_type = other DNA
                        organism = synthetic construct
```

```
SEQUENCE: 1
atgctgctgc tggtgaccag cctgctgctg tgcgagctgc ccacccccgc ctttctgctg    60
atccccatga cccagaccac ctccagcctg agcgccagcc tgggcgaccg ggtgaccatc   120
agctgccggg ccagccagga catcagcaag tacctgaact ggtatcagca gaagcccgac   180
ggcaccgtca agctgctgat ctaccacacc agccggctgc acagcggcgt gcccagccga   240
tttagcggca gcggctccgg caccgactac agcctgacca tctccaacct ggaacaggaa   300
gatatcgcca cctactttg ccagcagggc aacacactgc cctacacctt tggcggcgga    360
acaaagctga aaatcaccgg cagcacctcc ggcagcggca gcctggcag cggcgagggc     420
agcaccaagg gcgaggtgaa gctgcaggaa agcggccctg gcctggtggc cccccagcag    480
agcctgagcg tgacctgcac cgtgagcggc gtgagcctgc ccgactacgg cgtgagctgg    540
atccggcagc ccccaggaa gggcctgaa tggctgggcg tgatctgggg cagcgagacc     600
acctactaca cagcgccct gaagagccgg ctgaccatca tcaaggacaa cagcaagagc    660
caggtgttcc tgaagatgaa cagcctgcag accgacgaca ccgccatcta ctactgcgcc    720
aagcactact actacggcgg cagctacgcc atggactact ggggccaggg caccagcgtg    780
accgtgagca gcggaggtgg tggatccgag gtgcagctgc agcagtctgg ggctgagctg    840
gtgaagcctg ggcctcagt gaagatgtcc tgcaaggctt ctggctacac atttaccagt    900
tacaatatgc actgggtaaa gcagacacct ggacagggcc tggaatggat tggagctatt    960
tatccaggaa atggtgatac ttcctacaat cagaagttca aggcaaggc cacattgact    1020
gcagacaaat cctccagcac agcctacatg cagctcagca gcctgacatc tgaggactct   1080
gcggactatt actgtgcaag atctaattat tacggtagta gctactggtt cttcgatgtc   1140
tggggcgcag gaccacggt caccgtctcc tcaggcagta ctagcggtgg tggctccggg    1200
ggcggttccg gtgggggc cagcagcgac attgtgctga cccaatctcc agctatcctg    1260
tctgcatctc caggggagaa ggtcacaatg acttgcaggg ccagctcaag tgtaaattac   1320
atggactggt accagaagaa gccaggatcc tcccccaaac cctggattta tgccacatcc   1380
aacctggctt ctggagtccc tgctcgcttc agtggcagtg gtctgggac ctcttactct    1440
ctcacaatca gcagagttga ggctgaagat gctgccatt attactgcca gcagtggagt    1500
tttaatccac ccacgttcgg aggggggacc aagctggaaa taaaagagag caagtacgga    1560
ccgcctgcc ccccttgcc tatgttctg gtgctggtgg tggtcggagg cgtgctggcc       1620
tgctacagcc tgctggtcac cgtggccttc atcatctttt gggtgaaacg gggcagaaag    1680
aaactcctgt atatattcaa acaaccattt atgagaccag tacaaactac tcaagaggaa    1740
gatggctgta gctgccgatt tccagaagaa gaagaaggag gatgtgaact gcgggtgaag    1800
ttcagcagaa gcgccgacgc ccctgcctac cagcagggcc agaatcagct gtacaacgag    1860
ctgaacctgg gcagaaggga agagtacgac gtcctggata gcggagagg cccggaccct    1920
gagatgggcg gcaagcctcg gcggaagaac cccaggaag gcctgtataa cgaactgcag    1980
aaagacaaga tggccgaggc ctacagcgag atcggcatga agggcgagcg gaggcgggc    2040
aagggccacg acggcctgta tcagggcctg tccaccgcca ccaaggatac ctacgacgcc    2100
ctgcacatgc aggccctgcc cccaaggctc gaggcggcg gagagggcag aggaagtctt    2160
ctaacatgcg gtgacgtgga ggagaatccc ggccctagga tgcttctcct ggtgacaagc    2220
cttctgctct gtgagttacc acaccagca ttcctcctga tcccacgcaa agtgtgtaac      2280
ggaataggta ttggtgaatt taaagactca ctctccataa atgctacgaa tattaaacac    2340
ttcaaaaact gcacctccat cagtggcgat ctccacatcc tgccggtggc atttaggggt    2400
gactcctca cacatactcc tcctctggat ccacaggaac tggatattct gaaaaccgta    2460
aagggaatca caggtttttt gctgattcag cttggcaaaa caggaacctc cat         2520
gcctttgaga acctagaaat catacgcggc aggaccaagc aacatggtca gttttctctt    2580
gcagtcgtca gcctgaacat aacatccttg ggattacgct ccctcaagga gataagtgat    2640
ggagatgtga atttcaggg aaacaaaaat tgtgctatgc aaatacaat aaactgga       2700
aaactgttg ggacctccgg tcagaaaacc aaaattataa gcaacagagg tgaaaacagc    2760
tgcaaggcca caggccaggt ctgccatgcc ttgtgctccc cgagggctg ctggggcccg     2820
gagcccaggg actgcgtctc ttgccggaat gtcagccgag caggaatg cgtggacaag    2880
tgcaaccttc tggagggtga gccaaggag tttgtggaga actctgagtg catacagtgc    2940
cacccagagt gcctgcctca ggccatgaac atcacctgca caggacgggg accagaacac    3000
tgtatccagt gtgccactg cattgacggc ccccactgcg tcaagacctg cccggcagga    3060
gtcatgggag aaaacaacac cctggtctgg aagtacgcag acgccggcca tgtgtgccac    3120
ctgtgccatc caaactgcac ctacggatgc actgggccag tcttgaagg ctgtccaacg    3180
aatgggccta gatccgtc catcgccact gggatggtgg gggccctcct cttgctgctg    3240
gtggtggccc tgggatcgg cctcttcatg tga                                 3273

SEQ ID NO: 2           moltype = DNA   length = 3273
FEATURE                Location/Qualifiers
misc_feature           1..3273
                       note =
                       GMCSFRss-CD19scFv-Gly4Ser1linker-CD20scFv-IgG4Hinge-CD28tm-
                       41BB-C D3zeta-T2A-EGFRt_epHIV7
source                 1..3273
                       mol_type = other DNA
                       organism = synthetic construct
CDS                    1..3273
SEQUENCE: 2
atgctgctgc tggtgaccag cctgctgctg tgcgagctgc ccacccccgc ctttctgctg    60
atccccatga cccagaccac ctccagcctg agcgccagcc tgggcgaccg ggtgaccatc   120
agctgccggg ccagccagga catcagcaag tacctgaact ggtatcagca gaagcccgac   180
ggcaccgtca agctgctgat ctaccacacc agccggctgc acagcggcgt gcccagccga   240
tttagcggca gcggctccgg caccgactac agcctgacca tctccaacct ggaacaggaa   300
gatatcgcca cctactttg ccagcagggc aacacactgc cctacacctt tggcggcgga    360
acaaagctgg aaatcaccgg cagcacctcc ggcagcggca gcctggcag cggcgagggc    420
agcaccaagg gcgaggtgaa gctgcaggaa agcggccctg gcctggtggc cccccagcag    480
agcctgagcg tgacctgcac cgtgagcggc gtgagcctgc ccgactacgg cgtgagctgg    540
atccggcagc ccccaggaa gggcctgaa tggctgggcg tgatctgggg cagcgagacc     600
acctactaca cagcgccct gaagagccgg ctgaccatca tcaaggacaa cagcaagagc    660
```

```
caggtgttcc tgaagatgaa cagcctgcag accgacgaca ccgccatcta ctactgcgcc    720
aagcactact actacggcgg cagctacgcc atggactact ggggccaggg caccagcgtg    780
accgtgagca gcggaggtgg tggatccgag gtgcagctgc agcagtctgg ggctgagctg    840
gtgaagcctg ggcctcagt gaagatgtcc tgcaaggctt ctggctacac atttaccagt    900
tacaatatgc actgggtaaa gcagacacct ggacagggcc tggaatggat tggagctatt    960
tatccaggaa atggtgatac ttcctacaat cagaagttca aaggcaaggc cacattgact   1020
gcagacaaat cctccagcac agcctacatg cagctcagca gcctgacatc tgaggactct   1080
gcggactatt actgtgcaag atctaattat acggtagta gctactggtt cttcgatgtc   1140
tggggcgcag ggaccacggt caccgtctcc tcaggcagta ctagcggtgg tggctccggg   1200
ggcggttccg gtggggcgg cagcagcgac attgtgctga cccaatctcc agctatccg    1260
tctgcatctc caggggagaa ggtcacaatg acttgcaggg ccagctcaag tgtaaattac   1320
atggactggt accagaagaa gccaggatcc tcccccaaac cctggattta tgccacatcc   1380
aacctggctt ctggagtccc tgctcgcttc agtggcagtg gtctgggac ctcttactct   1440
ctcacaatca gcagagttga ggctgaagat gctgccactt attactgcca gcagtggagt   1500
tttaatccac ccacgttcgg agggggacc aagctggaaa taaagagag caagtacgga   1560
ccgcccctgcc ccccttgcc tatgttctgg tgctggtgg tggtcggagg cgtgctggcc   1620
tgctacagcc tgctggtcac cgtggccttc atcatcttt gggtgaaacg gggcagaaag   1680
aaactcctgt atatattcaa acaacctttt atgaccag tacaaactac tcaagaggaa   1740
gatggctgta gctgccgatt ccagaagaa gaagaaggag gatgtgaact gcgggtgaag   1800
ttcagcagaa gcgccgacgc ccctgcctac cagcagggcc agaatcagct gtacaacgag   1860
ctgaacctgg gcagaaggga agagtacgac gtcctggata gcggagagg ccgggaccct   1920
gagatggggc gcaagcctcg gcggaagaac cccaggagga cctgtataa cgaactgcag   1980
aaagacaaga tggccgaggc ctacagcgag atcggcatga agggcgagcg gaggcggggc   2040
aagggccacg acggcctgta tcagggcctg tccaccgcca caaggatac ctacgacgcc   2100
ctgcacatga ggccctgcc cccaaggctc gaggcggcg gagagggcag aggaagtctt   2160
ctaacatgcg gtgacgtgga ggagaatccc ggccctgga tgcttctcct ggtgacaagc   2220
cttctgctct gtgagttacc acacccagca ttcctcctga tcccacgcaa agtgtgtaac   2280
ggaataggta ttggtgaatt taaagactca ctctccataa atgctacgaa tattaaacac   2340
ttcaaaaact gcacctccat cagtggcgat ctccacatcc tgccggtggc atttaggggt   2400
gactcctttca cacatactcc tcctctggat ccacaggaac tgtgatattct gaaaaccgta   2460
aaggaaatca caggtttt gctgattcag gcttggcctg aaaacaggac ggacctccat   2520
gcctttgaga acctagaaat catacgcggc aggaccaagc aacatggtca gttttctctt   2580
gcagtcgtca gcctgaacat aacatccttg ggattacgct ccctcaagga gataagtgat   2640
ggagatgtga taatttcagg aaacaaaaat ttgtgctatg caaatacaat aaactggaa   2700
aaactgtttg gaaccctccgg tcagaaaacc aaaattataa gcaacagagg tgaaaacagc   2760
tgcaaggcca caggccaggt ctgccatgcc ttgtgctccc ccgagggctg ctggggcccg   2820
gagcccaggg actgcgtctc ttgccggaat gtcagccgag gcagggaatg cgtggacaag   2880
tgcaaccttc tggaggggtga gccaaggag tttgtggaga ctctgagtg catacagtgc   2940
cacccagagt gcctgcctca ggccatgaac atcacctgca gacacggggg accagacaac   3000
tgtatccagt gtgcccacta cattgacggc ccccactgcg tcaagacctg cccggcagga   3060
gtcatgggag aaaacaacac cctggtctgg aagtacgcag acgccggcca tgtgtgccac   3120
ctgtgccatc caaactgcac ctacggatgc actgggccag tcttgaagg ctgtccaacg   3180
aatgggccta gatcccgtc atcgccact gggatggtg gggccctcct cttgctgctg   3240
gtggtggccc tggggatcgg cctcttcatg tga                                 3273

SEQ ID NO: 3           moltype = AA  length = 1090
FEATURE                Location/Qualifiers
source                 1..1090
                       mol_type = protein
                       organism = synthetic construct
SEQUENCE: 3
MLLLVTSLLL CELPHPAFLL IPMTQTTSSL SASLGDRVTI SCRASQDISK YLNWYQQKPD    60
GTVKLLIYHT SRLHSGVPSR FSGSGSGTDY SLTISNLEQE DIATYFCQQG NTLPYTFGGG   120
TKLEITGSTS GSGKPGSGEG STKGEVKLQE SGPGLVAPSQ SLSVTCTVSG VSLPDYGVSW   180
IRQPPRKGLE WLGVIWGSET TYYNSALKSR LTIIKDNSKS QVFLKMNSLQ TDDTAIYYCA   240
KHYYYGGSYA MDYWGQGTSV TVSSGGGSE VQLQQSGAEL VKPGASVKMS CKASGYTFTS   300
YNMHWVKQTP GQGLEWIGAI YPGNGDTSYN QKFKGKATLT ADKSSSTAYM QLSSLTSEDS   360
ADYYCARSNY YGSSYWFFDV WGAGTTVTVS SGSTSGGGSG GGSGGGGSSD IVLTQSPAIL   420
SASPGEKVTM TCRASSSVNY MDWYQKKPGS SPKPWIYATS NLASGVPARF SGSGSGTSYS   480
LTISRVEAED AATYYCQQWS FNPPTFGGGT KLEIKESKYG PPCPPCPMFW VLVVVGGVLA   540
CYSLLVTVAF IIFWVKRGRK KLLYIFKQPF MRPVQTTQEE DGCSCRFPEE EEGGCELRVK   600
FSRSADAPAY QQGQNQLYNE LNLGRREEYD VLDKRRGRDP EMGGKPRRKN PQEGLYNELQ   660
KDKMAEAYSE IGMKGERRRG KGHDGLYQGL STATKDTYDA LHMQALPPRL EGGGEGRGSL   720
LTCGDVEENP GPRMLLLVTS LLLCELPHPA FLLIPRKVCN GIGIGEFKDS LSINATNIKH   780
FKNCTSISGD LHILPVAFRG DSFTHTPPLD PQELDILKTV KEITGFLLIQ AWPENRTDLH   840
AFENLEIIRG RTKQHGQFSL AVVSLNITSL GLRSLKEISD GDVIISGNKN LCYANTINWK   900
KLFGTSGQKT KIISNRGENS CKATGQVCHA LCSPEGCWGP EPRDCVSCRN VSRGRECVDK   960
CNLLEGEPRE FVENSECIQC HPECLPQAMN ITCTGRGPDN CIQCAHYIDG PHCVKTCPAG  1020
VMGENNTLVW KYADAGHVCH LCHPNCTYGC TGPGLEGCPT NGPKIPSIAT GMVGALLLLL  1080
VVALGIGLFM                                                         1090

SEQ ID NO: 4           moltype = DNA  length = 582
FEATURE                Location/Qualifiers
misc_feature           1..582
                       note = IgG4hinge-CD28tm-41BB-CD3Zeta
source                 1..582
                       mol_type = other DNA
                       organism = synthetic construct
SEQUENCE: 4
```

```
gagagcaagt acggaccgcc ctgcccccct tgccctatgt tctgggtgct ggtggtggtc    60
ggaggcgtgc tggcctgcta cagcctgctg gtcaccgtgg ccttcatcat ctttttgggtg  120
aaacggggca gaaagaaact cctgtatata ttcaaacaac catttatgag accagtacaa   180
actactcaag aggaagatgg ctgtagctgc cgatttccag aagaagaaga aggaggatgt   240
gaactgcggg tgaagttcag cagaagcgcc gacgcccctg cctaccagca gggccagaat   300
cagctgtaca cgagctgaa cctgggcaga agggaagagt acgacgtcct ggataagcgg    360
agaggccggg accctgagat gggcggcaag cctcggcgga agaaccccca ggaaggcctg   420
tataacgaac tgcagaaaga caagatggcc gaggcctaca gcgagatcgg catgaagggc   480
gagcggaggc ggggcaaggg ccacgacggc ctgtatcagg gcctgtccac cgccaccaag   540
gatacctacg acgccctgca catgcaggcc ctgcccccaa gg                       582

SEQ ID NO: 5                moltype = DNA   length = 582
FEATURE                     Location/Qualifiers
misc_feature                1..582
                            note = IgG4hinge-CD28tm-41BB-CD3Zeta
source                      1..582
                            mol_type = other DNA
                            organism = synthetic construct
CDS                         1..582
SEQUENCE: 5
gagagcaagt acggaccgcc ctgcccccct tgccctatgt tctgggtgct ggtggtggtc    60
ggaggcgtgc tggcctgcta cagcctgctg gtcaccgtgg ccttcatcat ctttttgggtg  120
aaacggggca gaaagaaact cctgtatata ttcaaacaac catttatgag accagtacaa   180
actactcaag aggaagatgg ctgtagctgc cgatttccag aagaagaaga aggaggatgt   240
gaactgcggg tgaagttcag cagaagcgcc gacgcccctg cctaccagca gggccagaat   300
cagctgtaca cgagctgaa cctgggcaga agggaagagt acgacgtcct ggataagcgg    360
agaggccggg accctgagat gggcggcaag cctcggcgga agaaccccca ggaaggcctg   420
tataacgaac tgcagaaaga caagatggcc gaggcctaca gcgagatcgg catgaagggc   480
gagcggaggc ggggcaaggg ccacgacggc ctgtatcagg gcctgtccac cgccaccaag   540
gatacctacg acgccctgca catgcaggcc ctgcccccaa gg                       582

SEQ ID NO: 6                moltype = AA   length = 194
FEATURE                     Location/Qualifiers
source                      1..194
                            mol_type = protein
                            organism = synthetic construct
SEQUENCE: 6
ESKYGPPCPP CPMFWVLVVV GGVLACYSLL VTVAFIIFWV KRGRKKLLYI FKQPFMRPVQ    60
TTQEEDGCSC RFPEEEEGGC ELRVKFSRSA DAPAYQQGQN QLYNELNLGR REEYDVLDKR   120
RGRDPEMGGK PRRKNPQEGL YNELQKDKMA EAYSEIGMKG ERRRGKGHDG LYQGLSTATK   180
DTYDALHMQA LPPR                                                     194

SEQ ID NO: 7                moltype = DNA   length = 2910
FEATURE                     Location/Qualifiers
misc_feature                1..2910
                            note =
                            GMCSFRss-CD19scFv-Gly4serlinker-CD20scFv-huIgG4hinge/CH2/CH
                            3-CD28 tm/CD28cyto-41BB-CD3Zeta
source                      1..2910
                            mol_type = other DNA
                            organism = synthetic construct
SEQUENCE: 7
atgctgctgc tggtgaccag cctgctgctg tgcgagctgc cccacccgc ctttctgctg     60
atccccgaca tccagatgac ccagaccacc tccagcctga cgccagcct gggcgaccgg   120
gtgaccatca gctgccgggc cagccaggac atcagcaagt acctgaactg gtatcagcag   180
aagcccgacg gcaccgtcaa gctgctgatc taccacacca gcggctgca cagcggcgtg   240
cccagccggt ttagcggcag cggctccggc accgactaca gcctgaccat ctccaacctg   300
gaacaggaag atatcgccac ctactttttgc cagcagggca cacactgcc ctacaccttt   360
ggcggcggaa caaagctgga aatcaccggc agcacctccg gcagcggcag cgctggcagc   420
ggcgagggca gcaccaaggg cgaggtgaag ctgcaggaga gcggccctgg cctggtgcgc   480
cccagccaga gctgagcgt gacctgcacc gtgagcggcg tgagcctgcc cgactacggc   540
gtgagctgga tccggcagcc ccccaggaag ggcctggaat ggctgggcgt gatctgggc    600
agcgagacca cctactacaa cagcgccctg aagagccggc tgaccatcat caaggacaac   660
agcaagagcc aggtgttcct gaagatgaac agcctgcaga ccgacgacac cgccatctac   720
tactgcgcca gcactactac tacggcggc agctacgcca tggactactg ggcaggc       780
accagcgtga ccgtgagcag cggagtggt gatccgagg tgcagctgca gcagtctggg    840
gctgagctgg tgaagcctgg ggcctcagtg aagatgtcct gcaaggcttc tggctacaca   900
tttaccagtt acaatatgca ctgggtaaag cagacacctg gacagggcct ggaatggatt   960
ggagctattt atccaggaaa tggtgatact tcctacaatc agaagttcaa aggcaaggcc  1020
acattgactg cagacaaatc ctccagcaca gcctacatgc agctcagcag cctgacatct  1080
gaggactctg cggactatta ctgtgcaaga tctaattatt acggtagtag ctactggttc  1140
ttcgatgtct ggggcgcagg gaccacggtc accgtctcct caggcagtac tagcggtggt  1200
ggctccgggg gcggttccgg tgggggcggc agcagcgaca ttgtgctgac ccaatctcca  1260
gctatcctgt ctgcatctcc aggggagaag gtcacaatga cttgcagggc cagctcaagt  1320
gtaaattaca tggactggta ccagaagaag ccaggatcct cccccaaacc ctggatttat  1380
gccacatcca acctggcttc tggagtccct gctcgcttca gtggcagtgg gtctgggacc  1440
tcttactctc tcacaatcag cagagtggag gctgaagatg ctgccactta ttactgccag  1500
cagtggagtt ttaatccacc cacgttcgga gggggcacca agctggaaat aaaagagagc  1560
aagtacggac cgccctgccc cccttgccct gcccccgagt tcctgggcgg acccagcgtg  1620
```

-continued

```
ttcctgttcc cccccaagcc caaggacacc ctgatgatca gccggacccc cgaggtgacc 1680
tgcgtggtgg tggacgtgag ccaggaagat cccgaggtcc agttcaattg gtacgtggac 1740
ggcgtggaag tgcacaacgc caagaccaag cccagagagg aacagttcaa cagcacctac 1800
cgggtggtgt ctgtgctgac cgtgctgcac caggactggc tgaacggcaa agaatacaag 1860
tgcaaggtgt ccaacaaggg cctgcccagc agcatcgaaa agaccatcag caaggccaag 1920
ggccagcctc gcgagcccca ggtgtacacc ctgcctccct cccaggaaga gatgaccaag 1980
aaccaggtgt ccctgacctg cctggtgaag ggcttctacc ccagcgacat cgccgtggag 2040
tgggagagca cgaccagcc tgagaacaac tacaagacca cccctcccgt gctggacagc 2100
gacggcagct tcttcctgta cagccggctg accgtggaca agagccggtg gcaggaaggc 2160
aacgtctttta gctgcagcgt gatgcacgag gcctgcaca accactacac ccagaagagc 2220
ctgagcctgt ccctgggcaa gatgttctgg gtgctggtgg tggtgggcgg ggtgctggcc 2280
tgctacagcc tgctggtgac agtggccttc atcatctttt gggtgcggag caagcggagc 2340
agaggcggcc acagcgacta catgaacatg ccccccagac ggcctggccc cacccggaag 2400
cactaccagc cctacgcccc acccagggac tttgccgcct acagaagcaa acggggcaga 2460
aagaaactcc tgtatatatt caaacaacca tttatgagac cagtacaaac tactcaagag 2520
gaagatggct gtagctgccg atttccagaa gaagaagaag gaggatgtga actgcgggtg 2580
aagttcagca gaagcgccga cgcccctgcc taccagcagg ccagaatca gctgtacaac 2640
gagctgaacc tgggcagaag ggaagagtac gacgtcctgg ataagcggag aggccgggac 2700
cctgagatgg gcggcaagcc tcggcggaag aaccccccagg aaggcctgta taacgaactg 2760
cagaaagaca agatggccga ggcctacagc gagatcggca tgaagggcga gcggaggcgg 2820
ggcaagggcc acgacggcct gtatcagggc ctgtccaccg ccaccaagga tacctacgac 2880
gccctgcaca tgcaggccct gccccaagg                                   2910
```

```
SEQ ID NO: 8            moltype = DNA   length = 2910
FEATURE                 Location/Qualifiers
misc_feature            1..2910
                        note =
                        GMCSFR-ssCD19scFv-Gly4serlinker-CD20scFv-huIgG4hinge/CH2/CH
                        3-CD28 tm/CD28cyto-41BB-CD3Zeta
source                  1..2910
                        mol_type = other DNA
                        organism = synthetic construct
CDS                     1..2910
SEQUENCE: 8
```

```
atgctgctgc tggtgaccag cctgctgctg tgcgagctgc cccacccgc ctttctgctg 60
atccccgaca tccagatgac ccagaccacc tccagcctga cgccagcct gggcgaccgg 120
gtgaccatca gctgccgggc cagcaggac atcagcaagt acctgaactg gtatcagcag 180
aagcccgacg gcaccgtcaa gctgctgatc taccacacca gccggctgca cagcggcgtg 240
cccagccggt ttagcggcag cggctccggc accgactca ctccaacctg 300
gaacaggaag atatcgccac ctactttgc cagcagggca acacactgcc ctacacctt 360
ggcggcggaa caaagctgga aatcaccggc agcacctccg gcagcggcaa gcctggcagc 420
ggcgagggca gcaccaaggg cgaggtgaag ctgcaggaaa gcggccctgg cctggtggcc 480
cccagccaga gcctgagcgt gacctgcacc gtgagcggcg tgagcctggc cgactactgg 540
gtgagctgga tccggcagcc ccccaggaag ggcctggaat ggctgggcgt gatctggggc 600
agcgagacca cctactacaa cagcgccctg aagagccggc tgaccatcat caaggacaac 660
agcaagagcc aggtgttcct gaagatgaac agcctgcaga ccgacgacac cgccatctac 720
tactgcgcca agcactacta ctacggcggc agctacgcca tggactactg gggccaggggc 780
accagcgtga ccgtgagcag cggaggtggt ggatccgagg tgcagctgca gcagtctggg 840
gctgagctgg tgaagcctgg ggcctcagtg aagatgtcct gcaaggcttc tggctacaca 900
tttaccagtt acaatatgca ctgggtaaag cagacacctg gacagggcct ggaatggatt 960
ggagctattt atccaggaaa tggtgatact tcctacaatc agaagttcaa aggcaaggcc 1020
acattgactg cagacaaatc ctccagcaca gcctacatgc agctcagcag cctgacatct 1080
gaggactctg cggactatta ctgtgcaaga tctaattatt acggtagtag ctactggttc 1140
ttcgatgtct ggggcgcagg gaccacggtc accgtctcct caggcagtac tagcggtggt 1200
ggctccgggg gcggttccgg tggggcggc agcagcgaca ttgtgctgac ccaatctcca 1260
gctatcctgt ctgcatctcc aggggagaag gtcacaatga cttgcagggc cagctcaagt 1320
gtaaattaca tggactggta ccagaagaag ccaggatcct cccccaaacc ctggatttat 1380
gccacatcca acctggcttc tggagtccct gctcgcttca gtggcagtgg gtctgggacc 1440
tcttactctc tcacaatcag cagagtggag gctgaagatg ctgccactta ttactgccag 1500
cagtggagtt ttaatccacc cacgttcgga ggggggacca agctggaaat aaaagagagc 1560
aagtacggac cgcccctgcc cccttgcccc gcccccgagt tcctgggcgg accagcgtg 1620
ttcctgttcc cccccaagcc caaggacacc ctgatgatca gccggacccc cgaggtgacc 1680
tgcgtggtgg tggacgtgag ccaggaagat cccgaggtcc agttcaattg gtacgtggac 1740
ggcgtggaag tgcacaacgc caagaccaag cccagagagg aacagttcaa cagcacctac 1800
cgggtggtgt ctgtgctgac cgtgctgcac caggactggc tgaacggcaa agaatacaag 1860
tgcaaggtgt ccaacaaggg cctgcccagc agcatcgaaa agaccatcag caaggccaag 1920
ggccagcctc gcgagcccca ggtgtacacc ctgcctccct cccaggaaga gatgaccaag 1980
aaccaggtgt ccctgacctg cctggtgaag ggcttctacc ccagcgacat cgccgtggag 2040
tgggagagca cgaccagcc tgagaacaac tacaagacca cccctcccgt gctggacagc 2100
gacggcagct tcttcctgta cagccggctg accgtggaca agagccggtg gcaggaaggc 2160
aacgtctttta gctgcagcgt gatgcacgag gcctgcaca accactacac ccagaagagc 2220
ctgagcctgt ccctgggcaa gatgttctgg gtgctggtgg tggtgggcgg ggtgctggcc 2280
tgctacagcc tgctggtgac agtggccttc atcatctttt gggtgcggag caagcggagc 2340
agaggcggcc acagcgacta catgaacatg ccccccagac ggcctggccc cacccggaag 2400
cactaccagc cctacgcccc acccagggac tttgccgcct acagaagcaa acggggcaga 2460
aagaaactcc tgtatatatt caaacaacca tttatgagac cagtacaaac tactcaagag 2520
gaagatggct gtagctgccg atttccagaa gaagaagaag gaggatgtga actgcgggtg 2580
aagttcagca gaagcgccga cgcccctgcc taccagcagg ccagaatca gctgtacaac 2640
gagctgaacc tgggcagaag ggaagagtac gacgtcctgg ataagcggag aggccgggac 2700
```

-continued

```
cctgagatgg gcggcaagcc tcggcggaag aacccccagg aaggcctgta taacgaactg    2760
cagaaagaca agatggccga ggcctacagc gagatcggca tgaagggcga gcggaggcgg    2820
ggcaagggcc acgacggcct gtatcagggc ctgtccaccg ccaccaagga tacctacgac    2880
gccctgcaca tgcaggccct gcccccaagg                                     2910
```

SEQ ID NO: 9          moltype = AA  length = 970
FEATURE               Location/Qualifiers
source                1..970
                      mol_type = protein
                      organism = synthetic construct
SEQUENCE: 9
```
MLLLVTSLLL CELPHPAFLL IPDIQMTQTT SSLSASLGDR VTISCRASQD ISKYLNWYQQ     60
KPDGTVKLLI YHTSRLHSGV PSRFSGSGSG TDYSLTISNL EQEDIATYFC QQGNTLPYTF    120
GGGTKLEITG STSGSGKPGS GEGSTKGEVK LQESGPGLVA PSQSLSVTCT VSGVSLPDYG    180
VSWIRQPPRK GLEWLGVIWG SETTYYNSAL KSRLTIIKDN SKSQVFLKMN SLQTDDTAIY    240
YCAKHYYYGG SYAMDYWGQG TSVTVSSGGG GSEVQLQQSG AELVKPGASV KMSCKASGYT    300
FTSYNMHWVK QTPGQGLEWI GAIYPGNGDT SYNQKFKGKA TLTADKSSST AYMQLSSLTS    360
EDSADYYCAR SNYYGSSYWF FDVWGAGTTV TVSSGSTSGG GSGGGSGGG SSDIVLTQSP    420
AILSASPGEK VTMTCRASSS VNYMDWYQKK PGSSPKPWIY ATSNLASGVP ARFSGSGSGT    480
SYSLTISRVE AEDAATYYCQ QWSFNPPTFG GGTKLEIKES KYGPPCPPCP APEFLGPSV    540
FLFPPKPKDT LMISRTPEVT CVVVDVSQED PEVQFNWYVD GVEVHNAKTK PREEQFNSTY    600
RVVSVLTVLH QDWLNGKEYK CKVSNKGLPS SIEKTISKAK GQPREPQVYT LPPSQEEMTK    660
NQVSLTCLVK GFYPSDIAVE WESNGQPENN YKTTPPVLDS DGSFFLYSRL TVDKSRWQEG    720
NVFSCSVMHE ALHNHYTQKS LSLSLGKMFW VLVVVGGVLA CYSLLVTVAF IIFWVRSKRS    780
RGGHSDYMNM TPRRPGPTRK HYQPYAPPRD FAAYRSKRGR KKLLYIFKQP FMRPVQTTQE    840
EDGCSCRFPE EEEGGCELRV KFSRSADAPA YQQGQNQLYN ELNLGRREEY DVLDKRRGRD    900
PEMGGKPRRK NPQEGLYNEL QKDKMAEAYS EIGMKGERRR GKGHDGLYQG LSTATKDTYD    960
ALHMQALPPR                                                           970
```

SEQ ID NO: 10         moltype = DNA  length = 3402
FEATURE               Location/Qualifiers
misc_feature          1..3402
                      note =
                      GMCSFRss-CD19scFv-Gly4serlinker-CD20scFv-CD8alphaHinge-CD8a
                      lphaTM-41BB-CD3Zeta-T2A-EGFRt
source                1..3402
                      mol_type = other DNA
                      organism = synthetic construct
SEQUENCE: 10
```
atgctgctgc tggtgaccag cctgctgctg tgcgagctgc ccacccccgc ctttctgctg      60
atccccgaca tccagatgac ccagaccacc tccagcctga gcgccagcct gggcgaccgg    120
gtgaccatca gctgccgggc cagccaggac atcagcaagt acctgaactg gtatcagcag    180
aagcccgacg gcaccgtcaa gctgctgatc taccacagca gccgcctgca cagcggcgtg    240
cccagccggt ttagcggcag cggctccggc accgactaca gcctgaccat ctccaacctg    300
gaacaggaag atatcgccac ctacttttgc cagcagggca cacactgcc ctacaccttt    360
ggcggcggaa caaagctgga aatcaccggc agcacctccg gcagcggcaa gcctggcagc    420
ggcgagggca gcaccaaggg cgaggtgaag ctgcaggaaa gcggccctgg cctggtggcc    480
cccagccaga gcctgagcgt gacctgcacc gtgagcggcg tgagcctgcc cgactacggc    540
gtgagctgga tccggcagcc ccccaggaag ggcctggaat ggctgggcgt gatctggggc    600
agcgagacca cctactacaa cagcgccctg aagagccggc tgaccatcat caaggacaac    660
agcaaggcc aggtgttcct gaagatgaac agcctgcaga ccgacgacac ggccatctac    720
tactgcgcca agcactacta ctacggcggc agctacgcca tggactactg gggccagggc    780
accagcgtga ccgtgagcag cggaggtggt ggatccgagg tgcagctgca gcagtctggg    840
gctgagctgt gaagcctgg ggcctcagtg aagatgtcct gcaaggcttc tggctacaca    900
tttaccagtt acaatatgca ctgggtaaag cagacacctg gacagggcct ggaatggatt    960
ggagctattt atccaggaaa tggtgatact tcctacaatc agaagttcaa aggcaaggcc   1020
acattgactg cagacaaatc ctccagcaca gcctacatgc agctcagcag cctgacatct   1080
gaggactctg cggactatta ctgtgcaaga tctaattatt acggtagtag ctactggttc   1140
ttcgatgtct ggggcgcagg gaccacggtc accgtctcct caggcagtac tagcggtggt   1200
ggctccgggg gcggttccgg tgggggcggc agcagcgaca ttgtgctgac ccaatctcca   1260
gctatcctgt ctgcatctcc aggggagaag gtcacaatga cttgcagggc cagctcaagt   1320
gtaaattaca tggactggta ccagaagaag ccaggatcct cccccaaacc ctggatttat   1380
gccacatcca acctggcttc tggagtccct gctcgcttca gtggcagtgg gtctgggacc   1440
tcttactctc tcacaatcag cagagtggag gctgaagatg ctgccactta ttactgccaa   1500
cagtggagtt ttaatccacc cacgttcgga gggggaccaa gctggaaat aaaagagagc   1560
aagtacggac cgccctgccc cccttgccct aagcctacca cccctgc cctagacct   1620
ccaacacccg cccaacaat cgccagccag cctctgtctc tgaggcccga ggcttgtaga   1680
ccagctgctg gcggagccgt gcacaccaga ggactggatt tcgcctgcga catctacatc   1740
tgggccctc tggccggcac atgtggcgtg ctgctgctga gcctcgtgat caccagcgc   1800
ggcagaaaga aactgctgta catctttaag cagcccttca tgcggcccgt gcagaccacc   1860
caggaagagg acggctgctc ctgcagattc cccgaggaag aagaaggcgg ctgcgagctg   1920
agagtgaagt tcagcagatc cgccgacgcc ctgcctaccc agcagggaca gaaccagctg   1980
tacaacagc tgaacctggg cagacgggaa gagtacgacg tgctggacaa gcggagaggc   2040
cgggacccg agatgggcgg aaagcccaga agaaagaacc ccaggaag cctgtataac   2100
gaactgcaga agacaagat ggccgaggcc tacagcgaga tcggaatgaa gggcgagcgg   2160
agaagaggca agggccacga tggcctgtac cagggcctga gcaccgccac caaggacacc   2220
tatgacgccc tgcacatgca ggccctgcct ccaagactcg agggcggcgg agagggcaga   2280
ggaagtcttc taacatgcgg tgacgtggag gagaatcccg gccctaggat gcttctcctg   2340
gtgacaagcc ttctgctctg tgagttacca cacccagcat tcctcctgat cccacgcaaa   2400
```

```
gtgtgtaacg gaataggtat tggtgaattt aaagactcac tctccataaa tgctacgaat   2460
attaaacact tcaaaaactg cacctccatc agtggcgatc tccacatcct gccggtggca   2520
tttaggggtg actccttcac acatactcct cctctggatc cacaggaact ggatattctg   2580
aaaaccgtaa aggaaatcac agggttttg ctgattcagg cttggcctga aaacaggacg    2640
gacctccatg cctttgagaa cctagaaatc atacgcggca ggaccaagca acatggtcag   2700
ttttctcttg cagtcgtcag cctgaacata acatccttgg gattacgctc cctcaaggag   2760
ataagtgatg gagatgtgat aatttcagga aacaaaaatt tgtgctatgc aaatacaata   2820
aactggaaaa aactgtttgg gacctccggt cagaaaacca aaattataag caacagaggt   2880
gaaaacagct gcaaggccac aggccaggtc tgccatgcct tgtgctcccc cgagggctgc   2940
tggggcccgg agcccaggga ctgcgtctct gccggaatg tcagccgagg cagggaatgc    3000
gtggacaagt gcaaccttct ggagggtgag ccaaggggagt ttgtggagaa ctctgagtgc   3060
atacagtgcc acccagagtg cctgcctcag gccatgaaca tcacctgcac aggacgggga   3120
ccagacaact gtatccagtg tgcccactac attgacggcc ccactgcgt caagacctgc    3180
ccggcaggag tcatgggaga aaacaaccac ctggtctgaa agtacgcaga cgccggccat   3240
gtgtgccacc tgtgccatcc aaactgcacc tacggatgca ctgggccagg tcttgaaggc   3300
tgtccaacga atgggcctaa gatcccgtcc atcgccactg ggatggtggg ggccctcctc   3360
ttgctgctgg tggtggccct ggggatcggc ctcttcatgt ga                      3402

SEQ ID NO: 11           moltype = DNA   length = 3402
FEATURE                 Location/Qualifiers
misc_feature            1..3402
                        note =
                        GMCSFRss-CD19scFv-Gly4serlinker-CD20scFv-CD8alphaHinge-CD8a
                        lphaTM -41BB-CD3Zeta-T2A-EGFRt
source                  1..3402
                        mol_type = other DNA
                        organism = synthetic construct
CDS                     1..3402
SEQUENCE: 11
atgctgctgc tggtgaccag cctgctgctg tgcgagctgc cccacccgc ctttctgctg    60
atccccgaca tccagatgac ccagaccacc tccagcctga cgccagcct gggcgaccgg    120
gtgaccatca gctgccgggc cagccaggac atcagcaagt acctgaactg gtatcagcag   180
aagcccgacg gcaccgtcaa gctgctgatc taccacacca gccggctgca cagcggcgtg   240
cccagccggt ttagcggcag cggctccggc accgactaca gcctcaacctg             300
gaacaggaag atatcgccac ctactttttgc cagcagggca cacactgcc ctacacccttt  360
ggcggcggaa caaagctgga aatcaccggc agcacctccg gcagcggcaa gcctggcagc   420
ggcgagggca gcaccaaggg cgaggtgaag ctgcaggaaa gcggcctgg cctggtggcc   480
cccagccaga gcctgagcgt gacctgcacc gtgagcggc tgagcctgcc cgactacggc   540
gtgagctgga tccggcagcc cccccaggaag ggcctgaat ggctgggcgt gatctggggc   600
agcgagacca cctactacaa cagcgccctg aagagccggc tgaccatcat caaggacaac   660
agcaagagcc aggtgttcct gaagatgaac agcctgcaga ccgacgacac cgccatctac   720
tactgcgcca gcactacta ctacggcggc agctacgcca tggactactg ggccagggc    780
accagcgtga ccgtgagcag cggaggtggt ggatccgaa tgcagctgca cagtctggg    840
gctgagctgg tgaagcctgg ggcctcagtg aagatgtcct gcaaggcttc tggctacaca   900
tttaccagtt acaatatgca ctgggtaaag cagacacctg acaggcct ggaatggatt     960
ggagctattt atccaggaaa tggtgatact tcctacaatc agaagttcaa aggcaaggcc   1020
acattgactg cagacaaatc ctccagcaca gcctacatgc agctcagcag cctgacatct   1080
gaggactctg cggactatta ctgtgcaaga tctaattatt acggtagtag ctactggttc   1140
ttcgatgtct ggggcgcagg gaccacggt accgtctcct caggcagtac tagcggtggt   1200
ggctccgggg gcggttccgg tggggcggc agcagcgaca ttgtgctgac caatctcca    1260
gctatctgt ctgcatctcc agggggaaag gtcacaatga cttgcagggc cagctcaagt   1320
gtaaattaca tggactggta ccagaagaag ccaggatcct cccccaaacc ctggatttat   1380
gccacatcca acctggcttc tggagtccct gctcgcttca gtggcagtgg gtctgggacc   1440
tcttactctc tcacaatcag cagagtggag gctgaagatg ctgccactta ttactgccag   1500
cagtggagtt taatccacc cacgttcgga ggggggacca agctggaaat aaaagagagc   1560
aagtacggac cgcctgcc cccttgccct aagcctacca ccaccctgc ccctagacct    1620
ccaacacccg cccaacaat cgccagccag cctctgtctc tgaggccga ggcttgtaga   1680
ccagctgctg gcggagccgt gcacaccaga ggactggatt tcgcctgcga catctacatc   1740
tgggccctc tggccggcac atgtggcgtg ctgctgctga gcctcgtgat caccaagcgg   1800
ggcagaaaga aactgctgta catcttttaag cagccctca tgcggccgt gcagaccacc   1860
caggaagagg acggctgctc ctgcagattc cccgaggaag aagaaggcgg ctgcgagctg   1920
agagtgaagt tcagcagatc cgccgacgcc cctgcctacc agcagggaca gaaccagctg   1980
tacaacgagc tgaacctggg cagacgggaa gagtacgacg tgctggacaa gcggagaggc   2040
cgggaccctg agatgggcgg aaagcccaga agaaagaacc ccaggaagtg cctgtataac   2100
gaactgcaga agacaagat ggccgaggcc tacagcgaga tcggaatgaa gggcgagcgg   2160
agaagaggca aggccacga tggcctgtac caggcctga gcaccgccac caaggacacc   2220
tatgacgccc tgcacatgca ggccctgcct ccaagactcg agggcggcgg agagggcaga   2280
ggaagtcttc taacatgcgg tgacgtggag gagaatcccg gccctaggat gcttctcctg   2340
gtgacaagcc ttctgctctg tgagttacca cacccagcat cctcctgat ccacgcaa     2400
gtgtgtaacg gaataggtat tggtgaattt aaagactcac tctccataaa tgctacgaat   2460
attaaacact tcaaaaactg cacctccatc agtggcgatc tccacatcct gccggtggca   2520
tttaggggtg actccttcac acatactcct cctctggatc cacaggaact ggatattctg   2580
aaaaccgtaa aggaaatcac agggttttg ctgattcagg cttggcctga aaacaggacg    2640
gacctccatg cctttgagaa cctagaaatc atacgcggca ggaccaagca acatggtcag   2700
ttttctcttg cagtcgtcag cctgaacata acatccttgg gattacgctc cctcaaggag   2760
ataagtgatg gagatgtgat aatttcagga aacaaaaatt tgtgctatgc aaatacaata   2820
aactggaaaa aactgtttgg gacctccggt cagaaaacca aaattataag caacagaggt   2880
gaaaacagct gcaaggccac aggccaggtc tgccatgcct tgtgctcccc cgagggctgc   2940
tggggcccgg agcccaggga ctgcgtctct gccggaatg tcagccgagg cagggaatgc    3000
```

-continued

```
gtggacaagt gcaaccttct ggagggtgag ccaagggagt tgtggagaaa ctctgagtgc   3060
atacagtgcc acccagagtg cctgcctcag gccatgaaca tcacctgcac aggacgggga   3120
ccagacaact gtatccagtg tgcccactac attgacggcc cccactcgt caagacctgc    3180
ccggcaggag tcatgggaga aaacaacacc ctggtctgga agtacgcaga cgccggccat   3240
gtgtgccacc tgtgccatcc aaactgcacc tacggatgca ctggccaggg tcttgaaggc   3300
tgtccaacga atgggcctaa gatcccgtcc atcgccactg ggatggtggg ggccctcctc   3360
ttgctgctgg tggtggcccct ggggatcggc ctcttcatgt ga                     3402

SEQ ID NO: 12           moltype = AA   length = 1133
FEATURE                 Location/Qualifiers
source                  1..1133
                        mol_type = protein
                        organism = synthetic construct
SEQUENCE: 12
MLLLVTSLLL CELPHPAFLL IPDIQMTQTT SSLSASLGDR VTISCRASQD ISKYLNWYQQ     60
KPDGTVKLLI YHTSRLHSGV PSRFSGSGSG TDYSLTISNL EQEDIATYFC QQGNTLPYTF    120
GGGTKLEITG STSGSGKPGS GEGSTKGEVK LQESGPGLVA PSQSLSVTCT VSGVSLPDYG    180
VSWIRQPPRK GLEWLGVIWG SETTYYNSAL KSRLTIIKDN SKSQVFLKMN SLQTDDTAIY    240
YCAKHYYYGG SYAMDYWGQG TSVTVSSGGG GSEVQLQQSG AELVKPGASV KMSCKASGYT    300
FTSYNMHWVK QTPGQGLEWI GAIYPGNGDT SYNQKFKGKA TLTADKSSST AYMQLSSLTS    360
EDSADYYCAR SNYYGSSYWF FDVWGAGTTV TVSSGSTSGG GSGGGSGGG SSDIVLTQSP    420
AILSASPGEK VTMTCRASSS VNYMDWYQKK PGSSPKPWIY ATSNLASGVP ARFSGSGSGT    480
SYSLTISRVE AEDAATYYCQ QWSFNPPTFG GGTKLEIKES KYGPPCPPCP KPTTTPAPRP    540
PTPAPTIASQ PLSLRPEACR PAAGGAVHTR GLDFACDIYI WAPLAGTCGV LLLSLVITKR    600
GRKKLLYIFK QPFMRPVQTT QEEDGCSCRF PEEEEGGCEL RVKFSRSADA PAYQQGQNQL    660
YNELNLGRRE EYDVLDKRRG RDPEMGGKPR RKNPQEGLYN ELQKDKMAEA YSEIGMKGER    720
RRGKGHDGLY QGLSTATKDT YDALHMQALP PRLEGGGEGR GSLLTCGDVE ENPGPRMLLL    780
VTSLLLCELP HPAFLLIPRK VCNGIGIGEF KDSLSINATN IKHFKNCTSI SGDLHILPVA    840
FRGDSFTHTP PLDPQELDIL KTVKEITGFL LIQAWPENRT DLHAFENLEI IRGRTKQHGQ    900
FSLAVVSLNI TSLGLRSLKE ISDGDVIISG NKNLCYANTI NWKKLFGTSG QKTKIISNRG    960
ENSCKATGQV CHALCSPEGC WGPEPRDCVS CRNVSRGREC VDKCNLLEGE PREFVENSEC   1020
IQCHPECLPQ AMNITCTGRG PDNCIQCAHY IDGPHCVKTC PAGVMGENNT LVWKYADAGH   1080
VCHLCHPNCT YGCTGPGLEG CPTNGPKIPS IATGMVGALL LLLVVALGIG LFM          1133

SEQ ID NO: 13           moltype = DNA   length = 1146
FEATURE                 Location/Qualifiers
misc_feature            1..1146
                        note = T2A-EGFRt
source                  1..1146
                        mol_type = other DNA
                        organism = synthetic construct
SEQUENCE: 13
ctcgagggcg gcggagaggg cagaggaagt cttctaacat gcggtgacgt ggaggagaat     60
cccggcccta ggatgcttct cctggtgaca agccttctgc tctgtgagtt accacaccca    120
gcattcctcc tgatcccacg caaagtgtgt aacggaatag gtattggtga atttaaagac    180
tcactctcca taaatgctac gaatattaaa cacttcaaaa actgcacctc catcagtggc    240
gatctccaca tcctgccggt ggcatttagg ggtgactcct tcacacatac tcctcctctg    300
gatccacagg aactggatat tctgaaaacc gtaaaggaaa tcacagggtt tttgctgatt    360
caggcttggc ctgaaaacag gacggacctc catgcctttg agaacctaga aatcatacgc    420
ggcaggacca agcaacatgg tcagtttttct cttgcagtcg tcagcctgaa cataacatcc    480
ttgggattac gctccctcaa ggagataagt gatggagatg tgataatttc aggaaacaaa    540
aatttgtgct atgcaaatac aataaactgg aaaaaactgt ttgggacctc cggtcagaaa    600
accaaaatta taagcaacag aggtgaaaac agctgcaagg ccacaggcca ggtctgccat    660
gccttgtgct ccccccgaggg ctgctgggcc cggagcccca gggactgcgt ctcttgccgg    720
aatgtcagcc gagggcaggga atgcgtagac aagtgcaacc ttctggaggg tgagccaagg    780
gagtttgtgg agaactctga gtgcatacag tgccacccag agtgcctgcc tcaggccatg    840
aacatcacct gcacaggacg ggaccagac aactgtatcc agtgtgccca ctacattgac    900
ggccccccact cgtcaagac ctgccggca ggagtcatgg gagaaaacaa cacccctggc    960
tggaagtacg cagacgccgg ccatgtgtgc cacctgtgcc atccaaactg cacctacgga   1020
tgcactgggc caggtcttga aggctgtcca acgaatgggc ctaagatccc gtccatcgcc   1080
actgggatgg tggggggccccc cctcttgctg ctggtggtgg ccctggggat cggcctcttc   1140
atgtga                                                              1146

SEQ ID NO: 14           moltype = DNA   length = 1146
FEATURE                 Location/Qualifiers
misc_feature            1..1146
                        note = T2A-EGFRt
source                  1..1146
                        mol_type = other DNA
                        organism = synthetic construct
CDS                     1..1146
SEQUENCE: 14
ctcgagggcg gcggagaggg cagaggaagt cttctaacat gcggtgacgt ggaggagaat     60
cccggcccta ggatgcttct cctggtgaca agccttctgc tctgtgagtt accacaccca    120
gcattcctcc tgatcccacg caaagtgtgt aacggaatag gtattggtga atttaaagac    180
tcactctcca taaatgctac gaatattaaa cacttcaaaa actgcacctc catcagtggc    240
gatctccaca tcctgccggt ggcatttagg ggtgactcct tcacacatac tcctcctctg    300
gatccacagg aactggatat tctgaaaacc gtaaaggaaa tcacagggtt tttgctgatt    360
caggcttggc ctgaaaacag gacggacctc catgcctttg agaacctaga aatcatacgc    420
```

```
ggcaggacca agcaacatgg tcagttttct cttgcagtcg tcagcctgaa cataacatcc   480
ttgggattac gctccctcaa ggagataagt gatggagatg tgataatttc aggaaacaaa   540
aatttgtgct atgcaaatac aataaactgg aaaaaactgt ttgggacctc cggtcagaaa   600
accaaaatta taagcaacag aggtgaaaac agctgcaagg ccacaggcca ggtctgccat   660
gcctttgtgct cccccgaggg ctgctggggc ccggagccca gggactgcgt ctcttgccgg   720
aatgtcagcc gaggcaggga atgcgtggac aagtgcaacc ttctggaggg tgagccaagg   780
gagtttgtgg agaactctga gtgcatacag tgccacccag agtgcctgcc tcaggccatg   840
aacatcacct gcacaggacg gggaccagac aactgtatcc agtgtgccca ctacattgac   900
ggcccccact gcgtcaagac ctgcccggca ggagtcatgg gagaaaacaa cccctggtc    960
tggaagtacg cagacgccgg ccatgtgtgc cacctgtgcc atccaaactg cacctacgga  1020
tgcactgggc caggtcttga aggctgtcca acgaatgggc ctaagatccc gtccatcgcc  1080
actgggatgg tgggggccct cctcttgctg ctggtggtgg ccctggggat cggcctcttc  1140
atgtga                                                             1146

SEQ ID NO: 15           moltype = AA  length = 381
FEATURE                 Location/Qualifiers
source                  1..381
                        mol_type = protein
                        organism = synthetic construct
SEQUENCE: 15
LEGGGEGRGS LLTCGDVEEN PGPRMLLLVT SLLLCELPHP AFLLIPRKVC NGIGIGEFKD   60
SLSINATNIK HFKNCTSISG DLHILPVAFR GDSFTHTPPL DPQELDILKT VKEITGFLLI  120
QAWPENRTDL HAFENLEIIR GRTKQHGQFS LAVVSLNITS LGLRSLKEIS DGDVIISGNK  180
NLCYANTINW KKLFGTSGQK TKIISNRGEN SCKATGQVCH ALCSPEGCWG PEPRDCVSCR  240
NVSRGRECVD KCNLLEGEPR EFVENSECIQ CHPECLPQAM NITCTGRGPD NCIQCAHYID  300
GPHCVKTCPA GVMGENNTLV WKYADAGHVC HLCHPNCTYG CTGPGLEGCP TNGPKIPSIA  360
TGMVGALLLL LVVALGIGLF M                                            381

SEQ ID NO: 16           moltype = AA  length = 10
FEATURE                 Location/Qualifiers
source                  1..10
                        mol_type = protein
                        organism = synthetic construct
SEQUENCE: 16
GGGGSGGGGS                                                          10

SEQ ID NO: 17           moltype = AA  length = 8
FEATURE                 Location/Qualifiers
source                  1..8
                        mol_type = protein
                        organism = synthetic construct
VARIANT                 2
                        note = X is Val or Ile.
UNSURE                  4
SEQUENCE: 17
DXEXNPGP                                                             8
```

What is claimed is:

1. A bispecific chimeric antigen receptor (CAR), comprising:
   a. two antigen-specific targeting regions;
   b. a CD8a hinge extracellular spacer domain;
   c. a CD8a transmembrane domain;
   d. a 4-1BB co-stimulatory domain; and
   e. CD3 zeta intracellular signaling domain wherein each antigen-specific targeting region comprises an antigen-specific single-domain antibody, a variable domain, a VH domain, or a full length heavy chain.

2. The bispecific CAR of claim 1, wherein each antigen-specific targeting region binds a different antigen.

3. The bispecific CAR of claim 1, wherein each antigen-specific targeting region comprises an antigen-specific single-domain antibody that is a variable domain of a heavy chain that is alone sufficient to confer antigen specificity.

4. The bispecific CAR of claim 1, wherein each antigen-specific targeting region comprises an antigen-specific variable domain.

5. The bispecific CAR of claim 1, wherein each antigen-specific targeting region comprises an antigen-specific VH domain.

6. The bispecific CAR of claim 3, wherein the two antigen-specific targeting regions bind an antigen specific for cancer.

7. The bispecific CAR of claim 4, wherein the two antigen-specific targeting regions bind an antigen specific for cancer.

8. The bispecific CAR of claim 5, wherein the two antigen-specific targeting regions bind an antigen specific for cancer.

9. The bispecific CAR of claim 3, wherein the two antigen-specific targeting regions bind to an antigen specifically expressed on cells associated with a hematological disease.

10. The bispecific CAR of claim 4, wherein the two antigen-specific targeting regions bind to an antigen specifically expressed on cells associated with a hematological disease.

11. The bispecific CAR of claim 5, wherein the two antigen-specific targeting regions bind to an antigen specifically expressed on cells associated with a hematological disease.

12. The bispecific CAR of claim 6, wherein the two antigen-specific targeting regions bind to an antigen specifically expressed on B-cell lineage tumor cells.

13. The bispecific CAR of claim 7, wherein the two antigen-specific targeting regions bind to an antigen specifically expressed on B-cell lineage tumor cells.

14. The bispecific CAR of claim 8, wherein the two antigen-specific targeting regions bind to an antigen specifically expressed on B-cell lineage tumor cells.

15. The bispecific CAR of claim 3, wherein the two antigen-specific targeting regions bind to an antigen specifically expressed on immune cells.

16. The bispecific CAR of claim 4, wherein the two antigen-specific targeting regions bind to an antigen specifically expressed on immune cells.

17. The bispecific CAR of claim 5, wherein the two antigen-specific targeting regions bind to an antigen specifically expressed on immune cells.

18. The bispecific CAR of claim 15, wherein the two antigen-specific targeting regions bind to an antigen specifically expressed on plasma cells.

19. The bispecific CAR of claim 16, wherein the two antigen-specific targeting regions bind to an antigen specifically expressed on plasma cells.

20. The bispecific CAR of claim 17, wherein the two antigen-specific targeting regions bind to an antigen specifically expressed on plasma cells.

21. The bispecific CAR of claim 18, wherein the two antigen-specific targeting regions bind to an antigen specifically expressed on cancerous plasma cells.

22. The bispecific CAR of claim 19, wherein the two antigen-specific targeting regions bind to an antigen specifically expressed on cancerous plasma cells.

23. The bispecific CAR of claim 20, wherein the two antigen-specific targeting regions bind to an antigen specifically expressed on cancerous plasma cells.

24. The bispecific CAR of claim 3, wherein the two antigen-specific targeting regions are arranged in tandem and are separated by a linker peptide.

25. The bispecific CAR of claim 4, wherein the two antigen-specific targeting regions are arranged in tandem and are separated by a linker peptide.

26. The bispecific CAR of claim 5, wherein the two antigen-specific targeting regions are arranged in tandem and are separated by a linker peptide.

27. A polynucleotide encoding the bispecific CAR of claim 1.

28. A genetically engineered cell derived from a T-lymphocyte (T-cell), wherein the genetically engineered cell expresses the bispecific CAR of claim 1.

29. A method for treating a disease cancer in a subject in need thereof, comprising:
   administering a therapeutically effective amount of a pharmaceutical composition comprising the genetically engineered cell of claim 28 and a pharmaceutically acceptable carrier to the subject so as to treat the cancer, wherein the two antigen-specific targeting regions target an antigen associated with the cancer.

30. A method of producing T-cells expressing a CAR, comprising:
   i. transfecting one or more T-cells with a vector comprising the polynucleotide of claim 27; and
   ii. stimulating the one or more T-cells, whereby the T-cells proliferate so as to produce T-cells expressing a CAR.

* * * * *

UNITED STATES PATENT AND TRADEMARK OFFICE
CERTIFICATE OF CORRECTION

PATENT NO. : 12,091,459 B2
APPLICATION NO. : 18/162447
DATED : September 17, 2024
INVENTOR(S) : Michael Jensen Page 1 of 1

It is certified that error appears in the above-identified patent and that said Letters Patent is hereby corrected as shown below:

In the Claims

Column 52, Line 14-15 Claim 29, first Line: the word "disease" should be removed.

Signed and Sealed this
Eighteenth Day of February, 2025

Coke Morgan Stewart
*Acting Director of the United States Patent and Trademark Office*